United States Patent
Wainer et al.

(10) Patent No.: US 10,130,594 B2
(45) Date of Patent: *Nov. 20, 2018

(54) USE OF FENOTEROL AND FENOTEROL ANALOGUES IN THE TREATMENT OF GLIOBLASTOMAS AND ASTROCYTOMAS

(71) Applicants: The United States of America, as represented by the Secretary, Department of Health and Human Services, Washington, DC (US); SRI International, Menlo Park, CA (US)

(72) Inventors: Irving W. Wainer, Washington, DC (US); Michel Bernier, Pikesville, MD (US); Lawrence Robert Toll, Redwood City, CA (US); Lucita Arenas Jimenez, Menlo Park, CA (US)

(73) Assignees: The United States of America, as represented by the Secretary, Department of Health and Human Services, Washington, DC (US); SRI International, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/273,147

(22) Filed: Sep. 22, 2016

(65) Prior Publication Data
US 2017/0007556 A1    Jan. 12, 2017

Related U.S. Application Data

(63) Continuation of application No. 13/583,206, filed as application No. PCT/US2011/027988 on Mar. 10, 2011, now Pat. No. 9,492,405.

(60) Provisional application No. 61/312,642, filed on Mar. 10, 2010.

(51) Int. Cl.
A61K 31/137 (2006.01)
A61K 45/06 (2006.01)

(52) U.S. Cl.
CPC ............ *A61K 31/137* (2013.01); *A61K 45/06* (2013.01)

(58) Field of Classification Search
None
See application file for complete search history.

(56) References Cited

U.S. PATENT DOCUMENTS

| 3,966,814 | A  | 6/1976  | Schromm et al. |
| 5,795,564 | A  | 8/1998  | Aberg et al. |
| 6,015,837 | A  | 1/2000  | Etlinger et al. |
| 6,589,508 | B1 | 7/2003  | Aberg et al. |
| 6,664,424 | B2 | 12/2003 | Booth et al. |
| 6,747,043 | B2 | 6/2004  | Moran et al. |
| 6,866,839 | B2 | 3/2005  | Aberg et al. |
| 7,045,658 | B2 | 5/2006  | Biggadike et al. |
| 2002/0132830 | A1 | 9/2002 | Morley |
| 2004/0192783 | A1 | 9/2004 | Morley |
| 2005/0107417 | A1 | 5/2005 | Germeyer et al. |
| 2005/0131072 | A1 | 6/2005 | Aberg et al. |

FOREIGN PATENT DOCUMENTS

| BE | 635 889 A | 12/1963 |
| CH | 564 509 | 7/1975 |
| DE | 2 010 883 | 9/1971 |
| DE | 2 136 643 | 2/1972 |
| GB | 1 283 632 | 8/1972 |
| GB | 1 360 658 | 7/1974 |
| JP | 05 097707 | 4/1993 |
| JP | 5302194 | 6/2013 |
| WO | WO 98/01099 | 1/1998 |
| WO | WO 99/16430 | 4/1999 |
| WO | WO 00/18389 | 4/2000 |
| WO | WO 2005/042486 | 5/2005 |
| WO | WO 2005/092333 | 10/2005 |
| WO | WO 2006/015830 | 2/2006 |
| WO | WO 2006/074897 | 7/2006 |
| WO | WO 2008/022038 | 2/2008 |
| WO | WO 2008/075104 | 6/2008 |
| WO | WO 2009/043355 | 4/2009 |

OTHER PUBLICATIONS

Paul et al. (AACR Annual Meeting 2014; Apr. 5-9, 2014, abstract 4535) (Year: 2014).*
Bernier et al., Pharmacology Research & Perspectives, 1(2), 2013 (Year: 2013).*
Andersson, "Some new positive inotropic agents," *Acta Med Scand Suppl.* 707:65-73, 1986 (Abstract only).
Bryan et al., "Demonstration of Catecholamine and Resorcinolamine Derivatives as Formaldehyde-Induced Fluorescence in Protein Models," *Journal of Histochemistry and Cytochemistry*, vol. 36, No. 6, pp. 615-620, 1988.
Carie et al., "A chemical biology approach identifies a beta-2 adrenergic receptor against that causes human tumor regression by blocking the Raf-1/Mek-1/Erk1/2 pathway," *Oncogene*, vol. 26, No. 26, pp. 3777-3788, May 31, 2007.
Chelmicka-Schorr et al., "C-6 Glioma Growth in Rats: Suppression with a β-Adrenergic Agonist and a Phosphodiesterase Inhibitor," *Annals of Neurology*, vol. 8, No. 4, 447-449, Oct. 1980.
Gleiter, "Fenoterol: Pharmacology and Clinical Use," *Cardiovascular Drug Reviews*, vol. 17, No. 1, pp. 87-106, 1999.
Goldman et al., *Cecil Textbook of Medicine*, Ed. 21, vol. 1, 1060-1074, 2000.

(Continued)

*Primary Examiner* — Umamaheswari Ramachandran
(74) *Attorney, Agent, or Firm* — Klarquist Sparkman, LLP

(57) ABSTRACT

This disclosure concerns the discovery of the use of fenoterol and (R,R)- and (R,S)-fenoterol analogs for the treatment of a tumor expressing a β2-adrenergic receptor, such as a primary brain tumor, including a glioblastoma or astrocytoma expressing a β2-adrenergic receptor. In one example, the method includes administering to a subject a therapeutically effective amount of fenoterol, a specific fenoterol analog or a combination thereof to reduce one or more symptoms associated with the tumor, thereby treating the tumor in the subject.

16 Claims, 10 Drawing Sheets

(56) References Cited

OTHER PUBLICATIONS

Irmer et al., "Treatment of severe congestive heart failure with the beta-agonist fenoterol," *Klin Wochenschr*. 59:639-645, 1981 (Abstract only).

Johnson et al., "Relationships between drug activity in NCI preclinical in vitro and in vivo models and early clinical trials," *British J of Cancer*, 84(10) 1424-1431, 2001.

Jozwiak et al., "Comparative Molecular Field Analysis of the Binding of the Stereoisomers of Fenoterol and Fenoterol Derivatives to the $\beta_2$ Adrenergic Receptor," *J. Med. Chem.* 50: 2903-2915, 2007.

Jozwiak et al., "Comparative molecular field analysis of fenoterol derivatives: A platform towards highly selective and effective p2 -adrenergic receptor agonists," *Bioorganic & Medicinal Chemistry*, 18, 728-736, 2010.

Juergens et al., "Different Mechanisms of Action of Beta2-Adrenergic Receptor Agonists: A Comparison of Reproterol, Fenoterol and Salbutamol on Monocyte Cyclic-Amp and Leukotriene B4 Production In Vitro," *Eur J Med Res*, 9: 365-370, Jul. 30, 2004.

Kaiser et al., "Identification and Quantification of β-Adrenoceptor Sites in Red Blood Cells from Rats," *Naunyn-Schmiedeberg's Arch. Pharmacol.* 305: 41-50, 1978.

Kinnard et al., "Sympathetic nervous system and glioma growth," *European Journal of Cancer and Clinical Oncology*, vol. 22, No. 4, pp. 501-503, Apr. 1, 1986.

Lin et al., "Separation of enantiomers of drugs by capillary electrophoresis. Part 8. B-Cyclodextrin as chiral solvating agent," *Talanta*, 46(4), pp. 743-749, 1998.

Mugge et al., "Effects of the beta 2-adrenoceptor agonists fenoterol and salbutamol on force of contraction in isolated human ventricular myocardium," *Klin Wochenschr*. 63:26-31, 1985 (Abstract only).

Notice of Reasons for Rejection issued by the Japanese Patent Office dated Aug. 13, 2014, for related Japanese Patent Application No. 2013-129406, with English-language translation.

Pérez-Sayáns et al., "Beta-adrenergic receptors in cancer: therapeutic implications," *Oncology Research*, vol. 19, No. 1, pp. 45-54, Jan. 1, 2010.

Perrin et al., "Rapid screening for chiral separations by short-end injection capillary electrophoresis using highly sulfated cyclodextrins as chiral selectors," *Electrophoresis*, 22(15), pp. 3203-3215, 2001.

Plummer et al., "Expression of inwardly rectifying potassium channels (GIRKs) and beta-adrenergic regulation of breast cancer cell lines," *BMC Cancer* 4: 93-103, Dec. 16, 2004.

Rominger et al., "Radioimmunological determination of fenoterol part ii, antiserum and tracer for the determination of fenoterol,"*Arzneimittel Forschung*, 40(8): 887-895, 1990. (Abstract only).

Rominger et al., "Radioimmunoligical Determination of Fenoterol Part II: Antiserum and tracer for the determination of fenoterol," *Drug Research*, 40 (11) No. 8, 1990.

Ryall et al., "$\beta_2$-Agonist fenoterol has greater effects on contractile function of rat skeletal muscles than clenbuterol," *Am. J. Physiol. Regul. Integr. Comp. Physiol*. 283: R1386-R1394, Aug. 2002.

Sausville et al., "Contributions of Human Tumor Xenografts to Anticancer Drug Development," *Cancer Research*, 66(7):3351-4, Apr. 1, 2006.

Schirrmacher et al., "Synthesis and preliminary evaluation of (R,R)(S,S) 5-(2-(2-[4-(2-[18F]fluoroethoxy)phenyl]-1-methylethylamino)-1-hydroxyethyl)-benzene-1,3-diol (18F]FEFE) for the in vivo visualization and quanitification of the β2-adrenergic receptor status in lung," *Bioorganic & Medicinal Chemistry Letters*, 13 (16), pp. 2687-2692, 2003.

Toll et al., "beta.2-Adrenergic Receptor Agonists Inhibit the Proliferation of 1321N1 Astrocytoma Cells," *Journal of Pharmacology and Experimental Therapeutics*, vol. 336, No. 2, pp. 524-532, Feb. 1, 2011.

Westphal et al., "A phase 3 trial of local chemotherapy with biodegradable carmustine (BCNU) wafers (Gliadel wafers) in patients with primary malignant glioma," *Neuro-Oncology*, 79-88, Apr. 2003.

Williams, "Stereoisomerism and Chirality," *Stereochemistry Review*, Fall 2005.

Woo et al., "Stereochemicstry of an Against Determines Coupling Preference of $\beta_2$-Adrenoceptor to Different G Proteins in Cardiomyocytes," *Mol. Pharm*. 75(1): 158-165, 2008 (originally published online Oct. 7, 2008).

Xiao et al., "Enhanced Gi Signaling Selectively Negates $\beta_2$-Adrenergic Receptor (AR)-but Not ($\beta_1$-AR-Mediated Positive Inotropic Effect in Myocytes From Failing Rat Hearts," *Circulation* 108: 1633-1639, 2003 (originally published online Sep. 15, 2003).

Yang et al., "Blocking CXCR3-Mediated Cyclic AMP Suppression Inhibits Brain Tumor Growth In vivo," *Cancer Res*. 67(2): 651-658, Jan. 15, 2007.

Zölβ, "Über spezifisch an den phenolischen Hydroxylgruppen acylierte Hydroxyphenyl-äthanolamine," *Sci Pharm* 32:76-92, 1964.

* cited by examiner

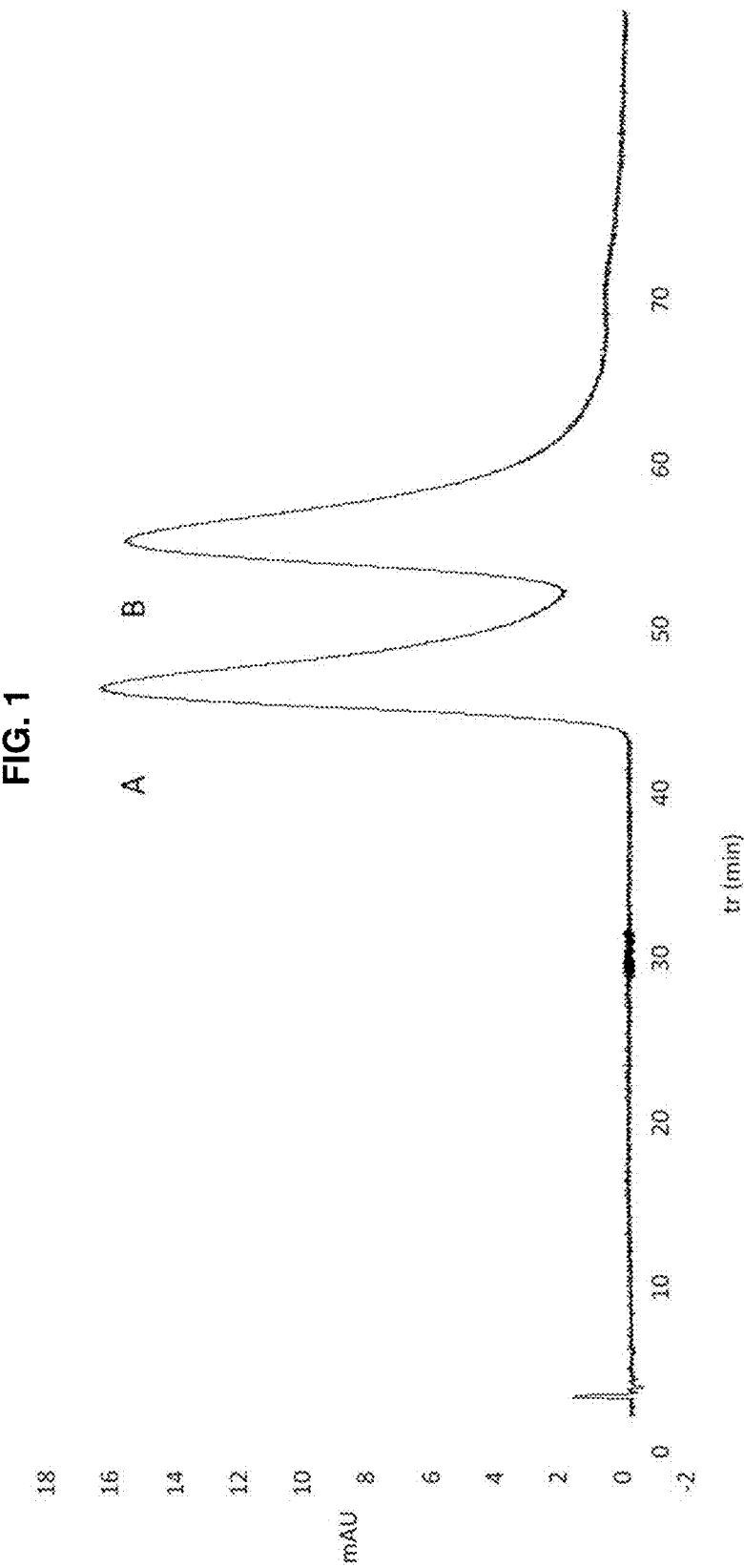

FIG. 5
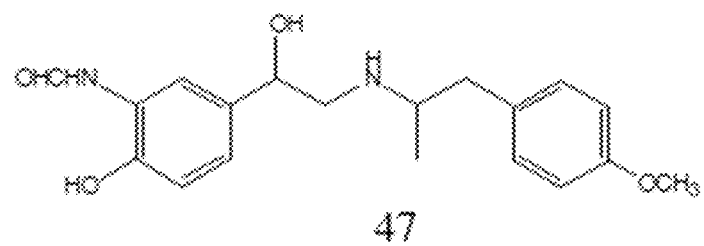
47
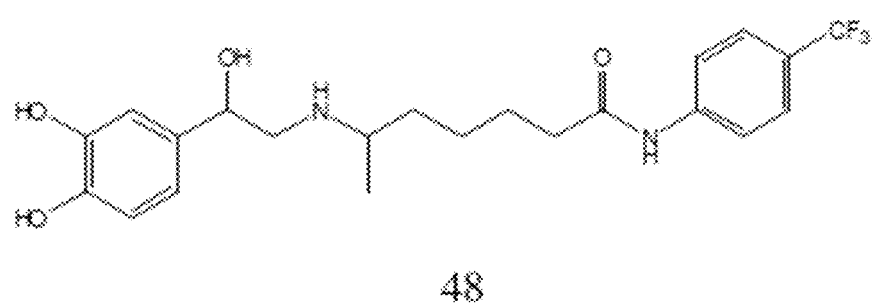
48
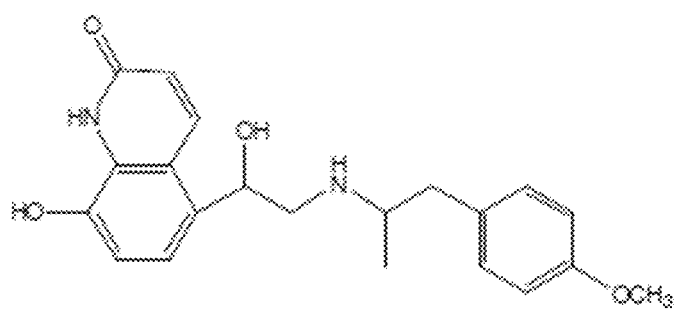
49
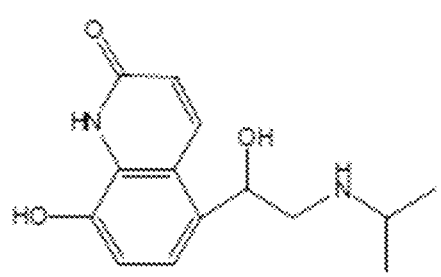
50
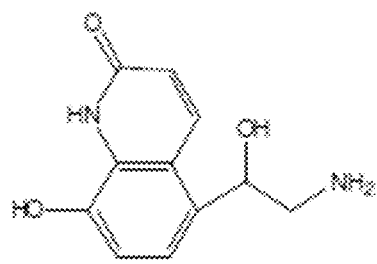
51

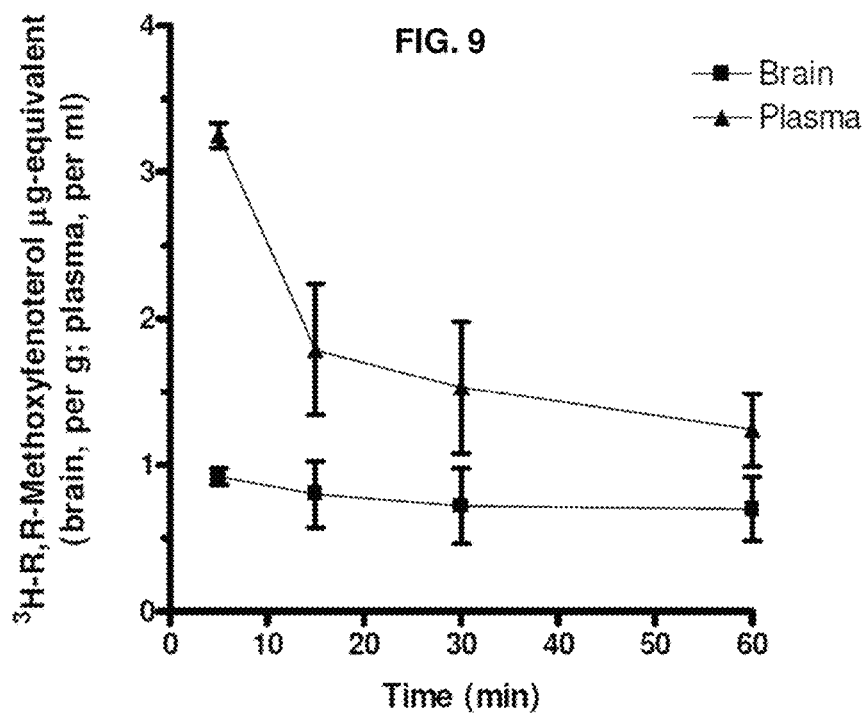
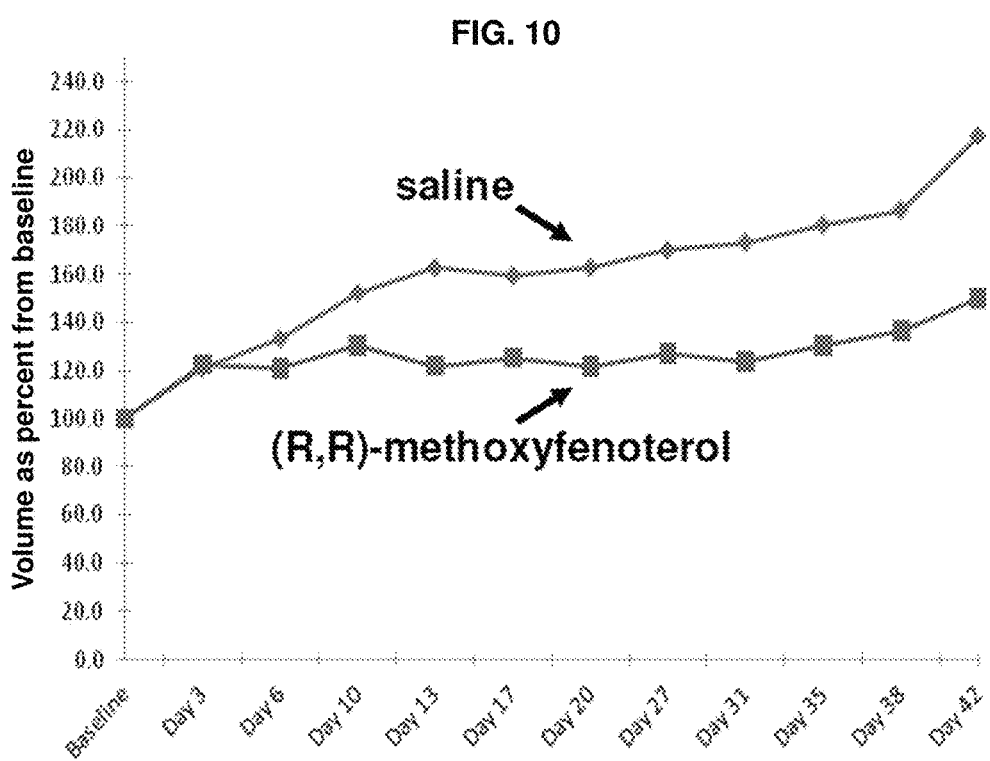

USE OF FENOTEROL AND FENOTEROL ANALOGUES IN THE TREATMENT OF GLIOBLASTOMAS AND ASTROCYTOMAS

CROSS REFERENCE TO RELATED APPLICATIONS

This is a continuation of U.S. application Ser. No. 13/583,206, filed Sep. 6, 2012, now issued as U.S. Pat. No. 9,492,405, which is the U.S. National Stage of International Application No. PCT/US2011/027988, filed Mar. 10, 2011, which was published in English under PCT Article 21(2), which in turn claims the benefit of U.S. Provisional Application No. 61/312,642, filed Mar. 10, 2010, each of which is incorporated herein by reference in its entirety.

ACKNOWLEDGEMENT OF GOVERNMENT SUPPORT

This invention was made with government support under contract number N01-AG-3-1008 awarded by the National Institutes of Health. The government has certain rights in this invention.

FIELD

The present disclosure relates to the field of (R,R)-fenoterol and (R,R)- or (R,S)-fenoterol analogues and in particular, to methods of their use in treating a tumor that expresses a β2-adrenergic receptor, such as a primary tumor expressing a β2-adrenergic receptor.

BACKGROUND

Cancer is the second leading cause of human death next to coronary disease in the United States. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. Cancer is soon predicted to become the leading cause of death.

Brain cancer is particularly difficult to treat because many common therapeutic agents are not able to pass through the blood brain barrier. Further, these tumors are often not detected until they are highly advanced. For example, the vast majority of malignant brain tumors are gliomas and astrocytomas, which are extremely lethal as the median survival from diagnoses is 12-15 months. The current clinical approaches to the treatment of gliomas and astrocytomas include a combination of surgery, radiation and chemotherapy, but these approaches have not significantly improved patient survival. Thus, the development of new therapies is an important area for drug development.

SUMMARY

This disclosure concerns the discovery that fenoterol and specific fenoterol analogues can be used to treat a tumor that is associated with β2-adrenergic receptor (AR) expression. The inventors have discovered that administration of fenoterol, specific fenoterol analogues or combinations thereof inhibit one or more signs or symptoms (such as tumor growth) associated with a tumor that expresses a β2-AR. Using this discovery, the inventors developed the disclosed methods of treating a tumor expressing a β2-AR, for example a primary brain tumor expressing a β2-AR, such as an astrocytoma or glioblastoma expressing a β2-AR.

In some embodiments, the method includes administering a therapeutically effective amount of fenoterol, a fenoterol analogue or a combination thereof to treat a tumor expressing a β2-AR, such as to reduce or inhibit one or more signs or symptoms associated with the tumor (including inhibiting tumor growth or reducing tumor volume).

Exemplary chemical structures for fenoterol analogues that are highly effective at binding β2-ARs and can be used in the disclosed therapies are provided. By way of example, fenoterol analogues are represented by the following general formula:

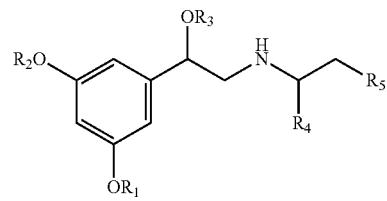

wherein $R_1$-$R_3$ independently are hydrogen, acyl, alkoxy carbonyl, amino carbonyl (carbamoyl) or a combination thereof;

$R_4$ is H or lower alkyl;

$R_5$ is lower alkyl,

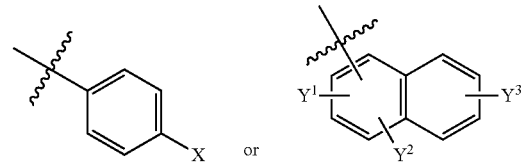

wherein X, $Y^1$, $Y^2$ and $Y^3$ independently are hydrogen, —$OR_6$ and —$NR_7R_8$;

$R_6$ is independently hydrogen, lower alkyl, acyl, alkoxy carbonyl or amino carbonyl; $R_7$ and $R_8$ independently are hydrogen, lower alkyl, alkoxy carbonyl, acyl or amino carbonyl and wherein the compound is optically active.

In some embodiments, $R_1$-$R_3$ independently are hydrogen; $R_4$ is a lower alkyl (such as, $CH_3$ or $CH_2CH_3$); $R_5$ is a lower alkyl,

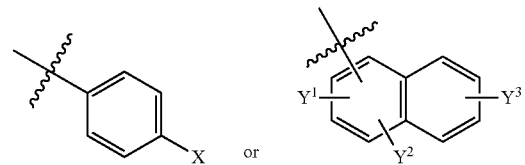

wherein X, $Y^1$, $Y^2$ and $Y^3$ independently are hydrogen, —$OR_6$ and —$NR_7R_8$; $R_6$ is independently hydrogen, lower alkyl, acyl, alkoxy carbonyl or amino carbonyl; $R_7$ and $R_8$ independently are hydrogen, lower alkyl, alkoxy carbonyl, acyl or amino carbonyl and wherein the compound is optically active.

In some embodiments, $R_1$-$R_3$ independently are hydrogen; $R_4$ is a methyl or an ethyl; $R_5$ is

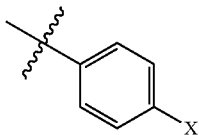

wherein X is —OH or —OCH$_3$.

In some embodiments, $R_1$-$R_3$ independently are hydrogen; $R_4$ is a methyl or an ethyl; $R_5$ is

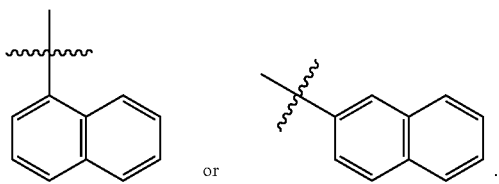 [SMILES: *c1cccc2ccccc12 ; *c1ccc2ccccc2c1]

or

In some embodiments, the method includes administering a therapeutically effective amount of a pharmaceutical composition containing fenoterol, any of the disclosed fenoterol analogues or a combination thereof and a pharmaceutically acceptable carrier to treat a tumor expressing a β2-AR, such as a primary brain tumor expressing β2-AR expression. For example, the disclosed (R,R)-fenoterol and (R,R)- or (R,S)-fenoterol analogues (e.g., (R,R)-methoxy-ethylfenoterol, (R,R)-methoxyfenoterol, (R,R)-napthylfenoterol, (R,R)-ethylfenoterol and (R,S)-napthylfenoterol) are effective at treating a primary brain tumor expressing a β2-AR, such as a glioblastoma or astrocytoma expressing a β2-AR. In some embodiments, the method further includes selecting a subject having or at risk of developing a tumor associated with β2-AR expression. For example, a subject is selected for treatment by determining that the tumor expresses β2-ARs. In one particular example, the method further includes selecting a subject that does not have a bleeding disorder. In further examples, the method includes administering one or more therapeutic agents in addition to fenoterol, a fenoterol analogue or combination thereof. The methods can include administration of the one or more therapeutic agents separately, sequentially or concurrently, for example in a combined composition with fenoterol, a fenoterol analogue or combinations thereof.

The foregoing and other features will become more apparent from the following detailed description of several embodiments, which proceeds with reference to the accompanying figures.

BRIEF DESCRIPTION OF THE DRAWINGS

FIG. 1 illustrates the chromatographic separation of (S,S)- and (R,R)-fenoterol.

FIG. 5 illustrates the chemical structures of compounds 47-51.

FIG. 7A shows that (R,R)-fenoterol (■) is 1000 times more potent than both (S,S)-fenoterol (▼) and forskolin (●). FIG. 7B shows the selective β2-AR antagonist ICI 118-551 at 1 nM (▼) and 3 nM (♦) induces a parallel rightward shift in the (R,R)-fenoterol (■) dose response curve.

FIG. 9 illustrates that IV administration of [$^3$H]-(R,R)-methoxyfenoterol is an effective method of delivering [$^3$H]-(R,R)-methoxyfenoterol to the brain as this compound was demonstrated to pass through the blood brain barrier. FIG. 9 provides a comparison of [$^3$H]-(R,R)-methoxyfenoterol levels in brain and plasma isolated from male Sprague-Dawley rats. The brain (µg-equiv/g) and plasma (µg-equiv/ml) levels of [$^3$H]-(R,R)-methoxyfenoterol were measured over 60 minutes. Each point represents the mean±s.e. of three rats.

FIG. 10 illustrates (R,R)-methoxyfenoterol-growth inhibition of a 1321N1 xenograft implanted in the flank of SKID mice.

DETAILED DESCRIPTION OF SEVERAL EMBODIMENTS

I. Introduction

Figure 2A:
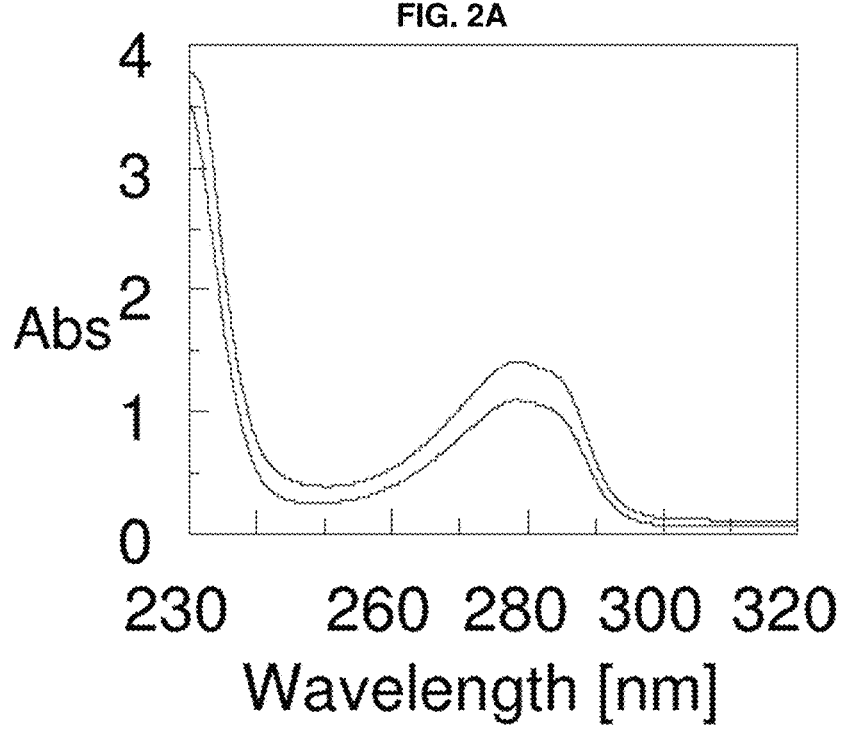
FIG. 2A is an ultraviolet spectra of (R,R)- and (S,S)-fenoterol.

Fenoterol, 5-[1-hydroxy-2[[2-(4-hydroxyphenyl)-1-methylethyl]-amino]ethyl]1,2-benzenediol, is a β2-AR agonist that has traditionally been used for the treatment of pulmonary disorders such as asthma. This drug has two chiral (asymmetric) carbons that can each be independently arranged in an R or S configuration, so that the drug exists in distinct (R,R), (R,S), (S,R) and (S,S) forms known as stereoisomers. Fenoterol is commercially available as a racemic mixture of the (R,R)- and (S,S)-compounds.

Fenoterol acts as an agonist that binds to and activates the β2-AR. This activity has led to its clinical use in the treatment of asthma because this agonist's activity dilates constricted airways. Additional therapeutic uses for fenoterol remain to be thoroughly explored.

This disclosure reports the ability of fenoterol, specific fenoterol analogues or a combination thereof to treat a tumor that expresses a β2-AR. In particular, this disclosure provides fenoterol analogues that bind the β2-AR with comparable or greater activity than fenoterol. In one embodiment, the optically active fenoterol analogues are substantially purified from a racemic mixture. For example, an optically active fenoterol analogue is purified to represent greater than 90%, often greater than 95% of the composition. These analogues can be used to treat a tumor that expresses a β2-AR, such as a primary tumor associated with increased β2-AR expression. It is specifically contemplated that (R,R)-fenoterol as well as disclosed (R,R)- and (R,S)-fenoterol analogues (or a combination thereof) can be used to treat a primary tumor, such as a primary brain tumor including a glioblastoma or astrocytoma expressing a β2-AR.

II. Abbreviations and Terms

AR: adrenergic receptor
CD: circular dichroism
CoMFA: comparative molecular field analysis
HPLC: high performance liquid chromatography
IAM-PC: immobilized artificial membrane chromatographic support
ICYP: [$^{125}$I]cyanopindolol
UV: ultraviolet Unless otherwise explained, all technical and scientific terms used herein have the same meaning as commonly understood by one of ordinary skill in the art to which the disclosed subject matter belongs. Definitions of common terms in chemistry terms may be found in *The McGraw-Hill Dictionary of Chemical Terms*, 1985, and *The Condensed Chemical Dictionary*, 1981. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Except as otherwise noted, any quantitative values are approximate whether the word "about" or "approximately" or the like are stated or not. The materials, methods, and examples described herein are illustrative only and not intended to be limiting. Any molecular weight or molecular mass values are approximate and are provided only for description. Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

In order to facilitate review of the various embodiments disclosed herein, the following explanations of specific terms are provided:

Acyl: A group of the formula RC(O)— wherein R is an organic group.

Acyloxy: A group having the structure —OC(O)R, where R may be an optionally substituted alkyl or optionally substituted aryl. "Lower acyloxy" groups are those where R contains from 1 to 10 (such as from 1 to 6) carbon atoms.

Administration: To provide or give a subject a composition, such as a pharmaceutical composition including fenoterol and/or one or more fenoterol analogues, by any effective route. Exemplary routes of administration include, but are not limited to, injection (such as subcutaneous, intramuscular, intradermal, intraperitoneal (ip), and intravenous (iv)), oral, sublingual, rectal, transdermal, intranasal, vaginal and inhalation routes.

Alkoxy: A radical (or substituent) having the structure —O—R, where R is a substituted or unsubstituted alkyl. Methoxy (—OCH$_3$) is an exemplary alkoxy group. In a substituted alkoxy, R is alkyl substituted with a non-interfering substituent. "Thioalkoxy" refers to —S—R, where R is substituted or unsubstituted alkyl. "Haloalkyloxy" means a radical —OR where R is a haloalkyl.

Alkoxy carbonyl: A group of the formula —C(O)OR, where R may be an optionally substituted alkyl or optionally substituted aryl. "Lower alkoxy carbonyl" groups are those where R contains from 1 to 10 (such as from 1 to 6) carbon atoms.

Alkyl: An acyclic, saturated, branched- or straight-chain hydrocarbon radical, which, unless expressly stated otherwise, contains from one to fifteen carbon atoms; for example, from one to ten, from one to six, or from one to four carbon atoms. This term includes, for example, groups such as methyl, ethyl, n-propyl, isopropyl, isobutyl, t-butyl, pentyl, heptyl, octyl, nonyl, decyl, or dodecyl. The term "lower alkyl" refers to an alkyl group containing from one to ten carbon atoms. Unless expressly referred to as an "unsubstituted alkyl," alkyl groups can either be unsubstituted or substituted. An alkyl group can be substituted with one or more substituents (for example, up to two substituents for each methylene carbon in an alkyl chain). Exemplary alkyl substituents include, for instance, amino groups, amide, sulfonamide, halogen, cyano, carboxy, hydroxy, mercapto, trifluoromethyl, alkyl, alkoxy (such as methoxy), alkylthio, thioalkoxy, arylalkyl, heteroaryl, alkylamino, dialkylamino, alkylsulfano, keto, or other functionality.

Amino carbonyl (carbamoyl): A group of the formula C(O)N(R)R', wherein R and R' are independently of each other hydrogen or a lower alkyl group.

Astrocytoma: A tumor of the brain that originates in astrocytes. An astrocytoma is an example of a primary tumor. Astrocytomas are the most common glioma, and can occur in most parts of the brain and occasionally in the spinal cord. However, astrocytomas are most commonly found in the cerebrum. In one example, an astrocytoma is inhibited by administering, to a subject, a therapeutic effective amount of fenoterol, a fenoterol analogue or a combination thereof, thereby inhibiting astrocytoma growth.

β2-adrenergic receptor (β2-AR): A subtype of adrenergic receptors that are members of the G-protein coupled receptor family β2-AR sub-type is involved in respiratory diseases, cardiovascular diseases and premature labor and as disclosed herein tumor development. Increased expression of β2-ARs can serve as therapeutic targets. Currently, a number of drugs e.g., albuterol, formoterol, isoproternol, or salmeterol have β2-AR agonist activities. As disclosed herein, fenoterol and fenoterol analogues are β2-AR agonists. In an example, fenoterol, a fenoterol analogue or a combination thereof is administered to a subject to reduce or inhibit one or more symptoms or signs associated with a tumor expressing a β2-AR (such as increased β2-AR expression), for example a primary brain tumor expressing a β2-AR.

Blood-brain barrier (BBB): The barrier formed by epithelial cells in the capillaries that supply the brain and central nervous system. This barrier selectively allows entry of substances such as water, oxygen, carbon dioxide, and nonionic solutes such as glucose, alcohol, and general anesthetics, while blocking entry of other substances. Some small molecules, such as amino acids, are taken across the barrier by specific transport mechanisms. In one example, fenoterol or disclosed fenoterol analogues are capable of passing through the barrier.

Carbamate: A group of the formula —OC(O)N(R)—, wherein R is H, or an aliphatic group, such as a lower alkyl group or an aralkyl group.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth. In one embodiment, a chemotherapeutic agent is an agent of use in treating neoplasms such as solid tumors, including a tumor associated with β2-AR expression. In one embodiment, a chemotherapeutic agent is radioactive molecule. In some embodiments, fenoterol, a fenoterol analogue or a combination thereof is a chemotherapeutic agent. In one example, a chemotherapeutic agent is carmustine, lomustine, procarbazine, streptozocin, or a combination thereof. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Control or Reference Value: A "control" refers to a sample or standard used for comparison with a test sample. In some embodiments, the control is a sample obtained from a healthy subject or a tumor tissue sample obtained from a patient diagnosed with tumor that did not respond to treatment with fenoterol, a fenoterol analogue or a combination thereof. In some embodiments, the control is a historical control or standard reference value or range of values (such as a previously tested control sample, such as a group of subjects which do not have a tumor expressing β2-ARs or group of samples that represent baseline or normal values, such as the level of β2-ARs in tumor tissue that does not respond to treatment with fenoterol, a fenoterol analogue or a combination thereof).

Derivative: A chemical substance that differs from another chemical substance by one or more functional groups. Preferably, a derivative (such as a fenoterol analogue) retains a biological activity (such as β2-AR stimulation) of a molecule from which it was derived (such as a fenoterol or a fenoterol analogue).

Glioblastoma: A common and malignant form of a primary brain tumor. A glioblastoma is a grade IV astrocytoma and usually spreads rapidly in the brain. In one example, a glioblastoma is inhibited by administering a therapeutic effective amount of fenoterol, a fenoterol analogue or a combination thereof to a subject, thereby inhibiting one or more symptoms associated with the glioblastoma.

Isomers: Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that contain two or more chiral centers and are not mirror images of one another are termed "diastereomers." Steroisomers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers, respectively). A chiral compound can exist as either an individual enantiomer or as a mixture thereof. A mixture containing equal proportions of the enantiomers is called a "racemic mixture."

The compounds described herein may possess one or more asymmetric centers; such compounds can therefore be produced as individual (R), (S), (R,R), (R,S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., March, *Advanced Organic Chemistry*, 4th edition, New York: John Wiley and Sons, 1992, Chapter 4).

Optional: "Optional" or "optionally" means that the subsequently described event or circumstance can but need not occur, and that the description includes instances where said event or circumstance occurs and instances where it does not.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds or molecules, such as one or more nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phenyl: Phenyl groups may be unsubstituted or substituted with one, two or three substituents, with substituent(s) independently selected from alkyl, heteroalkyl, aliphatic, heteroaliphatic, thioalkoxy, halo, haloalkyl (such as —$CF_3$), nitro, cyano, —OR (where R is hydrogen or alkyl), —N(R)R' (where R and R' are independently of each other hydrogen or alkyl), —COOR (where R is hydrogen or alkyl) or —C(O)N(R')R" (where R' and R" are independently selected from hydrogen or alkyl).

Purified: The term "purified" does not require absolute purity; rather, it is intended as a relative term. Thus, for example, a purified preparation is one in which a desired component such as an (R,R)-enantiomer of fenoterol is more enriched than it was in a preceding environment such as in a (±)-fenoterol mixture. A desired component such as (R,R)-enantiomer of fenoterol is considered to be purified, for example, when at least about 70%, 80%, 85%, 90%, 92%, 95%, 97%, 98%, or 99% of a sample by weight is composed of the desired component. Purity of a compound may be determined, for example, by high performance liquid chromatography (HPLC) or other conventional methods. In an example, the specific fenoterol analogue enantiomers are purified to represent greater than 90%, often greater than 95% of the other enantiomers present in a purified preparation. In other cases, the purified preparation may be essentially homogeneous, wherein other stereoisomers are less than 1%.

Compounds described herein may be obtained in a purified form or purified by any of the means known in the art, including silica gel and/or alumina chromatography. See, e.g., *Introduction to Modern Liquid Chromatography*, 2nd Edition, ed. by Snyder and Kirkland, New York: John Wiley and Sons, 1979; and *Thin Layer Chromatography*, ed. by Stahl, New York: Springer Verlag, 1969. In an example, a compound includes purified fenoterol or fenoterol analogue with a purity of at least about 70%, 80%, 85%, 90%, 92%, 95%, 97%, 98%, or 99% of a sample by weight relative to other contaminants. In a further example, a compound includes at least two purified stereoisomers each with a purity of at least about 70%, 80%, 85%, 90%, 92%, 95%, 97%, 98%, or 99% of a sample by weight relative to other contaminants. For instance, a compound can include a substantially purified (R,R)-fenoterol analogue and a substantially purified (R,S)-fenoterol analogue.

Subject: The term "subject" includes both human and veterinary subjects, for example, humans, non-human primates, dogs, cats, horses, rats, mice, and cows. Similarly, the term mammal includes both human and non-human mammals.

Therapeutically Effective Amount: A quantity of a specified agent sufficient to achieve a desired effect in a subject being treated with that agent. For example, this may be the amount of (R,R)-fenoterol or (R,R)- or (R,S)-fenoterol analogue useful in reducing, inhibiting, and/or treating a primary tumor, such as a glioblastoma or astrocytoma associated with β2-AR expression. Ideally, a therapeutically effective amount of an agent is an amount sufficient to reduce, inhibit, and/or treat the disorder in a subject without causing a substantial cytotoxic effect in the subject.

The effective amount of a composition useful for reducing, inhibiting, and/or treating a disorder in a subject will be dependent on the subject being treated, the severity of the disorder, and the manner of administration of the therapeutic composition. Effective amounts a therapeutic agent can be determined in many different ways, such as assaying for a reduction in tumor size or improvement of physiological condition of a subject having a tumor, such as a brain tumor. Effective amounts also can be determined through various in vitro, in vivo or in situ assays.

Tissue: A plurality of functionally related cells. A tissue can be a suspension, a semi-solid, or solid. Tissue includes cells collected from a subject such as the brain or a portion thereof.

Tumor: All neoplastic cell growth and proliferation, whether malignant or benign, and all pre-cancerous and cancerous cells and tissues. A primary tumor is tumor growing at the anatomical site where tumor progression began and proceeded to yield this mass. A primary brain tumor (also referred to as a glioma) is a tumor that originates in the brain. Exemplary primary brain tumors include astrocytomas, glioblastomas, ependymoma, oligodendrogliomas, and mixed gliomas. In some examples, a primary brain tumor is associated with β2-AR expression (such as increased β2-AR expression), such as an astrocytoma or glioblastoma associated with β2-AR expression.

Under conditions sufficient for: A phrase that is used to describe any environment that permits the desired activity.

In one example, under conditions sufficient for includes administering fenoterol and/or one or more fenoterol analogues or a combination thereof to a subject to at a concentration sufficient to allow the desired activity. In some examples, the desired activity is reducing or inhibiting a sign or symptom associated with a tumor (such as a primary brain tumor) can be evidenced, for example, by a delayed onset of clinical symptoms of the tumor in a susceptible subject, a reduction in severity of some or all clinical symptoms of the tumor, a slower progression of the tumor (for example by prolonging the life of a subject having the tumor), a reduction in the number of tumor reoccurrence, an improvement in the overall health or well-being of the subject, or by other parameters well known in the art that are specific to the particular disease. In one particulate example, the desired activity is preventing or inhibiting tumor growth, such as astrocytoma or glioblastoma growth. Tumor growth does not need to be completely inhibited for the treatment to be considered effective. For example, a partial reduction or slowing of growth such as at least about a 10% reduction, such as at least 20%, at least about 30%, at least about 40%, at least about 50% or greater is considered to be effective.

III. (R,R)-Fenoterol and Fenoterol Analogues

A. Chemical Structure

Some exemplary fenoterol analogues disclosed herein have the formula:

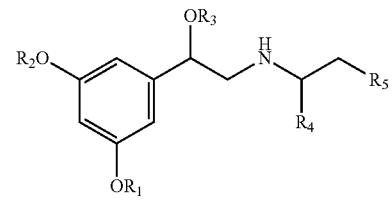

wherein $R_1$-$R_3$ independently are hydrogen, acyl, alkoxy carbonyl, amino carbonyl or a combination thereof;

$R_4$ is H or lower alkyl;

$R_5$ is lower alkyl,

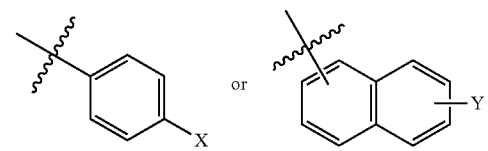

wherein X and Y independently are selected from hydrogen, lower —$OR_6$ and —$NR_7R_8$;

$R_6$ is lower alkyl or acyl; and $R_7$ and $R_8$ independently are hydrogen, lower alkyl, alkoxy carbonyl, acyl or amino carbonyl.

With continued reference to the general formula for fenoterol analogues above, Y may be —OH.

In one embodiment, $R_5$ is a 1- or 2-napthyl derivative optionally having 1, 2 or 3 substituents. Examples of such $R_5$ groups are represented by the formula

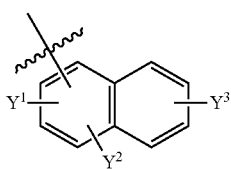

wherein $Y^1$, $Y^2$ and $Y^3$ independently are hydrogen, lower —$OR_6$ and —$NR_7R_8$;

$R_6$ is independently for each occurrence selected from lower alkyl and acyl; and $R_7$ and $R_8$ independently are hydrogen, lower alkyl, alkoxy carbonyl, acyl or amino carbonyl (carbamoyl). In particular compounds at least one of $Y^1$, $Y^2$ and $Y^3$ is —$OCH_3$.

Particular $R_5$ groups include those represented by the formulas

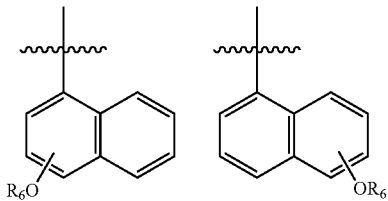

wherein $R_6$ is lower alkyl, such as methyl, ethyl, propyl or isopropyl or acyl, such as acetyl.

Exemplary $R_5$ groups include

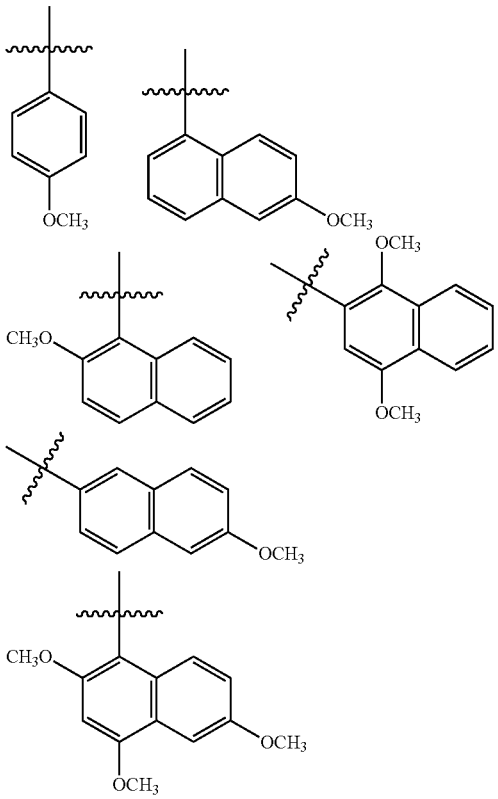

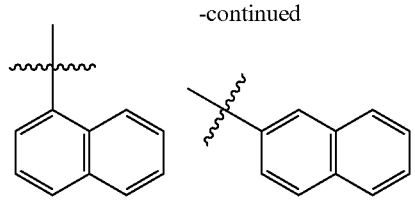

In one example, $R_4$ is lower alkyl and $R_5$ is

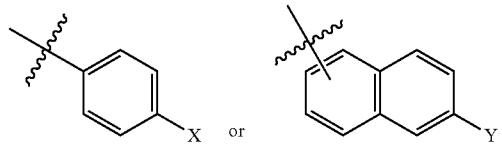

wherein X and Y independently are selected from H, lower alkyl —$OR_6$ and —$NR_7R_8$;

$R_6$ is lower alkyl; and $R_7$ and $R_8$ independently are hydrogen or lower alkyl.

In a further example, $R_4$ is selected from ethyl, n-propyl, and isopropyl and $R_5$ has the formula

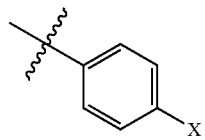

wherein X is H, —$OR_6$ or —$NR_7R_8$. For example, $R_6$ may be methyl or $R_7$ and $R_8$ are hydrogen.

In an additional example, $R_5$ has the formula

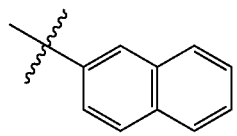 [SMILES: *c1ccc2ccccc2c1]

In further embodiments, $R_4$ is selected from methyl, ethyl, n-propyl and isopropyl and $R_5$ represents

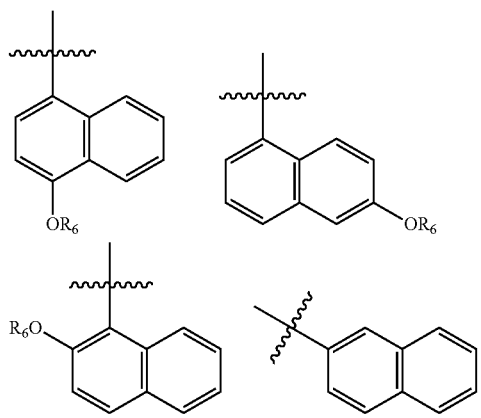

-continued

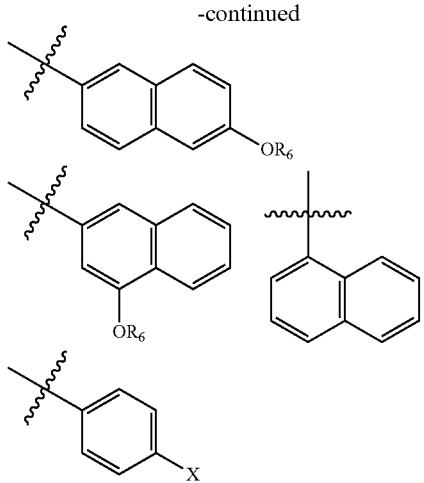

In some embodiments, $R_1$-$R_3$ independently are hydrogen; $R_4$ is a lower alkyl (such as, $CH_3$ or $CH_2CH_3$); $R_5$ is lower alkyl,

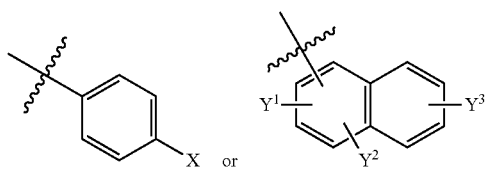

wherein X, $Y^1$, $Y^2$ and $Y^3$ independently are hydrogen, —$OR_6$ and —$NR_7R_8$; $R_6$ is independently hydrogen, lower alkyl, acyl, alkoxy carbonyl or amino carbonyl; $R_7$ and $R_8$ independently are hydrogen, lower alkyl, alkoxy carbonyl, acyl or amino carbonyl and wherein the compound is optically active.

In some embodiments, $R_1$-$R_3$ independently are hydrogen; $R_4$ is a methyl or an ethyl; $R_5$ is

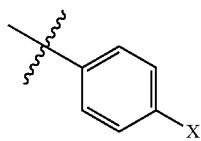

wherein X is —OH or —$OCH_3$.

In some embodiments, $R_1$-$R_3$ independently are hydrogen; $R_4$ is a methyl or an ethyl; $R_5$ is

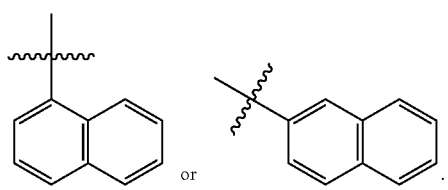 [SMILES: *c1cccc2ccccc12 ; *c1ccc2ccccc2c1]

Examples of suitable groups for $R_1$-$R_3$ that can be cleaved in vivo to provide a hydroxy group include, without limitation, acyl, acyloxy and alkoxy carbonyl groups. Compounds having such cleavable groups are referred to as "prodrugs." The term "prodrug," as used herein, means a compound which includes a substituent that is convertible in vivo (e.g., by hydrolysis) to a hydroxyl group. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed), *Design and Application of Prodrugs, Textbook of Drug Design and Development*, Chapter 5, 113 191 (1991); Bundgaard, et al., *Journal of Drug Delivery Reviews*, 8:1 38(1992); Bundgaard, *Pharmaceutical Sciences*, 77:285 et seq. (1988); and Higuchi and Stella (eds.) *Prodrugs as Novel Drug Delivery Systems*, American Chemical Society (1975).

An exemplary (R,R)-compound has the chemical structure of:

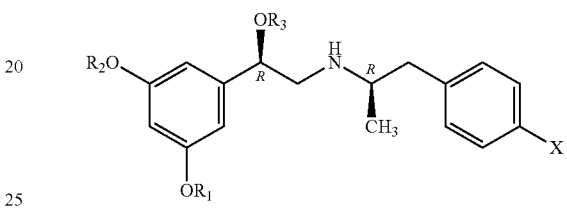

X and $R_1$-$R_3$ are as described above.

An additional exemplary (R,R)-compound has the chemical structure:

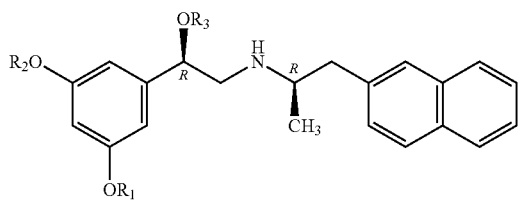

An exemplary (R,S)-compound has the chemical structure:

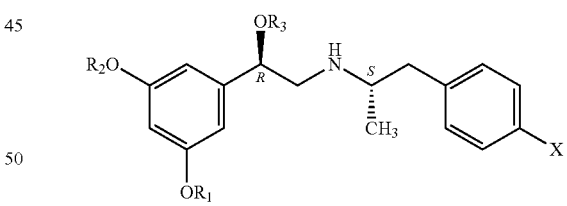

wherein X and $R_1$-$R_3$ are as described above.

An additional exemplary (R,S)-compound has the chemical structure:

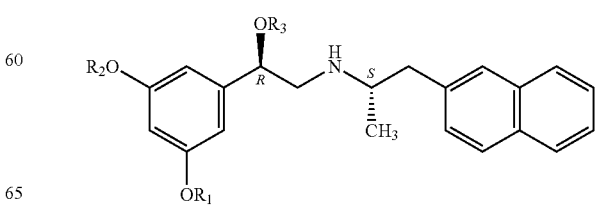

An exemplary (S,R)-compound has the chemical structure:

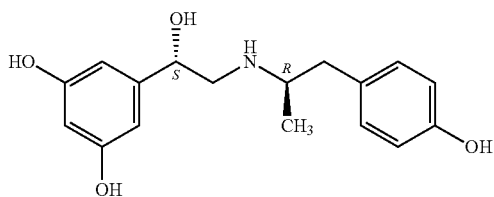

wherein X and $R_1$-$R_3$ are as described above.

An exemplary (S,S)-compound has the chemical structure:

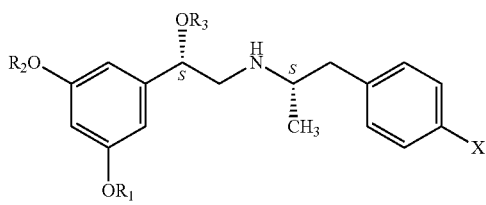

wherein X and $R_1$-$R_3$ are as described above.

Examples of chemical structures illustrating the various stereoisomers of fenoterol are provided below.

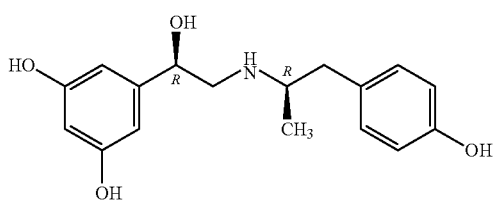

(R,R)-Fenoterol

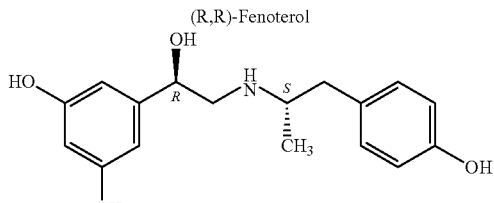

(R,S)-Fenoterol

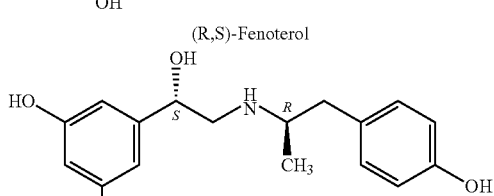

(S,R)-Fenoterol

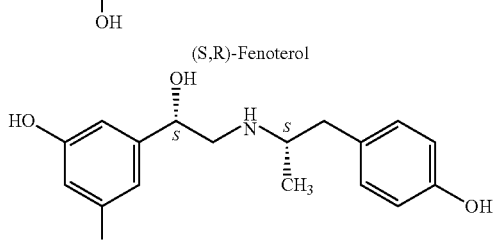

(S,S)-Fenoterol

Particular method embodiments contemplate the use of solvates (such as hydrates), pharmaceutically acceptable salts and/or different physical forms of (R,R)-fenoterol or any of the fenoterol analogues herein described.

1. Solvates, Salts and Physical Forms

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compound, methanol associated compounds, and the like. "Hydrate" is a solvate wherein the solvent molecule(s) is/are $H_2O$.

The disclosed compounds also encompass salts including, if several salt-forming groups are present, mixed salts and/or internal salts. The salts are generally pharmaceutically-acceptable salts that are non-toxic. Salts may be of any type (both organic and inorganic), such as fumarates, hydrobromides, hydrochlorides, sulfates and phosphates. In an example, salts include non-metals (e.g., halogens) that form group VII in the periodic table of elements. For example, compounds may be provided as a hydrobromide salt.

Additional examples of salt-forming groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Exemplary compounds disclosed herein possess at least one basic group that can form acid base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In a currently preferred embodiment, fenoterol is provided as a hydrobromide salt and exemplary fenoterol analogues are provided as their fumarate salts.

Additional counterions for forming pharmaceutically acceptable salts are found in *Remington's Pharmaceutical Sciences*, 19th Edition, Mack Publishing Company, Easton, Pa., 1995. In one aspect, employing a pharmaceutically acceptable salt may also serve to adjust the osmotic pressure of a composition.

In certain embodiments the compounds used in the method are provided are polymorphous. As such, the compounds can be provided in two or more physical forms, such as different crystal forms, crystalline, liquid crystalline or non-crystalline (amorphous) forms.

2. Use for the Manufacture of a Medicament

Any of the above described compounds (e.g., (R,R)-fenoterol or fenoterol analogues or a hydrate or pharmaceutically acceptable salt thereof) or combinations thereof are intended for use in the manufacture of a medicament for β2-AR stimulation in a subject or for the treatment of a primary brain tumor (e.g., astrocytoma or glioblastoma). Formulations suitable for such medicaments, subjects who may benefit from same and other related features are described elsewhere herein.

B. Methods of Synthesis

The disclosed fenoterol analogues can be synthesized by any method known in the art. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

Compounds as described herein may be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via open column chromatography or prep chromatography.

Suitable exemplary syntheses of fenoterol analogues are provided below:

Scheme I: An exemplary synthesis of 4 stereoisomers of 1-6 including the coupling of the epoxide formed from either (R)- or (S)-3',5'-dibenzyloxyphenylbromohydrin with the (R)- or (S)-enantiomer of the appropriate benzyl-protected 2-amino-3-benzylpropane (1-5) or the (R) or (S)-enantiomer of N-benzyl-2-aminoheptane (6).

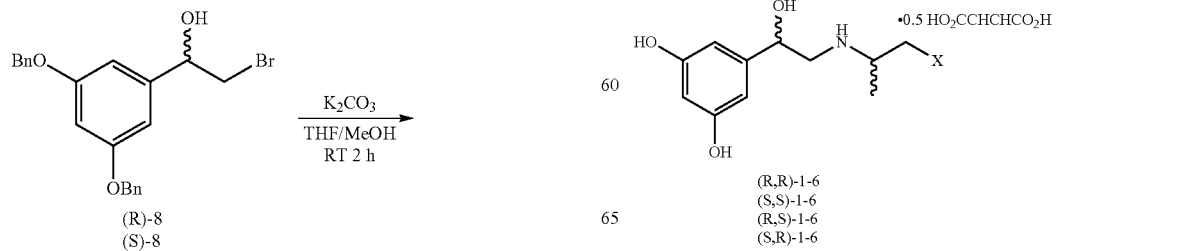

-continued

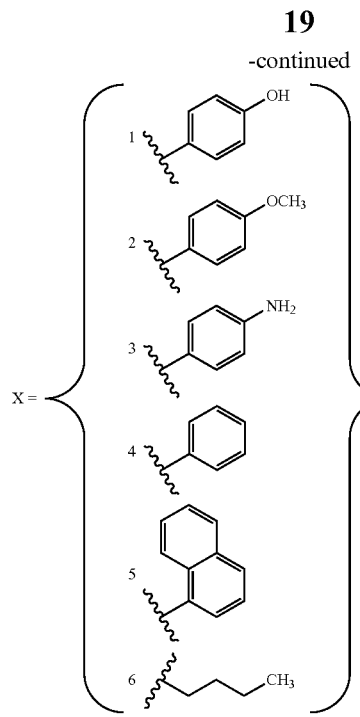

Scheme II: Exemplary synthesis of (R)-7 and (S)-7 using 2-phenethylamine. The resulting compounds may be deprotected by hydrogenation over Pd/C and purified as the fumarate salts.

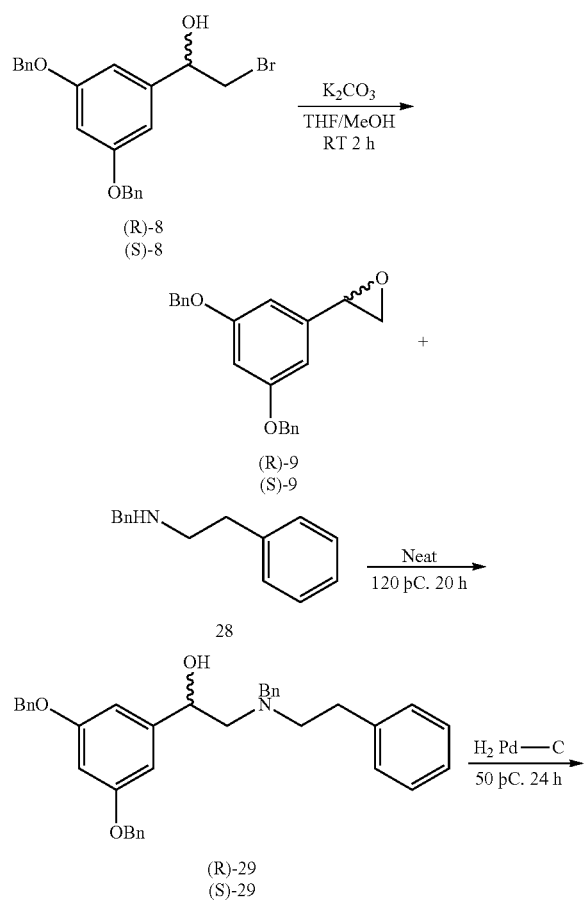

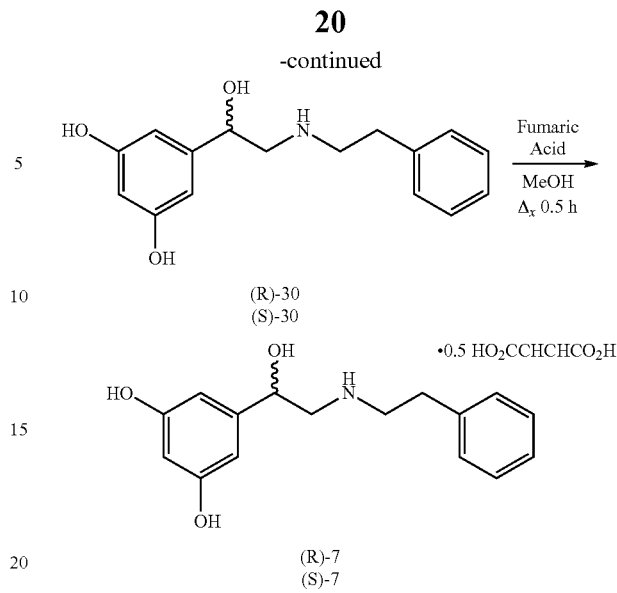

Scheme III describes an exemplary synthesis for the chiral building blocks used in Scheme II. The (R)- and (S)-3′,5′-dibenzyloxyphenyl-bromohydrin enantiomers were obtained by the enantiospecific reduction of 3,5-dibenzyloxy-α-bromoacetophenone using boron-methyl sulfide complex (BH$_3$SCH$_3$) and either (1R,2S)- or (1S,2R)- cis-1-amino-2-indanol. The required (R)- and (S)-2-benzylaminopropanes were prepared by enantioselective crystallization of the rac-2-benzylaminopropanes using either (R)- or (S)-mandelic acid as the counter ion.

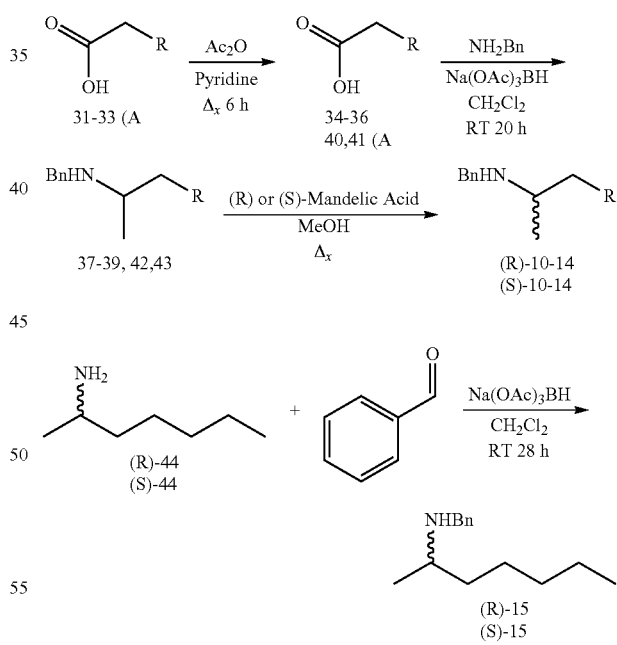

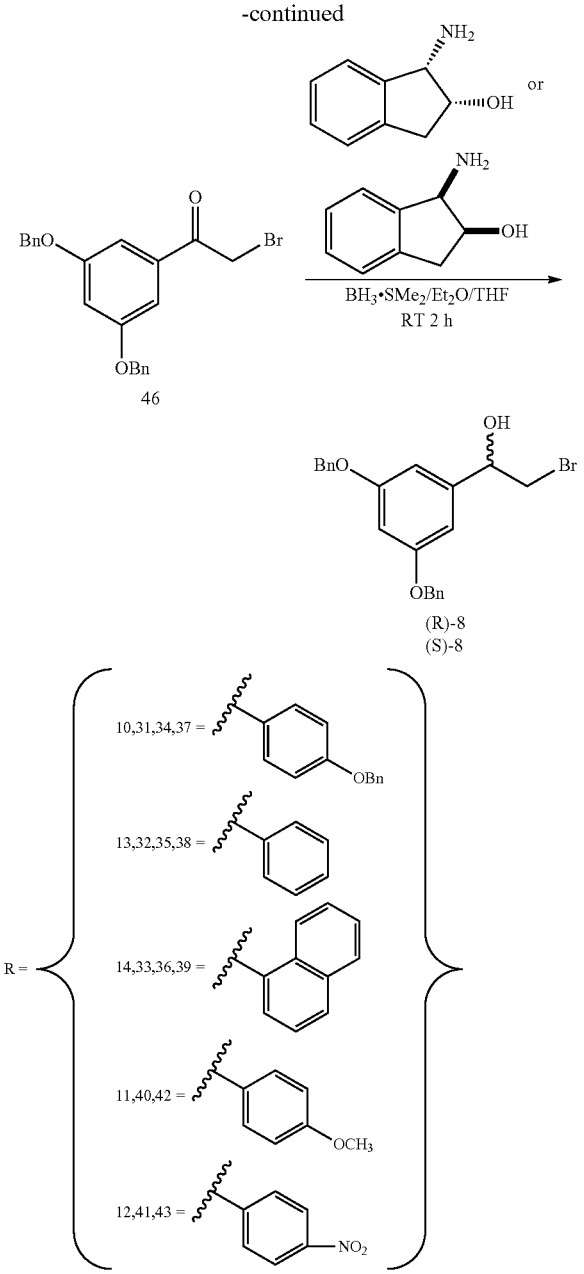

IV. Pharmaceutical Compositions

The disclosed (R,R)-fenoterol and fenoterol analogues can be useful, at least, for the treatment of a tumor that expresses a β2-AR, (such as increased β2-AR expression), including a primary brain tumor (e.g., an astrocytoma or glioblastoma) expressing a β2-AR. Accordingly, pharmaceutical compositions comprising at least one disclosed fenoterol compound and/or analogue are also described herein.

Formulations for pharmaceutical compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of (R,R)-fenoterol and disclosed fenoterol analogues.

Pharmaceutical compositions comprising at least one of these compounds can be formulated for use in human or veterinary medicine. Particular formulations of a disclosed pharmaceutical composition may depend, for example, on the mode of administration (e.g., oral or parenteral) and/or on the disorder to be treated (e.g., a tumor associated with β2-AR expression, such as a primary brain tumor). In some embodiments, formulations include a pharmaceutically acceptable carrier in addition to at least one active ingredient, such as a fenoterol compound.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The disclosed pharmaceutical compositions may be formulated as a pharmaceutically acceptable salt. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences*, 19th Edition, Mack Publishing Company, Easton, Pa., 1995. A pharmaceutically acceptable salt may also serve to adjust the osmotic pressure of the composition.

The dosage form of a disclosed pharmaceutical composition will be determined by the mode of administration chosen. For example, in addition to injectable fluids, oral dosage forms may be employed. Oral formulations may be liquid such as syrups, solutions or suspensions or solid such as powders, pills, tablets, or capsules. Methods of preparing such dosage forms are known, or will be apparent, to those skilled in the art.

Certain embodiments of the pharmaceutical compositions comprising a disclosed compound may be formulated in unit dosage form suitable for individual administration of precise dosages. The amount of active ingredient such as (R,R)-fenoterol administered will depend on the subject being treated, the severity of the disorder, and the manner of administration, and is known to those skilled in the art. Within these bounds, the formulation to be administered will contain a quantity of the extracts or compounds disclosed herein in an amount effective to achieve the desired effect in the subject being treated.

In particular examples, for oral administration the compositions are provided in the form of a tablet containing from about 1.0 to about 50 mg of the active ingredient, particularly about 2.0 mg, about 2.5 mg, 5 mg, about 10 mg, or about 50 mg of the active ingredient for the symptomatic adjustment of the dosage to the subject being treated. In one exemplary oral dosage regimen, a tablet containing from about 1 mg to about 50 mg (such as about 2 mg to about 10 mg) active ingredient is administered two to four times a day, such as two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

In one embodiment, the pharmaceutical composition is administered without concurrent administration of a second agent for the treatment of a tumor that expresses a β2-AR. In one specific, non-limiting example, one or more of the disclosed compositions is administered without concurrent administration of other agents, such as without concurrent administration of an additional agent also known to target the tumor. In other specific non-limiting examples, a therapeutically effective amount of a disclosed pharmaceutical composition is administered concurrently with an additional agent, including an additional therapy (such as, but not limited to, a chemotherapeutic agent, an additional β2-AR agonist, an anti-inflammatory agent, an anti-oxidant, or other agents known to those of skill in the art). For example, the disclosed compounds are administered in combination with a chemotherapeutic agent, anti-oxidants, anti-inflammatory drugs or combinations thereof.

In other examples, a disclosed pharmaceutical composition is administered an adjuvant therapy. For example, a pharmaceutical composition containing one or more of the disclosed compounds is administered orally daily to a subject in order to prevent or retard tumor growth. In one particular example, a composition containing equal portions of two or more disclosed compounds is provided to a subject. In one example, a composition containing unequal portions of two or more disclosed compounds is provided to the subject. For example, a composition contains unequal portions of a (R,R)-fenoterol derivative and a (S,R)-fenoterol derivative and/or a (R,S)-derivative. In one particular example, the composition includes a greater amount of the (S,R)- or (R,S)-fenoterol derivative (such as about 3 parts (S,R)-methoxy-ethylfenoterol or 3 parts (S,R)-methyloxy-fenoterol) than an (R,R)-fenoterol derivative (such as 1 part (R,R)-methoxy-ethylfenoterol or 1 part (R,R)-methyloxy-fenoterol). Such therapy can be given to a subject for an indefinite period of time to inhibit, prevent or reduce tumor reoccurrence.

V. Methods of Use

The present disclosure includes methods of treating disorders including reducing or inhibiting one or more signs or symptoms associated with a tumor expressing a β2-AR, such as a primary tumor. In some examples, the primary tumor is a primary brain tumor expressing a β2-AR, such as an increase in β2-AR expression. In one example, the primary brain tumor expressing a β2-AR is an astrocytoma. In other examples, the primary brain tumor expressing a β2-AR is a glioblastoma.

Disclosed methods include administering fenoterol, such as (R,R)-fenoterol, a disclosed fenoterol analogue or a combination thereof (and, optionally, one or more other pharmaceutical agents) to a subject in a pharmaceutically acceptable carrier and in an amount effective to treat the tumor expressing a β2-AR, such as a primary tumor. Treatment of a tumor includes preventing or reducing signs or symptoms associated with the presence of such tumor (for example, by reducing the size or volume of the tumor or a metastasis thereof). Such reduced growth can in some examples decrease or slow metastasis of the tumor, or reduce the size or volume of the tumor by at least 10%, at least 20%, at least 50%, or at least 75%, such as between 10%-90%, 20%-80%, 30%-70%, 40%-60%, including a 10%, 15%, 20%, 25%, 30%, 35%, 40%, 45%, 50%, 55%, 60%, 65%, 70%, 75%, 80%, 90%, or 95% reduction. In another example, treatment includes reducing the invasive activity of the tumor in the subject, for example by reducing the ability of the tumor to metastasize. In some examples, treatment using the methods disclosed herein prolongs the time of survival of the subject.

Routes of administration useful in the disclosed methods include but are not limited to oral and parenteral routes, such as intravenous (iv), intraperitoneal (ip), rectal, topical, ophthalmic, nasal, and transdermal as described in detail above.

An effective amount of fenoterol, such as (R,R)-fenoterol, or a disclosed fenoterol analogue or combination thereof will depend, at least, on the particular method of use, the subject being treated, the severity of the tumor, and the manner of administration of the therapeutic composition. A "therapeutically effective amount" of a composition is a quantity of a specified compound sufficient to achieve a desired effect in a subject being treated. For example, this may be the amount of (R,R)-fenoterol, a disclosed fenoterol analogue or a combination thereof necessary to prevent or inhibit primary brain tumor growth and/or one or more symptoms associated with the primary brain tumor in a subject. Ideally, a therapeutically effective amount of (R,R)-fenoterol or a disclosed fenoterol analogue is an amount sufficient to prevent or inhibit a tumor, such as a primary brain tumor growth and/or one or more symptoms associated with the tumor in a subject without causing a substantial cytotoxic effect on host cells.

Therapeutically effective doses of a disclosed fenoterol compound or pharmaceutical composition can be determined by one of skill in the art, with a goal of achieving concentrations that are at least as high as the $IC_{50}$ of the applicable compound disclosed in the examples herein. An example of a dosage range is from about 0.001 to about 10 mg/kg body weight orally in single or divided doses. In particular examples, a dosage range is from about 0.005 to about 5 mg/kg body weight orally in single or divided doses (assuming an average body weight of approximately 70 kg; values adjusted accordingly for persons weighing more or less than average). For oral administration, the compositions are, for example, provided in the form of a tablet containing from about 1.0 to about 50 mg of the active ingredient, particularly about 2.5 mg, about 5 mg, about 10 mg, or about 50 mg of the active ingredient for the symptomatic adjustment of the dosage to the subject being treated. In one exemplary oral dosage regimen, a tablet containing from about 1 mg to about 50 mg active ingredient is administered two to four times a day, such as two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 mg/kg to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

The specific dose level and frequency of dosage for any particular subject may be varied and will depend upon a variety of factors, including the activity of the specific compound, the metabolic stability and length of action of that compound, the age, body weight, general health, sex and diet of the subject, mode and time of administration, rate of excretion, drug combination, and severity of the condition of the subject undergoing therapy.

Selecting a Subject

Subjects can be screened prior to initiating the disclosed therapies, for example to select a subject in need of tumor inhibition, such as a subject having or at risk of developing a tumor that expresses a β2-AR. Briefly, the method can include screening subjects to determine if they are in need of tumor inhibition. Subjects having a tumor that expresses a β2-AR, such as a primary tumor, including a primary brain tumor or at risk of developing such tumor are selected. In one example, subjects are diagnosed with the tumor by clinical signs, laboratory tests, or both. For example, a tumor, such as a primary brain tumor can be diagnosed by characteristic clinical signs, such as headaches, vomiting, seizures, dizziness, weight loss and various associated complaints. Diagnosis is generally by imaging analysis such as by magnetic resonance imaging (MRI) and confirmed by histology. In some examples, a subject is selected that does not have a bleeding disorder, such as an intracerebral hemorrhage.

In an example, a subject in need of the disclosed therapies is selected by detecting a tumor expressing a β2-AR, such as by detecting β2-AR expression in a sample obtained from a subject identified as having, suspected of having or at risk of acquiring such a tumor. For example, detection of an increase, such as at least a 10% increase, including a 10%-90%, 20%-80%, 30%-70%, 40%-60%, such as a 10%, 15%, 20%, 25%, 30%, 35%, 40%, 45%, 50%, 55%, 60%, 65%, 70%, 75%, 80%, 90%, 95% increase or more in β2-AR expression as compared to β2-AR expression in the absence of a primary tumor, indicates that the tumor can be treated using the compositions and methods provided herein. In other examples, a subject is selected by detecting a primary brain tumor such as an astrocytoma or glioblastoma by MRI or positron emission tomography (PET) in a subject.

Pre-screening is not required prior to administration of the therapeutic agents disclosed herein (such as those including fenoterol, a fenoterol analogue or a combination thereof).

Exemplary Tumors

Exemplary tumors include tumors which may express a β2-AR including primary tumors, such as a primary brain tumor. A primary brain tumor includes astrocytomas, glioblastomas, ependymoma, oligodendroglomas, and mixed gliomas. Additional possible types of tumors associated with β2-AR expression include hematological tumors, such as leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of possible solid tumors which may express a β2-AR, include sarcomas and carcinomas, such as fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is a brain cancer, breast cancer or multiple myeloma that expresses a β2-AR. Tumors expressing β2-ARs can be identified by routine methods known to those of skill in the art including Western blot and histological studies with antibodies capable of detecting β2-ARs.

Assessment

Following the administration of one or more therapies, subjects having a tumor expressing a β2-AR (for example, a primary tumor) can be monitored for decreases in tumor growth, tumor volume or in one or more clinical symptoms associated with the tumor. In particular examples, subjects are analyzed one or more times, starting 7 days following treatment. Subjects can be monitored using any method known in the art including those described herein including imaging analysis.

Additional Treatments and Additional Therapeutic Agents

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least a 20%, at least a 30%, at least a 40%, at least a 50%, or at least a 70% reduction in one or more signs or symptoms associated with a tumor, such as primary brain tumor, including tumor size or volume.

In some examples, the method further includes administering a therapeutic effective amount of fenoterol, a fenoterol analogue or a combination thereof with additional therapeutic treatments. In particular examples, prior to, during, or following administration of a therapeutic amount of an agent that prevents or inhibits a tumor expressing a $\beta$2-AR, the subject can receive one or more other therapies. In one example, the subject receives one or more treatments to remove or reduce the tumor prior to administration of a therapeutic amount of a composition including fenoterol, a fenoterol analogue or combination thereof.

Examples of such therapies include, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and anti-oxidants, kinase inhibitors, and other agents. Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents (which are administered at a therapeutically effective amount) and treatments can be used alone or in combination. Methods and therapeutic dosages of such agents are known to those skilled in the art, and can be determined by a skilled clinician.

"Microtubule binding agent" refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds are of use in the methods disclosed herein: Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Examples of alkylating agents include carmustine or lomustine. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include Gleevac, Iressa, and Tarceva that prevent phosphorylation and activation of growth factors.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogues thereof.

In one example, at least a portion of the tumor (such as the primary brain tumor) is surgically removed (for example via cryotherapy), irradiated, chemically treated (for example via chemoembolization) or combinations thereof, prior to administration of the disclosed therapies (such as administration of fenoterol, a fenoterol analogue or a combination thereof). For example, a subject having a primary brain tumor associated with $\beta$2-AR expression can have at least a portion of the tumor surgically excised prior to administration of the disclosed therapies. In an example, one or more chemotherapeutic agents are administered following treatment with a composition including fenoterol, a fenoterol analogue or a combination thereof. In another particular example, the subject has a primary brain tumor and is administered radiation therapy, chemoembolization therapy, or both concurrently with the administration of the disclosed therapies.

The subject matter of the present disclosure is further illustrated by the following non-limiting Examples.

EXAMPLES

Example 1

Materials and Methods

Reagents.

Phenylmethylsulfonyl fluoride (PMSF), benzamidine, leupeptin, pepstatin A, MgCl$_2$, EDTA, Trizma-Hydrochloride (Tris-HCl), ($\pm$)-propranolol and minimal essential medium (MEM) were obtained from Sigma Aldrich (St. Louis, Mo.). Egg phosphatidylcholine lipids (PC) were obtained from Avanti Polar Lipids (Alabaster, Ala.). ($\pm$)-fenoterol was purchased from Sigma Aldrich and [$^3$H]-($\pm$)-fenoterol was acquired from Amersham Biosciences (Boston, Mass.). The organic solvents n-hexane, 2-propanol and triethylamine were obtained as ultra pure HPLC grade solvents from Carlo Erba (Milan, Italy). Fetal bovine serum and penicillin-streptomycin were purchased from Life Technologies (Gaithersburg, Md.), and [$^{125}$I]-($\pm$)-iodocyanopindolol (ICYP) was purchased from NEN Life Science Products, Inc. (Boston, Mass.).

Preparation and Identification of (R,R)-fenoterol and (S,S)-fenoterol.

(R,R)-fenoterol and (S,S)-fenoterol were prepared from (±)-fenoterol using chiral HPLC techniques employing an HPLC column (25 cm×0.46 cm i.d.) containing the amylose tris-(3,5-dimethylphenylcarbamate) chiral stationary phase (CHIRALPAK® AD CSP, Chiral Technologies, West Chester, Pa.; CHIRALPAK is a registered trademark of Daicel Chemical Industries Ltd., Exton, Pa.). The chromatographic system consisted of a JASCO® PU-980 solvent delivery system, and a JASCO® MD-910 multi-wavelength detector set at λ=230 nm, connected to a computer workstation; JASCO is a registered trademark of JASCO, Inc., Tokyo, Japan). A Rheodyne model 7125 injector with 20 μl sample loop was used to inject 0.2-0.3 mg (±)-fenoterol onto the chromatographic system. The mobile phase was n-hexane/2-propanol (88/12 v/v) with 0.1% triethylamine, the flow rate was 1 mL/minute and the temperature of the system was maintained at 25° C. using a column heater/chiller (Model 7955, Jones Chromatography Ltd., UK). The separated (R,R)-fenoterol and (S,S)-fenoterol were collected in 10-mL fractions as the respective peaks eluted from the chromatographic column. A 2-mL intermediate fraction was collected and discarded to improve the enantiomeric purity of the collected isomers.

The stereochemical configurations of the resolved (R,R)-fenoterol and (S,S)-fenoterol were established using circular dichroism (CD) measurements obtained with a JASCO® J-800 spectropolarimeter. The (R,R)-fenoterol and (S,S)-fenoterol were dissolved in 2-propanol and the measurements were obtained using 1 cm path length at room temperature.

Immobilized β2-AR Frontal Chromatography.

The liquid chromatography column containing the immobilized β2-AR was prepared using a previously described technique (Beigi et al., *Anal. Chem.*, 76: 7187-7193, 2004). In brief, cellular membranes were obtained from a HEK 293 cell line that had been transfected with cDNA encoding human β2-AR. An aliquot of a cell pellet suspension corresponding to 5-7 mg total protein, as determined by the micro BCA method, was used to create the column. The membranes were prepared in 10 mL buffer composed of Tris-HCl [50 mM, pH 7.4] containing $MgCl_2$ (2 mM), benzamidine (1 mM), leupeptin (0.03 mM) pepstatin A (0.005 mM) and EDTA (1 mM).

A 180 mg aliquot of immobilized artificial membrane chromatographic support (IAM-PC, 12 micron particle size, 300 Å pore size obtained from Regis Chemical Co., Morton Grove, Ill.) and 80 μM PC were added to the membrane preparation and the resulting mixture was stirred at room temperature for 3 hours, transferred into (5 cm length) nitrocellulose dialysis membrane (MW cutoff 10,000 Da, Pierce Chemical, Rockford, Ill.) and placed in 1 L of dialysis buffer composed of Tris-HCl [50 mM, pH 7.4] containing EDTA (1 mM), $MgCl_2$ (2 mM), NaCl (300 mM) and PMSF (0.2 mM) at 4° C. for 24 hours. The dialysis step was repeated twice using fresh buffer.

After dialysis, the mixture was centrifuged at 120×g for 3 minutes, the supernatant was discarded and the pellet of IAM support containing the immobilized receptor-bearing membranes was collected. The pellet was resuspended in 2 mL chromatographic running buffer, composed of Tris-HCl [10 mM, pH 7.4] containing EDTA (1 mM) and $MgCl_2$ (2 mM) and the suspension was pumped through a HR 5/2 chromatographic glass column (Amersham Pharmacia Biotech, Uppsala, Sweden) at a flow rate of 0.3 mL/minutes using a peristaltic pump. The end adaptors were assembled producing a total gel-bed volume of 0.4 mL. The column was stored at 4° C. when not in use.

The column containing the immobilized β2-AR stationary phase was placed in a chromatographic system composed of a HPLC pump (10-AD, Shimadzu Inc., Columbia, Md.), a manually controlled FPLC injector (Amersham Biotechnology, Uppsala, Sweden) with a 504 sample loop, the packed immobilized receptor column and an on-line radioactive flow detector (IN/US, Tampa, Fla.), all connected sequentially. In the frontal chromatographic studies, sample volumes of 5-7 mL were applied continuously until the elution profile showed a plateau region. The running buffer was composed of Tris-HCl [10 mM, pH 7.4] containing EDTA (1 mM) and $MgCl_2$ (2 mM) and 0.05 nM [$^3$H]-(±)-fenoterol, the marker ligand. (R,R)-fenoterol or (S,S)-fenoterol was added to the running buffer in sequential concentrations of 0.1, 80.0, 240, and 700 nM, and applied to the column. The immobilized receptor column was equilibrated with about 80 mL of running buffer, without the added (R,R)-fenoterol or (S,S)-fenoterol respectively, in between each sample injection. All chromatographic studies were carried out at room temperature at a flow rate of 0.2 mL/minutes.

The data were analyzed to determine the number of binding sites and dissociation constant using the non-linear equation (1), $$[M](Vi - V\min) = \frac{P[M]}{Kd + [M]} \quad \text{(Eq. 1)}$$

where $V_i$ is the solute elution volume, $V_{min}$ is the elution volume at the saturation point, P is the number of available binding sites, M is the concentration of the marker ligand and $K_d$ is the dissociation constant of the ligand.

Ligand-Displacement Binding.

Twenty-four hours after adenoviral infection with human β2-AR, HEK293 cells were harvested in lysis buffer, Tris-HCl [5 mM, pH 7.4] containing EGTA [5 mM], and homogenized with 15 strokes on ice. Samples were centrifuged at 30,000×g for 15 minutes to pellet membranes. Membranes were resuspended in binding buffer, Tris-HCl [20 mM, pH 7.4] containing NaCl (120 mM), KCl (5.4 mM), $CaCl_2$ (1.8 mM), $MgCl_2$ (0.8 mM), and glucose (5 mM) and stored in aliquots at −80° C. Binding assays were performed on 5-10 μg of membrane protein using saturating amounts (1-300 pM) of the β-AR-specific ligand [$^{125}$I]cyanopindolol (ICYP). For competition binding, the 5-10 μg of membrane protein were pretreated with 50 μM of $GTP_{\gamma s}$ (non-hydrolyzable guanosine triphosphate) and then incubated with $^{125}$ICYP (50 pM) and different concentrations of fenoterol or its isomers in a total volume of 250 μL. Nonspecific binding was determined in the presence of 20 μM propranolol. Reactions were conducted in 250 μL of binding buffer at 37° C. for 1 hour. The binding reaction was terminated by addition of ice-cold Tris-HCl [10 mM, pH 7.4] to the membrane suspension, followed by rapid vacuum filtration through glass-fiber filters (Whatman GF/C). Each filter was washed three times with an additional 7 mL of ice-cold Tris-HCl [10 mM, pH 7.4]. The radioactivity of the wet filters was determined in a gamma counter. All assays were performed in duplicate, and receptor density was normalized to milligrams of membrane protein. $K_d$ and the maximal number of binding sites ($B_{max}$) for ICYP were determined by Scatchard analysis of saturation binding isotherms. Data from competition studies were analyzed using 1- or 2-site competition binding curves with GRAPH- PAD PRISM® Software (GRAPHPAD PRISM is a registered trademark of GraphPad Software, Inc., San Diego, Calif.).

Example 2

Purification and Identification of (R,R)-fenoterol and (S,S)-fenoterol

This example demonstrates the resolution of (R,R)-fenoterol and (S,S)-fenoterol from (±)-fenoterol to a high degree of enantiomeric purity.

Using the chromatographic conditions described in Example 1, (±)-fenoterol was separated into its component enantiomers, (R,R)-fenoterol and (S,S)-fenoterol, on the AD-CSP. As illustrated in FIG. 1, the two stereoisomers were resolved with enantioselectivity factor ($\alpha$) of 1.21 and a resolution factor ($R_S$) of 1.06. Because of the observed tailing of the chromatographic peaks, a 2-mL intermediate fraction was collected and discarded. The collected peaks were analyzed using the same chromatographic conditions and the data demonstrated that both enantiomers had been prepared with >97% stereochemical purity.

Figure 2B:
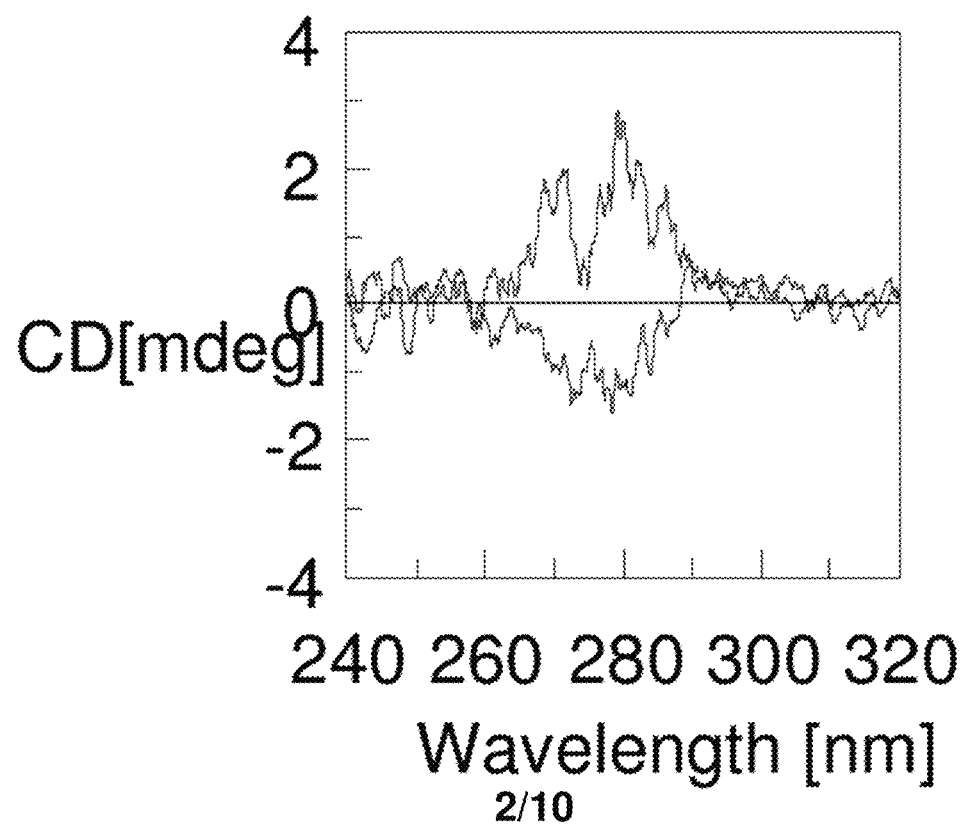
FIG. 2B illustrates a circular dichroism spectra of (R,R)- and (S,S)-fenoterol.

The assignment of the absolute configuration of the isolated fractions was accomplished using their chiroptical properties. The ultraviolet (UV) spectra of both fractions contained identical maxima at about 280 and 230, indicating the same UV chromophores for the two enantiomers. The circular dichroism (CD) spectrum shows, for the less retained enantiomeric fraction, negative CD bands at about 280 and 215 nm, while the spectrum is positive at 230 and 200 nm. The sign of the CD bands is reversed for the most retained fenoterol fraction, this confirming the enantiomeric nature of the two fractions. The lowest energy UV and CD spectra of the two enantiomeric fractions are presented in FIGS. 2A and 2B, respectively. The less retained chromatographic fraction showed a negative CD band at about 280 nm, while the CD spectrum of the most retained chromatographic fraction contained a positive CD band at the same wavelength (FIG. 2B). These results indicate that each of the fractions contained one of the fenoterol enantiomers.

The sign of the lowest energy CD band can be used to assign the absolute configuration of the separated fenoterol enantiomers, by applying the Brewster-Buta/Smith-Fontana sector rule for chiral benzylic derivatives (Brewster and Buta, *J. Am. Chem. Soc.*, 88: 2233-2240, 1996). This sector rule is used to predict the sign of the CD band related to the $^1L_b$ electronic transition of the benzylic compounds, with either hydroxyl or amine moieties and has been primarily applied to conformationally mobile aromatic compounds containing a single stereogenic center. In the case of fenoterol, there are two stereogenic centers. However, it is believed that the observed optical activity is mainly determined by the arylcarbinol moiety, because of the distance between the aromatic ring and the stereogenic center. The application of this rule permitted the assignment of the absolute configuration of (S,S) to the fenoterol enantiomer contained in the less retained fraction that showed a negative CD band at 280 nm, and the absolute configuration of (R,R) to the fenoterol enantiomer contained in the most retained fraction that showed a positive CD band at 280 nm. This assignment was confirmed by the independent synthesis of (S,S)-fenoterol and (R,R)-fenoterol.

These studies indicate that (R,R)-fenoterol and (S,S)-fenoterol can be separated from (±)-fenoterol to a high degree of enantiomeric purity.

Example 3

Chromatographic Determination of the Binding of (R,R)-fenoterol and (S,S)-fenoterol to the Immobilized β2-AR This example demonstrates that (R,R)-fenoterol is responsible for the β2-AR binding of the clinically used drug (±)-fenoterol.

The preparation, characterization and application of a liquid chromatographic stationary phase containing immobilized membranes obtained from the β2-AR HEK-293 cell line have been previously reported (Beigi et al., *Anal. Chem.*, 76: 7187-7193, 2004). For example, Beigi et al. (*Anal. Chem.*, 76: 7187-7193, 2004) demonstrated that frontal displacement chromatography could be used to determine the dissociation constants ($K_d$) for the binding of two β2-AR antagonists, (S)-propranolol and CGP 12177A, to the immobilized β2-AR. Zonal displacement chromatography using CGP 12177A as the marker ligand demonstrated that the immobilized β2-AR had retained its enantioselectivity as the addition of (S)-propranolol to the mobile phase produced a greater displacement than the addition of (R)-propranolol (Id.). The addition of (±)-fenoterol to the mobile phase was also shown to produce a conformation change in the immobilized β2-AR (Id.). Agonist-induced conformational changes of the β2-AR, as well as most G-protein coupled receptors, from a resting to active state have been documented (Ghanoui et al., *Proc. Natl. Acad. Sci. U.S.A.*, 98: 5997-6002, 2001).

Presently, the immobilized β2-AR column was equilibrated with the running buffer containing the [$^3$H]-fenoterol, the marker ligand, before the initiation of the displacement studies. It was assumed that the binding data calculated using frontal displacement chromatography reflects the binding of (R,R)-fenoterol and (S,S)-fenoterol to the active state of the receptor. In frontal chromatography, the initial flat portion of the chromatographic trace represents the binding of a marker ligand that is specific for the immobilized target, in this study the β2-AR, as well as nonspecific binding to other sites on the immobilized membrane fragments. Saturation of specific binding sites produces a breakthrough front followed by a plateau representing the establishment of a new equilibrium. The addition of a second compound into the mobile phase will produce a shift of the chromatographic trace to the left if the compound competes with the marker for binding to the β2-AR. The relationship between the magnitude of this shift and the concentration of the marker ligand can be used to calculate the binding affinity of the displacer for the target and the number of active binding sites (Moaddel and Wainer, *Anal. Chem. Acata*, 546: 97-105, 2006).

Figure 3:
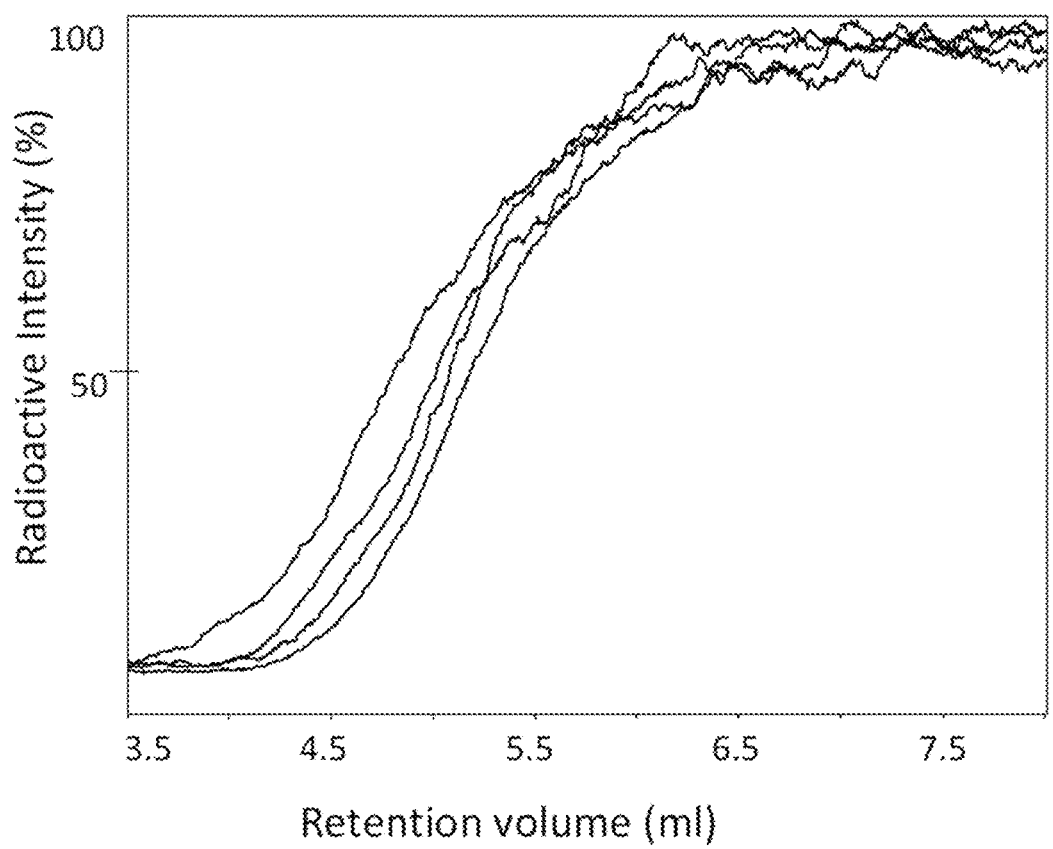
FIG. 3 provides frontal chromatographic elution profiles of [$^+$H]-(±)-fenoterol produced by the addition of (R,R)-fenoterol to the running buffer.

As shown in FIG. 3 (curve 1), the addition of [$^3$H]-fenoterol to the running buffer produced the expected frontal chromatography trace. Sequential addition of increasing concentrations of (R,R)-fenoterol to the running buffer produced a corresponding shift in the chromatographic traces towards smaller retention volumes (FIG. 3, curves 2-4). The magnitude and the shift and the corresponding concentrations of (R,R)-fenoterol were analyzed using Eqn 1 and the calculated dissociation constant, $K_d$, was 472 nM and the amount of available binding sites [P] was 176 pmoles per column, $r^2$=0.9999 (n=2).

The sequential addition of increasing concentrations of (S,S)-fenoterol to the running buffer produced no corresponding shift in the chromatographic traces toward shorter retention times. Thus, (S,S)-fenoterol had no significant affinity for the immobilized β2-AR.

In order to validate the chromatographic results, a standard membrane binding study was conducted using membranes obtained from the same HEK-293 cell line used to create the immobilized β2-AR column. The data reflected the presence of a single binding site with (mean±SD) $K_d$=457±55 nM (n=4) for (R,R)-fenoterol and 109,000±10, 400 nM (n=4) for (S,S)-fenoterol. These data indicate that frontal affinity chromatography on immobilized cellular membrane columns can be used to determine the magnitude and enantioselectivity of ligand binding to the target receptor. Further, the results from the frontal affinity chromatography and ligand competition binding studies both demonstrate that (R,R)-fenoterol is responsible for the β2-AR binding of the clinically used drug (±)-fenoterol.

Example 4

Synthesis

General Procedures

All reactions were carried out using commercial grade reagents and solvents. Tetrahydrofuran (THF) was dried by refluxing over sodium and benzophenone. Dichloromethane was dried by refluxing over calcium hydride. Ultraviolet spectra were recorded on a Cary 50 Concentration spectrophotometer. Optical rotations were done on a Rudolph Research Autopol IV. NMR Spectra were recorded on a Varian Mercury VMX 300-MHz spectrophotometer using tetramethylsilane as the internal standard. NMR multiplicities were reported by using the following abbreviations: s, singlet; d, doublet; t, triplet; q, quartet; p, pentet; m, multiplet; apt., apparent; and br, broad. Low resolution mass spectra were obtained on a Finnigan LCQ$^{Duo}$ LC MS/MS atmospheric pressure chemical ionization (API) quadrupole ion trap MS system equipped with both electrospray (ESI) and atmospheric pressure chemical ionization (APCI) probes. Analytical HPLC data was obtained using a Waters 2690 Separations Module with PDA detection. Method (a): ThermoHypersil BDS 100×4.6 mm C18 column, H$_2$O/CH$_3$CN/TFA. Method (b): Brownlee Phenyl Spheri-5 100×4.6 mm, water/acetonitrile/TFA. Method (c): Vydac 150×4 mm C18 column, H$_2$O/isopropanol/TFA. Method (d): CHIRALPAK® AD-H 250×10 mm, 95/5/0.05 CH$_3$CN/isopropanol/diethylamine. Merck silica gel (230-400 mesh) was used for open column chromatography.

3',5'-Dibenzyloxy-α-bromoacetophenone (46)

A solution of 2.4 mL (46 mmol) of Br$_2$ in 45 mL of CHCl$_3$ was added dropwise over 1 h to a chilled, stirring solution of 9.66 g (29 mmol) of 3',5'-dibenzyloxyacetophenone (45) in 40 mL of CHCl$_3$. The resulting solution was allowed to warm to room temperature over 1 hour with good stirring, then poured into 100 mL of cold H$_2$O and transferred to a separatory funnel where the CHCl$_3$ fraction was isolated, washed with brine solution, dried (Na$_2$SO$_4$), filtered, and concentrated to 10.8 g. This material was applied to 500 g of silica gel, eluting with CHCl$_3$ to obtain 2.65 g (22%) of compound 46 as a white solid. $^1$H NMR (CDCl$_3$) δ 4.39 (s, 2H), 5.08 (s, 4H), 6.85 (t, 1H, J=2.1 Hz), 7.20 (d, 2H, J=2.4 Hz), 7.31-7.44 (m, 10H).

General Procedure for the Enantioselective Reduction of Compound 46 to 3',5'-Dibenzyloxyphenylbromohydrins [(R)-8, (S)-8]

Under argon atmosphere, ~0.06 mL (0.316 mmol, 10 mol %) of 5.0 M boron-methyl sulfide complex (BH$_3$SCH$_3$) in diethyl ether was added in one portion to a solution of 25 mg (0.16 mmol, 5 mol %) of the appropriate cis-1-amino-2-indanol in 3 mL of dry THF. This material under argon was added over 30 minutes to a solution of 1.3 g (3.16 mmol) of 3',5'-dibenzyloxy-α-bromoacetophenone in 20 mL of dry THF, while at the same time adding in ~0.05 mL, pulses, 0.45 mL of 5.0 M boron-methyl sulfide complex. The resulting solution was stirred under argon for 2 hours, and then quenched with 3 mL of methanol, controlling gas evolution. Solvents were removed in vacuo and the resulting residue taken up in 30 mL of CHCl$_3$ and washed with 25 mL of 0.2 M sulfuric acid followed by 20 mL of brine, then dried (Na$_2$SO$_4$), filtered, and evaporated.

(R)-(−)-3',5'-Dibenzyloxyphenylbromohydrin [(R)-8]

Prepared with (1R, 2S)-(+)-cis-1-amino-2-indanol as the enantioselective reduction catalyst to give 1.02 g (78%) of (R)-8 as a fine white powder. $^1$H NMR (CDCl$_3$) δ 3.44 (dd, 1H, J=9.0, 10.5 Hz), 3.55 (dd, 1H, J=3.3, 10.5 Hz), 4.79 (dd, 1H, J=3.3, 8.7 Hz), 4.97 (s, 4H), 6.51 (t, 1H, J=2.4 Hz), 6.57 (d, 2H, J=1.8 Hz), 7.21-7.38 (m, 10H); [α]$_D$=−12.1° (c=1.0 MeOH).

(S)-(+)-3',5'-Dibenzyloxyphenylbromohydrin [(S)-8]

Prepared with (1S, 2R)-(−)-cis-1-amino-2-indanol as the enantioselective reduction catalyst to give 1.07 g (82%) of (S)-8 as a fine white powder. $^1$H NMR (CDCl$_3$) δ 3.43 (dd, 1H, J=9.0, 10.5 Hz), 3.55 (dd, 1H, J=3.3, 10.5 Hz), 4.78 (dd, 1H, J=3.3, 8.7 Hz), 4.96 (s, 4H), 6.50 (t, 1H, J=2.4 Hz), 6.57 (d, 2H, J=1.8 Hz), 7.21-7.39 (m, 10H); [α]$_D$=+11.8° (c=0.90 MeOH).

4-Benzyloxyphenylacetone (34)

To 10.0 g (41.3 mmol) of 4-benzyloxyphenylacetic acid (31) was added, 20 mL of acetic anhydride and 20 mL of pyridine, which was heated to reflux with stirring under argon atmosphere for 6 hours. Solvents were evaporated and residue dissolved in CHCl$_3$ (50 mL) and washed with 1N NaOH (2×50 mL). Dried organic layer (MgSO$_4$), filtered, and evaporated to 11.8 g of an amber oil. Vacuum distillation at 0.1 mm Hg in an oil-bath set to 170° C. followed by silica gel chromatography eluting with 8/2 CH$_2$Cl$_2$-hexanes gave 2.68 g (27%). $^1$H NMR (CDCl$_3$) δ 2.14 (s, 3H), 3.63 (s, 2H), 5.05 (s, 2H), 6.94 (d, 2H, J=8.7 Hz), 7.10 (d, 2H, J=8.7 Hz), 7.26-7.47 (m, 5H).

Phenylacetone (35)

A solution of 20.4 g (0.15 mol) of phenylacetic acid, acetic anhydride (70 mL) and pyridine (70 mL) was heated to reflux with stirring under argon atmosphere for 6 hours. Solvents were evaporated and residue dissolved in CHCl$_3$ (100 mL), washed with 1N NaOH (2×100 mL) and dried the organic layer (MgSO$_4$), filtered, and evaporated to give 20.4 g. Vacuum distillation at 0.1 mm Hg in an oil bath set to 160° C., followed by silica gel chromatography eluting with 1/1 hexanes/CH$_2$Cl$_2$ gave 5.5 g (27%). $^1$H (CDCl$_3$) δ 2.15 (s, 3H), 3.70 (s, 2H), 7.20-7.36 (m, 5H).

1-Naphthalen-1-yl-propan-2-one (36)

A solution of 37.2 g (20 mmol) of naphthoic acid (33), acetic anhydride (100 mL) and pyridine (100 mL) was heated to reflux with stirring under argon atmosphere for 6 hours. Evaporated solvents, dissolved residue in CHCl$_3$ (200 mL) and washed with 1N NaOH (2×150 mL), dried organic layer (MgSO$_4$), filtered, and evaporated to give 34.6 g. Distillation at 0.5 mm Hg in an oil bath set to 170° C., followed silica gel chromatography eluting with 1/1 hexanes/CH$_2$Cl$_2$ gave 9.7 g (26%). $^1$H (CDCl$_3$) δ 2.11 (s, 3H), 4.12 (s, 2H), 7.40-7.53 (m, 4H), 7.81 (d, 1H, J=8.4 Hz), 7.87-7.90 (m, 2H).

General Procedure for Preparation of 2-benzylaminopropanes (37-39, 42, 43)

To the appropriate ketone (1 eq) in CH$_2$Cl$_2$ (c=0.5 M), cooled to 0° C. was added glacial HOAc (1 eq), followed by benzylamine (1 eq) and NaBH(AcO)$_3$ (1.4 eq). The reaction mixture was warmed to room temperature and stirred under argon for 20 hours. The reaction mixture was cooled (ice bath), 10% NaOH (5 eq) was added dropwise and then extracted into CH$_2$Cl$_2$, washed with brine. The product was then dried (Na$_2$SO$_4$), filtered and evaporated.

1-(4-benzyloxy)-2-benzylaminopropane (37)

Prepared from 4-benzyloxy-phenylacetone (34; 2.0 g, 8.3 mmol) to afford 2.61 g (95%) as a tan solid. $^1$H (CDCl$_3$) δ 1.10 (d, 3H, J=6.3 Hz), 2.50-2.58 (m, 1H). 2.68-2.77 (m, 1H), 2.82-2.89 (m, 1H), 3.75 (dd, 2H, J=12 Hz, J=30 Hz), 5.05 (s, 2H), 6.90 (d, 2H, J=8.7 Hz), 7.04 (d, 2H, J=8.7 Hz), 7.17-7.42 (m, 10H); MS (APCI+) m/z (rel): 332 (100).

1-Phenyl-2-benzylaminopropane (38)

Prepared from phenylacetone (35; 5.5 g, 41 mmol) to afford 8.4 g (91%) as a tan solid. $^1$H (CDCl$_3$) δ 1.09 (d, 3H, J=6.3 Hz), 2.61-2.81 (m, 2H), 2.92 (m, 1H), 3.80 (dd, 2H), 7.14-7.30 (m, 10H); MS (APCI+) m/z (rel): 226 (100).

1-(1'-Naphthyl)-2-benzylaminopropane (39)

Prepared from 1-naphthalen-1-yl-propan-2-one (36; 5.0 g, 27.1 mmol) to afford 7.0 g (94%) as a tan solid. $^1$H (CDCl$_3$) δ 1.14 (d, 3H, J=6.0 Hz), 3.02-3.18 (m, 2H), 3.27 (m, 1H), 3.80 (dd, 2H, J=13.2, 43.8 Hz), 7.13-7.23 (m, 5H), 7.31-7.48 (m, 4H), 7.73 (d, 1H, J=7.8 Hz), 7.83-7.86 (m, 1H), 7.96-7.99 (m, 1H); MS (APCI+) m/z (rel): 276 (100).

1-(4'-Methoxyphenyl)-2-benzylaminopropane (42)

Prepared from 4-methoxyphenyl-acetone (40; 2.75 g, 13.1 mmol) to afford 2.31 g (97%). $^1$H (CDCl$_3$) δ 1.10 (d, 3H, J=6.3 Hz), 2.56-2.75 (m, 2H), 2.90 (m, 1H), 3.79 (s, 1H), 3.79 (m, 2H, J=13.2 Hz), 6.82 (d, 2H, J=8.7 Hz), 7.07 (d, 2H, J=8.7 Hz), 7.18-7.32 (m, 5H); MS (APCI+) m/z (rel): 256 (100).

1-(4'-nitrophenyl)-2-benzylaminopropane (43)

Prepared from 4-nitrophenyl-acetone (41; 4.95 g, 28 mmol) to afford 7.32 g (98%) as an amber oil. $^1$H (CDCl$_3$) δ 1.60 (d, 3H, J=6.3 Hz), 2.73-2.85 (m, 1H), 3.00-3.12 (m, 2H), 3.86 (dd, 2H, J=26 Hz, J=60 Hz), 7.23-7.40 (m, 5H), 7.30 (d, 2H, J=9.0 Hz), 8.14 (d, 2H, J=8.7 Hz). MS (APCI+) m/z (rel): 271 (100).

General Procedure for Enantiomeric Separation of 2-benzylaminopropanes {(R)-10-14, (S)-10-14}

The appropriate racemic 2-benzylaminopropane (1 eq) was combined with the appropriate optically active mandelic acid (1 eq) in methanol (c=0.5 M) and refluxed until the solution homogenized, then cooled to RT. The crystals were filtered, collected, and recrystallized twice from methanol (c=0.3 M) to afford the optically active 2-benzylaminopropane.mandelic acid salt. The salts were converted to the free amine for the purpose of collecting NMR and rotation data by partitioning the mandelic acid salt between 10% K$_2$CO$_3$ and CHCl$_3$, drying organic extracts (Na$_2$SO$_4$) and evaporating.

(R)-(−)-1-(4'-benzyloxy)-2-benzylaminopropane {(R)-10}

A sample of 2.13 g (6.42 mmol) of 1-(4-benzyloxy)-2-benzylaminopropane (37) was reacted with 972 mg (6.42 mmol) of (R)-(−)-mandelic acid to give 295 mg (28% based on enantiomeric abundance) of the free amine after workup. $^1$H NMR (CDCl$_3$) δ 1.12 (d, 3H, J=6.3 Hz), 2.58-2.78 (m, 2H), 2.82-2.91 (m, 1H), 3.75 (dd, 2H, J=12 Hz, J=30 Hz)), 5.07 (s, 2H), 6.93 (d, 2H, J=8.7 Hz), 7.10 (d, 2H, J=8.7 Hz), 7.21-7.42 (m, 10H); MS (APCI+) m/z (rel): 332 (100); [α]$_D$=−19.1° (c=1.4, MeOH).

(S)-(+)-1-(4'-benzyloxy)-2-benzylaminopropane {(S)-10}

The washes from the separation of (R)-10 were concentrated and partitioned between 50 mL of chloroform and 50 mL of 10% K$_2$CO$_3$ in water. Washed organics with brine, dried (Na$_2$SO$_4$), filtered and evaporated to 1.70 g (5.1 mmol). The organics were brought to reflux with 782 mg (5.1 mmol) of (S)-(+)-mandelic acid (as previously described) and crystallized 3 times to obtain 670 mg of the (S)-amine.(S)-mandelic acid salt. The (S)-amine.(S)-mandelic acid salt was triturated in ether then partitioned between 30 mL of chloroform and 20 mL of 10% K$_2$CO$_3$ in water. The organic partition was washed with brine, then dried (Na$_2$SO$_4$), filtered and evaporated to give 366 mg of the free amine (33% based on enantiomeric abundance). $^1$H NMR (CDCl$_3$) δ 1.10 (d, 3H, J=6.3 Hz), 2.58-2.78 (m, 2H), 2.82-2.91 (m, 1H), 3.76 (dd, 2H, J=12, 30 Hz), 5.06 (s, 2H), 6.93 (d, 2H, J=8.7 Hz), 7.09 (d, 2H, J=8.7 Hz), 7.21-7.42 (m, 10H); MS (APCI+) m/z (rel): 332 (100); [α]$_D$=+19.2° (c=1.5 MeOH).

(R)-(−)-1-(4'-Methoxyphenyl)-2-benzylaminopropane [(R)-11]

A sample of 3.02 g (11.8 mmol) of 1-(4'-methoxyphenyl)-2-benzylaminopropane (42) was reacted with 1.8 g (11.8 mmol) (S)-(+)-mandelic acid to give 530 mg (35% based on enantiomeric abundance) of the free amine after workup. $^1$H NMR (CDCl$_3$) δ 1.10 (d, 3H, J=6.3 Hz), 2.57-2.76 (m, 2H), 2.88-2.94 (m, 1H), 3.79 (s, 3H), 3.72-3.88 (m, 2H), 6.82 (d, 2H, J=8.7 Hz), 7.07 (d, 2H, J=8.4 Hz), 7.15-7.31 (m, 5H); MS (APCI+) m/z (rel): 256 (100); [α]$_D$=−30.4° (c=1.25 MeOH).

(S)-(+)-1-(4'-Methoxyphenyl)-2-benzylaminopropane {(S)-11}

A sample of 3.36 g (13.2 mmol) of the racemate 1-(4'-methoxyphenyl)-2-benzylaminopropane (42) was reacted with 2.0 g (13.2 mmol) of (R)-(−)-mandelic acid to give 740 mg (44% based on enantiomeric abundance) of the free amine after workup. $^1$H NMR, (CDCl$_3$) δ 1.10 (d, 3H, J=6.2 Hz), 2.55-2.76 (m, 2H), 2.88-2.95 (m, 1H), 3.73-3.88 (m, 2H), 3.79 (s, 3H), 6.80 (d, 2H, J=8.7 Hz), 7.08 (d, 2H, J=8.4 Hz), 7.15-7.30 (m, 5H); MS (APCI+) m/z (rel): 256 (100); $[\alpha]_D$=+30.5° (c=1.1 MeOH).

(R)-(−)-1-(4'-nitrophenyl)-2-benzylaminopropane {(R)-12}

A sample of 2.0 g (7.3 mmol) of 1-(4'-nitrophenyl)-2-benzylaminopropane (43) was reacted with 1.13 g (7.3 mmol) of (S)-(+)-mandelic acid to give 486 mg (49% based on enantiomeric abundance) of the free amine after workup. $^1$H NMR (CDCl$_3$) δ 1.60 (d, 3H, J=6.3 Hz), 2.73-2.85 (m, 1H), 3.00-3.12 (m, 2H), 3.86 (dd, 2H, J=26 Hz, J=60 Hz), 7.23-7.40 (m, 5H), 7.30 (d, 2H, J=9.0 Hz), 8.14 (d, 2H, J=8.7 Hz); MS (APCI+) m/z (rel): 271 (100); $[\alpha]_D$=−9.3° (c=1.0 MeOH).

(S)-(+)-1-(4'-nitrophenyl)-2-benzylaminopropane [(S)-12]

A sample of 2.0 g (7.3 mmol) of 1-(4'-nitrophenyl)-2-benzylaminopropane (43) was reacted with 1.13 g (7.3 mmol) of (R)-(−)-mandelic acid to give 640 mg (65% based on enantiomeric abundance) of the free amine after workup. $^1$H NMR (CDCl$_3$) δ☐ 1.60 (d, 3H, J=6.3 Hz), 2.73-2.85 (m, 1H), 3.00-3.12 (m, 2H), 3.86 (dd, 2H, J=26, 60 Hz), 7.23-7.40 (m, 5H), 7.30 (d, 2H, J=9.0 Hz), 8.14 (d, 2H, J=8.7 Hz); MS (APCI+) m/z (rel): 271 (100); $[\alpha]_D$=+8.2° (c=1.0 MeOH).

(R)-(−)-1-Phenyl-2-benzylaminopropane [(R)-13]

A sample of 2.62 g (11.6 mmol) of 1-phenyl-2-benzylaminopropane (38) was reacted with 1.77 g (11.6 mmol) of (S)-(+)-mandelic acid to give 747 mg (57% based on enantiomeric abundance) of the free amine after workup. $^1$H NMR (CDCl$_3$) δ 1.13 (d, 3H, J=6.0 Hz), 2.62-2.84 (m, 2H), 2.92-2.99 (m, 1H), 3.81 (dd, 2H, J=13.2, 34.5 Hz) 7.14-7.29 (m, 10H); MS (APCI+) m/z (rel): 226 (100); $[\alpha]_D$=−24.5° (c=1.10 MeOH).

(S)-(+)-1-Phenyl-2-benzylaminopropane [(S)-13]

A sample of 5.0 g (22.2 mmol) of racemic 1-phenyl-2-benzylaminopropane (38) was reacted with 3.4 g (22.2 mmol) of (R)-(−)-mandelic acid to give 2.15 g (86% based on enantiomeric abundance) of the free amine after workup. $^1$H NMR (CDCl$_3$) δ 1.11 (d, 3H, J=6.0 Hz), 2.62-2.84 (m, 2H), 2.92-2.99 (m, 1H), 3.81 (dd, 2H, J=13.2, 34.5 Hz), 7.14-7.29 (m, 5H); MS (APCI+) m/z (rel): 226 (100); $[\alpha]_D$=+18.2° (c=0.85 MeOH).

(R)-(−)-1-(1'-Naphthyl)-2-benzylaminopropane [(R)-14]

The washes recovered from the separation of (S)-14 were concentrated and partitioned between 40 mL of chloroform and 40 mL of 10% K$_2$CO$_3$ in water. The organic partition was washed with 20 mL of brine then dried (Na$_2$SO$_4$) to afford 1.16 g (4.2 mmol) of the free amine, which was reacted with 640 mg (4.2 mmol) of (S)-(+)-mandelic acid. 588 mg (46% based on enantiomeric abundance) of the free amine was obtained. $^1$H NMR (CDCl$_3$) δ 1.07 (d, 3H, J=6.0 Hz), 3.02-3.18 (m, 2H), 3.27 (m, 1H), 3.74 (dd, 2H, J=13.2, 30.9 Hz), 7.13-7.23 (m, 5H), 7.31-7.48 (m, 4H), 7.73 (d, 1H, J=7.8 Hz), 7.83-7.86 (m, 1H), 7.96-7.99 (m, 1H); MS (APCI+) m/z (rel): 276 (100); $[\alpha]_D$=−5.8° (c=1.0 MeOH).

(S)-(+)-1-(1'-Naphthyl)-2-benzylaminopropane [(S)-14]

A sample of 2.6 g (9.4 mmol) of 1-(1'-naphthyl)-2-benzylaminopropane (39) was reacted with 1.44 g (9.4 mmol) of (R)-(−)-mandelic acid to give 420 mg (21% based on enantiomeric abundance) of the free amine after workup. $^1$H NMR (CDCl$_3$) δ 1.07 (d, 3H, J=6.0 Hz), 3.02-3.18 (m, 2H), 3.27 (m, 1H), 3.74 (dd, 2H, J=13.2, 30.9 Hz), 7.13-7.23 (m, 5H), 7.31-7.48 (m, 4H), 7.73 (d, 1H, J=7.8 Hz), 7.83-7.86 (m, 1H), 7.96-7.99 (m, 1H); MS (APCI+) m/z (rel): 276 (100); $[\alpha]_D$=+6.3° (c=1.0 MeOH).

(R)-(−)-2-Benzylaminoheptane [(R)-15]

A sample of 0.65 mL (4.4 mmol) of (R)-(−)-2-aminoheptane (R-44) 0.44 mL (4.4 mmol) of benzaldehyde and 0.1 mL of HOAc were combined in 40 mL of CH$_2$Cl$_2$ and then cooled to 0° C. To the reaction mixture was added 2.75 mg (13 mmol) of sodium triacetoxyborohydride in one portion, which was stirred under argon at room temperature for 28 hours. The reaction mixture was diluted with 30 mL of CH$_2$Cl$_2$, cooled in an ice bath and 80 mL of 5% NaOH (in water) was added. Fractions were separated, organics (Na$_2$SO$_4$) dried and evaporated to 638 mg (71%) of (R)-15. $^1$H NMR (CDCl$_3$) δ 0.88 (m, 3H), 1.08 (d, 3H J=6.6 Hz), 1.20-1.39 (m, 6H), 1.41-1.67 (m, 2H), 3.62-3.77 (m, 1H), 3.75 (p, 2H, J=12 Hz), 7.17-7.41 (m, 5H); MS (APCI+) m/z (rel): 206 (100); $[\alpha]_D$=+6.9° (c=1.0, MeOH).

(S)-(+)-2-Benzylaminoheptane [(S)-15]

A sample of 0.15 mL (1 mmol) of (S)-(+)-2-aminoheptane ((S)-44) 0.1 mL (1 mmol) of benzaldehyde and 0.1 mL of HOAc were combined in 10 mL of CH$_2$Cl$_2$ and cooled to 0° C., then added 650 mg (3 mmol) of sodium triacetoxyborohydride in one portion. The reaction mixture was stirred under argon at room temperature for 28 hours. The mixture was diluted with 10 mL of dichloromethane, cooled in an ice bath and 20 mL of 5% NaOH (in water) was added. Fractions were separated, organics were dried (Na$_2$SO$_4$) and evaporated to 154 mg (70%). $^1$H NMR (CDCl$_3$) δ 0.88 (m, 3H), 1.08 (d, 3H J=6.6 Hz), 1.19-1.37 (m, 6H), 1.41-1.67 (m, 2H), 3.62-3.77 (m, 1H), 3.75 (p, 2H, J=12 Hz), 7.17-7.41 (m, 5H); MS (APCI+) m/z (rel): 206 (100); $[\alpha]_D$=+7.8° (c=1.0, MeOH).

Preparation of Fenoterol Analogs, Procedure A

To form the epoxide, the appropriate 3',5'-dibenzyloxy-phenylbromohydrin ((R)-8) or (S)-8 (1 eq) was combined with K$_2$CO$_3$ (1.4 eq) in 1:1 THF/MeOH (c=0.3 M) and stirred for 2 hours under argon at room temperature. The solvent was removed and the residue partitioned between toluene and H$_2$O. The toluene fraction was isolated, dried (Na$_2$SO$_4$), filtered, and evaporated. The residue was dissolved with the appropriate free benzylamine (R)- or (S)-10-15, 28 (0.95 eq) in a good amount of toluene and evaporated again under high vacuum to remove trace H$_2$O. The resulting colorless residue was heated to 120° C. under argon for 20 hours, cooled and checked by $^1$H NMR and mass spectrometry to confirm coupling. The residue was dissolved in EtOH (c=0.07 M) with heat and transferred to a Parr flask, where it was hydrogenated at 50 psi of hydrogen over 10% (wt) Pd/C (10 mg cat/65 mg bromohydrin) for 24 hours. Complete debenzylation was confirmed by mass spectrometry. The mixture was filtered through Celite, the filter cake rinsed with isopropanol, and the filtrate concentrated. The residue was dissolved in 1:1 isopropanol/EtOH (c=0.2 M) and brought to reflux for 30 minutes with 0.5 eq of fumaric acid. The reaction was cooled and the solvent removed. The crude material was purified by open column chromatograph or preparative chromatograph.

Column Separation of (R,R)-1 and (S,S)-1, Procedure B

A sample of 75 mg of fenoterol HBr was dissolved in 1.5 mL of 95/5/0.05 $CH_3CN$/isopropanol/$HNEt_2$ and applied in 100 μL injections to a CHIRALPAK® AD-H 10×250 mm 5 μm semi-preparative column using a waters 2690 Separations Module, PDA set to 280 nm. The eluting solvent was 95/5/0.05 $CH_3CN$/isopropanol/$HNEt_2$, 5 mL/min Retention times for (S,S) and (R,R) isomers were 4.8 min and 7.8 min, respectively.

(R,R)-(−)-Fenoterol [(R,R)-1]

Obtained according to Procedure B to give 40 mg collected after evaporation. $^1$H NMR ($CD_3OD$) δ 1.05 (d, 3H, J=6.3 Hz), 2.49 (q, 1H, J=6.9 Hz), 2.62-2.74 (m, 2H), 2.80-2.91 (m, 2H), 4.55 (dd, 1H, J=5.1, J=3.3 Hz), 6.16 (t, 1H, J=2.4 Hz), 6.27 (d, 2H, J=2.1 Hz), 6.68 (d, 2H, J=8.4 Hz), 6.94 (d, 2H, J=8.4 Hz); $^{13}$C NMR ($CD_3CN$) δ 20.3, 43.2, 55.1, 55.2, 72.4, 102.2, 105.4, 116.0, 131.3, 131.8, 147.4, 156.2, 159.0; UV (MeOH) $λ_{max}$ 279 nm (ε 2,760), 225 (12,900), 204 (32,600); MS (APCI+) m/z (rel): 304 (100, M+H); $[α]_D$=−29.0° (conc=0.2% MeOH); HPLC: (a) 0.1% diethylamine in $H_2O$, 0.50 mL/min, 254 nm, $t_R$ 2.90 min, 99% pure; (d) $t_R$ 7.8 min, >99% pure.

(S,S)-(+)-Fenoterol [(S,S)-1]

Obtained according to Procedure B to give 35 mg after evaporation. $^1$H NMR ($CD_3OD$) δ 1.05 (d, 3H, J=6.6 Hz), 2.49 (q, 1H, J=7.2 Hz), 2.62-2.76 (m, 2H), 2.80-2.94 (m, 2H), 4.55 (dd, 1H, J=4.8, J=3.3 Hz), 6.16 (t, 1H, J=2.1 Hz), 6.27 (d, 2H, J=2.4 Hz), 6.68 (d, 2H, J=8.4 Hz), 6.94 (d, 2H, J=8.4 Hz); $^{13}$C ($CD_3CN$) δ 20.3, 43.2, 55.0, 55.2, 72.4, 102.2, 105.4, 116.0, 131.3, 131.8, 147.4, 156.2, 159.0; UV (MeOH) $λ_{max}$ 279 nm (ε 2,680), 224 (12,700), 204 (32,800); MS (APCI+) m/z (rel): 304 (100, M+H); $[α]_D$=+28.5° (conc=0.20% MeOH); HPLC: (a) 0.1% diethylamine in $H_2O$, 0.50 mL/min, 254 nm, $t_R$ 2.72 min, >99% pure; (d) $t_R$ 4.8 min, >99% pure.

(R,S)-(−)-Fenoterol Fumarate [(R,S)-1]

Prepared from (R)-8 and (S)-10 according to Procedure A to give 168 mg (64%). $^1$H NMR ($CD_3OD$) δ 1.22 (d, 3H, J=6.6 Hz), 2.64 (dd, 1H, J=9.9 Hz, J=13.2 Hz), 3.01-3.51 (m, 4H), 4.79 (dd, 1H, J=3.0 Hz, J=9.9 Hz), 6.23 (t, 1H, J=2.4 Hz), 6.36 (d, 2H, J=2.1 Hz), 6.75 (s, 1H), 6.76 (d, 2H, J=8.4 Hz), 7.05 (d, 2H, J=8.1 Hz); $^{13}$C NMR ($CD_3OD$) δ 16.2, 39.1, 52.5, 57.4, 70.4, 103.4, 105.3, 116.7, 127.8, 131.4, 135.2, 144.6, 157.7, 160.0, 168.2; UV (MeOH) $λ_{max}$ 278 nm (ε 2,520), 205 (27,900); MS (ESI+) m/z (rel): 304 (100, M+H); $[α]_D$=−7.5° (conc=0.75% MeOH); HPLC: (a) 70/30/0.05. 1.00 mL/min, 282 nm, $t_R$ 1.35 min, >99% pure; (b) 50/50/0.05. 1.0 ml, 0.50 mL/min, 254 nm, $t_R$ 2.72 min, >99% pure; (d) $t_R$ 4.8 min, 1.00 mL/min, 280 nm, $t_R$ 2.10 min, 97.5% pure.

(S,R)-(+)-Fenoterol Fumarate [(S,R)-1]

Prepared from (S)-8 and (R)-10 according to Procedure A to give 104 mg (39%). $^1$H NMR ($CD_3OD$) δ 1.22 (d, 3H, J=6.6 Hz), 2.64 (dd, 1H, J=9.9 Hz, J=13.5 Hz), 3.47-3.04 (m, 4H), 4.80 (dd, 1H, J=2.7, J=9.6 Hz), 6.23 (t, 1H, J=2.4 Hz), 6.36 (d, 2H, J=2.1 Hz), 6.75 (s, 1H), 6.76 (d, 2H, J=8.4 Hz), 7.05 (d, 2H, J=8.4 Hz); $^{13}$C NMR ($CD_3OD$) δ 16.2, 39.1, 52.5, 57.4, 70.4, 103.4, 105.3, 116.7, 127.8, 131.4, 135.2, 144.6, 157.7, 159.9, 168.2; UV (MeOH) $λ_{max}$ 278 nm (ε 2,640), 202 (36,600); MS (ESI+) m/z (rel): 304 (100, M+H), 413 (10); $[α]_D$=+6.4° (conc=0.50% MeOH); HPLC: (a) 70/30/0.05, 1.00 mL/min, 282 nm, $t_R$ 1.35 min, 95.9% pure; (b) 50/50/0.05, 1.0 mL/min, 280 nm, $t_R$ 2.06 min, 99% pure.

(R,R)-(−)-1-p-Methoxyphenyl-2-(β-3',5'-dihydroxy-phenyl-(3-oxy)ethylamino-propane Fumarate [(R,R)-2]

Prepared from (R)-8 and (R)-11 according to Procedure A to give 172 mg (38%). $^1$H NMR ($CD_3OD$) δ 1.08 (d, 3H, J=6.3 Hz), 3.05-2.56 (m, 5H), 4.57 (dd, 1H, J=8.4, 5.4 Hz), 6.16 (m, 1H), 6.26 (d, 2H, J=2.7 Hz), 6.81 (d, 2H, J=8.7 Hz), 7.03 (d, 2H J=8.7 Hz); $^{13}$C NMR ($CD_3OD$) δ 18.8, 42.3, 54.5, 55.6, 56.0, 72.6, 103.0, 105.4, 115.0, 131.1, 131.2, 131.3, 146.2, 159.8, 159.9; UV (MeOH) $λ_{max}$ 277 nm (ε 3,590), 224 (17,700), 207 (29,500); MS (ESI+) m/z (rel): 318 (100, M+H); $[α]_D$=−24.9° (c=0.8 MeOH); HPLC: (a) 70/30/0.05, 1.0 mL/min, 282 nm, $t_R$ 1.54 min, 96.5% pure; (b) 50/50/0.05, 2.0 mL/min, 276 nm, $t_R$ 1.51 min, 95.9% pure.

(S,S)-(+)-1-p-Methoxyphenyl-2-(β-3',5'-dihydroxy-phenyl-(3-oxy)ethylamino-propane Fumarate [(S,S)-2]

Prepared from (S)-8 and (S)-11 according to Procedure A to give 318 mg (53%). $^1$H NMR ($CD_3OD$) δ 1.15 (d, 3H, J=6.0 Hz), 2.58-3.22 (m, 5H), 3.77 (s, 3H), 4.68 (dd, 1H, J=4.8, 8.4 Hz), 6.18 (t, 1H, J=2.1 Hz), 6.31 (d, 2H, J=2.1 Hz), 2.23 (s, 0.5H, fumarate), 6.84 (d, 2H, J=8.7 Hz), 7.10 (d, 2H, J=9.0 Hz); $^{13}$C NMR ($CD_3OD$) δ 16.1, 39.9, 52.4, 54.5, 55.3, 70.4, 101.9, 104.2, 114.0, 129.2, 130.1, 144.4, 158.7, 158.9; UV (MeOH) $λ_{max}$ 277 nm (ε 2,100), 224 (11,00), 205 (22,700); MS (ESI+) m/z (rel): 318 (100, M+H); $[α]_D$=+28.6° (c=0.95 MeOH); HPLC: (a) 70/30/0.05, 1.0 mL/min, 282 nm, $t_R$ 1.67 min, 96.0% pure; (b) 50/50/0.05, 2.0 mL/min, 276 nm, $t_R$ 1.51 min, 97.1% pure.

(R,S)-(−)-1-p-Methoxyphenyl-2-(β-3',5'-dihydroxy-phenyl-(3-oxy)ethylaminopropane Fumarate [(R,S)-2]

Prepared from (R)-8 and (S)-11 according to Procedure A to give 160 mg (38%). $^1$H NMR ($CD_3OD$) δ 1.20 (d, 3H, J=6.6 Hz), 2.62-2.71 (m, 1H), 2.98-3.20 (m, 3H), 3.30-3.42 (m, 2H), 4.73-4.81 (m, 1H), 6.21 (m, 2H), 3.35 (m, 2H), 6.71 (s, 0.5H), fumarate), 6.56-6.89 (m, 2H), 7.11-7.19 (m, 2H); $^{13}$C NMR ($CD_3OD$) δ 15.6, 38.5, 51.8, 54.5, 55.9, 69.7, 102.1, 104.1, 114.1, 128.5, 130.2, 136.0, 143.8, 158.8, 159.1; UV (MeOH) $λ_{max}$ 277 nm (ε 4,100), 224 (21,400), 203 (50,600); MS (ESI+) m/z (rel): 318 (100, M+H); $[α]_D$=−

7.2° (c=1.5 MeOH); HPLC: (a) 70/30/0.05, 1.00 mL/min, 282 nm, $t_R$ 1.40 min, 99% pure; (b) 50/50/0.05, 2.0 mL/min, 276 nm, $t_R$ 1.51 min, 96.1% pure.

(S,R)-(+)-1-p-Methoxyphenyl-2-(β-3',5'-dihydroxy-phenyl-(3-oxy)ethylaminopropane Fumarate [(S,R)-2]

Prepared from (S)-8 and (R)-11 according to Procedure A to give 200 mg (51%). $^1$H NMR (CD$_3$OD) δ 1.12 (d, 3H, J=6.0 Hz), 2.58-3.13 (m, 5H), 3.77 (s, 3H), 4.62 (dd, 1H, J=3.6, 9.0 Hz), 6.15 (m, 1H), 6.30 (d, 2H, J=1.8 Hz), 6.85 (d, 2H, J=8.7 Hz), 7.11 (d, 2H, J=8.7 Hz); $^{13}$C NMR (CD$_3$OD) δ 18.2, 41.4, 54.1, 55.7, 56.5, 64.7, 103.0, 105.3, 115.1, 130.7, 131.3, 145.9, 159.8, 160.0; UV (MeOH) $\lambda_{max}$ 277 nm (ε 3,150), 224 (3,310), 205 (30,600); MS (ESI+) m/z (rel): 318 (100, M+H); $[\alpha]_D$=+14.1° (c=0.95 MeOH); HPLC: (a) 70/30/0.05, 1.00 mL/min, 282 nm, $t_R$ 1.42 min, 97.7% pure; (b) 50/50/0.05, 2.0 mL/min, 276 nm, $t_R$ 1.52 min, 97.8% pure.

(R,R)-(−)-5-{2-[2-(4-Aminophenyl)-1-methylethyl-amino]-1-hydroxyethyl}-1,3-benzenediol [(R,R)-3]

Prepared from (R)-8 and (R)-12 according to Procedure A to give 88 mg (42%). $^1$H NMR (CD$_3$OD) δ 1.23 (m, 3H), 2.70-3.24 (m, 4H), 3.54 (m, 1H), 4.84 (dd, 1H, J=3.3, 9.6 Hz), 6.23 (t, 1H, J=2.4 Hz), 6.38 (d, 2H, J=2.1 Hz), 6.75 (s, 2H, fumarate), 7.35 (dd, 4H, J=8.1, 21.0 Hz); $^{13}$C (CD$_3$OD) δ 15.5, 39.6, 52.7, 56.6, 70.3, 103.4, 105.3, 123.8, 132.0, 132.1, 135.2, 137.5, 144.7, 160.0, 168.1; UV (MeOH) $\lambda_{max}$ 284 nm (ε 1,520), 206 (21,700); MS (ESI+) m/z (rel): 303 (100, M+H); $[\alpha]_D$=−6.8° (conc=1.0% MeOH); HPLC: (a) 50/20/0.05, 0.70 mL/min, 276 nm, $t_R$ 2.07 min, 95.5% pure; (b) 50/50/0.05, 1.0 mL/min, 282 nm, $t_R$ 2.60, 97.16% pure.

(S,S)-(+)-5-{2-[2-(4-Aminophenyl)-1-methylethyl-amino]-1-hydroxyethyl}-1,3-benzenediol Fumarate [(S,S)-3]

Prepared from (S)-8 and (S)-12 according to Procedure A to give 56 mg (25%). $^1$H NMR (CD$_3$OD) δ 1.23 (m, 3H), 2.62-3.27 (m, 4H), 3.55 (m, 1H), 4.74-4.88 (m, 1H), 6.22 (t, 1H, J=1.8 Hz), 6.37 (d, 2H, J=2.4 Hz), 6.75 (s, 2H, fumarate), 7.32 (dd, 4H, J=8.7, 25.8 Hz); $^{13}$C NMR (CD$_3$OD) δ 15.5, 39.6, 52.5, 56.7, 70.7, 103.4, 105.3, 123.3, 131.8, 132.0, 135.2, 136.9, 144.7, 160.0, 168.1; UV (MeOH) $\lambda_{max}$ 284 nm (ε 1,720), 207 (28,400); MS (ESI+) m/z (rel): 303 (100, M+H), 329 (20); $[\alpha]_D$=+11.1° (conc=0.50% MeOH); HPLC: (a) 80/20/0.05, 0.7 mL/min, 276 nm, $t_R$ 2.01 min, <99% pure; (b) 50/50/0.05, 1.0 mL/min, 282 nm, $t_R$ 2.50 min, 99.4% pure.

(R,S)-(−)-5-{2-[2-(4-Aminophenyl)-1-methylethyl-amino]-1-hydroxyethyl}-1,3-benzenediol Fumarate [(R,S)-3]

Prepared from (R)-8 and (S)-12 according to Procedure A to give 72 mg (35%). $^1$H NMR (CD$_3$OD) δ 1.23 (m, 3H), 2.73-3.24 (m, 4H), 3.51 (m, 1H), 4.80 (dd, 1H, J=2.7, 9.6 Hz), 6.22 (t, 1H, J=2.1 Hz), 6.36 (d, 2H, J=2.4 Hz), 6.75 (s, 2H, fumarate), 7.32 (dd, 4H, J=8.4, 25.2 Hz); $^{13}$C NMR (CD$_3$OD) δ 16.1, 39.12, 5.16, 56.9, 70.4, 103.4, 105.3, 123.4, 132.0, 132.0, 135.2, 136.8, 144.6, 160, 168.10; UV (MeOH) $\lambda_{max}$ 284 nm (ε 1,620), 205 (27,200); MS (ESI+) m/z (rel): 303 (100, M+H), 134 (14); $[\alpha]_D$=−7.5° (conc=0.50% MeOH); HPLC: (a) 80/20/0.05, 0.7 mL/min, 276 nm, $t_R$ 2.08 min, 95.0% pure; (b) 50/50/0.05, 1.0 mL/min, 282 nm, $t_R$ 2.51 min, 97.4% pure.

(S,R)-(+)-5-{2-[2-(4-Aminophenyl)-1-methylethyl-amino]-1-hydroxyethyl}-1,3-benzenediol Fumarate [(S,R)-3]

Prepared from (S)-8 and (R)-12 according to Procedure A to give 93 mg (42%). $^1$H NMR (CD$_3$OD) δ 1.23 (d, 3H, J=6.3 Hz), 2.70-3.78 (m, 4H), 3.42-3.62 (m, 1H), 4.80 (dd, 1H, J=3.0, 9.9 Hz), 6.22 (t, 1H, J=2.1 Hz), 6.37 (d, 2H, J=2.1 Hz), 6.75 (s, 2H, fumarate), 7.33 (dd, 4H, J=8.4, 26.7 Hz); $^{13}$C NMR (CD$_3$OD) δ 16.2, 39.1, 52.6, 56.9, 70.5, 103.4, 105.3, 123.5, 132.1, 133.7, 135.2, 137.1, 144.7, 160.0, 168.1 UV (MeOH) $\lambda_{max}$ 284 nm (ε 8,230), 207 (100,000); MS (ESI+) m/z (rel): 303 (100, M+H), 134 (18); $[\alpha]_D$=+11.4° (conc=0.50% MeOH); HPLC: (a) 70/30/0.05, 1.00 mL/min, 280 nm, $t_R$ 1.45 min, 99% pure; (b) 50/50/0.05, 1.0 mL/min, 282 nm, $t_R$ 2.63 min, 95.33% pure.

(R,R)-(−)-5-[1-Hydroxy-2-(1-methyl-2-phenylethyl-amino)ethyl]-1,3-benzenediol fumarate [(R,R)-4]

Prepared from (R)-8 and (R)-13 according to Procedure A to give 92 mg (26%). $^1$H NMR (CD$_3$OD) δ 1.22 (m, 3H), 2.68-3.28 (m, 2H), 3.10-3.28 (m, 2H), 3.53 (br-m, 1H), 4.75-4.80 (m, 1H), 6.24 (t, 1H, J=2.4 Hz), 6.38 (d, 2H, J=2.1 Hz), □6.75 (s, 1H, fumarate), 7.22-7.33 (m, 5H); $^{13}$C NMR (CD$_3$OD) δ 15.5, 40.3, 56.9, 70.2, 103.4, 105.3, 128.3, 129.9, 130.3, 135.2, 137.3, 144.6, 144.6, 159.9, 168.1; UV (MeOH) $\lambda_{max}$ 277 nm (ε 926), 204 (18,700); MS (APCI+) m/z 288 (100, M+H); $[\alpha]_D$=−21.2° (conc=0.85% MeOH); HPLC: (a) 50/50/0.05, 1.00 mL/min, 282 nm; $t_R$ 1.73 min; 99% pure; (b) 50/50/0.05, 2.0 mL/min, 276 nm, $t_R$ 1.46 min, 97.5% pure.

(S,S)-(+)-5-[1-Hydroxy-2-(1-methyl-2-phenylethyl-amino)ethyl]-1,3-benzenediol fumarate [(S,S)-4]

Prepared from (S)-8 and (S)-13 according to Procedure A to give 184 mg (51%). $^1$H NMR (CD$_3$OD) δ 1.21 (m, 3H), 2.70-3.13 (m, 2H), 3.15-3.23 (m, 2H), 3.54 (br-m, 1H), 4.79-4.86 (m, 1H), 6.24 (t, 1H, J=2.1 Hz), 6.39 (t, 2H, J=2.7 Hz), 6.76 (s, 1H, fumarate), 7.22-7.32 (m, 5H); $^{13}$C NMR (CD$_3$OD) δ 15.5, 40.3, 56.9, 70.2, 103.4, 105.3, 128.3, 129.9, 130.3, 135.1, 137.3, 144.6, 144.6, 159.9, 168.1 UV (MeOH) $\lambda_{max}$ 278 nm (ε 1,510), 207 (26,600); MS (APCI+) m/z 288 (100, M+H); $[\alpha]_D$=+19.3° (conc=0.90% MeOH); HPLC: (a) 50/50/0.05, 1.00 mL/min, 282 nm, $t_R$ 1.49 min; 98.4% pure; (b) 50/50/0.05, 2.0 mL/min, 276 nm, $t_R$ 1.35 min, 99% pure.

(R,S)-(−)-5-[1-Hydroxy-2-(1-methyl-2-phenylethyl-amino)ethyl]-1,3-benzenediol fumarate [(R,S)-4]

Prepared from (R)-8 and (S)-13 according to Procedure A to give 170 mg (45%). $^1$H NMR (CD$_3$OD) δ 1.22 (m, 3H), 2.68-3.28 (m, 2H), 3.13-3.28 (m, 2H), 3.53 (br-m, 1H), 4.76-4.80 (m, 1H), 6.23 (t, 1H, J=2.1 Hz), 6.37 (t, 2H, J=3.0 Hz), 6.75 (s, 1H, fumarate), 7.24-7.37 (m, 5H); $^{13}$C NMR (CD$_3$OD) δ 16.3, 24.2, 39.8, 57.2, 70.5, 103.4, 105.3, 128.4, 130.0, 130.4, 135.2, 137.4, 144.6, 160.1 UV (MeOH) $\lambda_{max}$ 278 nm (ε 1,110), 205 (31,000); MS (APCI+) m/z (rel): 288 (100, M+H); $[\alpha]_D$=−6.9° (conc=0.85% MeOH); HPLC: (a)

(S,R)-(+)-5-[1-Hydroxy-2-(1-methyl-2-phenylethylamino)ethyl]-1,3-benzenediol fumarate [(S,R)-4]

Prepared from (S)-8 and (R)-13 according to Procedure A to give 212 mg (59%). $^1$H NMR (CD$_3$OD) δ 1.22 (m, 3H), 2.72 (dd, 1H J=10.2, 13.2 Hz), 3.11 (dd, 1H, J=10.2, 12.6 Hz), 3.18-3.27 (m, 2H), 3.48-3.61 (m, 1H), 4.83 (dd, 1H, J=3.3, 9.9 Hz), 6.22 (t, 1H, J=2.4 Hz), 6.36 (d, 2H, J=2.4 Hz), 6.75 (s, 1H, fumarate), 7.24-7.37 (m, 5H); $^{13}$C NMR (CD$_3$OD) δ 16.3, 24.2, 39.8, 57.2, 70.5, 103.4, 105.3, 128.4, 130.0, 130.4, 135.2, 137.4, 144.6, 160.1; UV (MeOH) λ$_{max}$ 278 nm (ε 1,680), 206 (35,500); MS (APCI+) m/z (rel): 288 (100, M+H), 270 (19, M−OH); [α]$_D$=+9.1° (conc=1.1%, MeOH); HPLC: (a) 50/50/0.05, 1.00 mL/min, 282 nm, t$_R$ 1.51 min, 99% pure; (b) 50/50/0.05, 2.0 mL/min, 276 nm, t$_R$ 1.43 min, 99% pure.

(R,R)-(−)-5-{1-hydroxy-2-[1-methyl-2-(1-naphthyl)ethylamino]ethyl}-1,3-benzenediol fumarate [(R,R)-5]

Prepared from (R)-8 and (R)-14 according to Procedure A to give 135 mg (46%). $^1$H NMR (CD$_3$OD) δ 1.18-1.23 (m, 3H), 3.16-3.34 (m, 1H, 2H), 3.69-3.74 (m, 2H), 4.78-4.80 (m, 1H), 6.23 (t, 1H, J=2.4 Hz), 6.38 (m, 2H), 7.41-7.61 (m, 4H), 7.83 (d, 1H, J=7.5 Hz), 7.90 (d, 1H, J=7.8 Hz), 8.10 (m, 1H); $^{13}$C NMR (CD$_3$OD) δ 16.2, 37.2, 54.5, 56.1, 70.3, 103.4, 105.3, 124.3, 126.5, 127.0, 127.7, 129.3, 130.1, 133.2, 135.2, 135.6, 144.7, 160.1, 168.2; UV (MeOH) λ$_{max}$ 282 nm (ε 5,860), 224 (50,900), 208 (35,500); MS (APCI+) m/z (rel): 338 (100, M+H), 169 (15, fragment); [α]$_D$=−20.4 (conc=0.50% MeOH); HPLC: (a) 60/40/0.05, 1.00 mL/min, 282 nm, t$_R$ 2.08 min, 95.7% pure; (b) 50/50/0.05, 1.5 mL/min, 282 nm, t$_R$ 2.20 min, 99% pure.

(S,S)-(+)-5-{1-hydroxy-2-[1-methyl-2-(1-naphthyl)ethylamino]ethyl}-1,3-benzenediol fumarate [(S,S)-5]

Prepared from (S)-8 and (S)-14 according to Procedure A to give 118 mg (40%) $^1$H NMR (CD$_3$OD) δ 1.13-1.17 (m, 3H), 3.14-3.26 (m, 1H, 2H), 3.61-3.76 (m, 2H), 4.44-4.75 (m, 1H), 6.18 (t, 1H, J=2.4 Hz), 6.33 (m, 2H), 7.36-7.52 (m, 4H), 7.77 (dd, 1H, J=1.8, 7.5 Hz), 7.84 (d, 1H, J=8.1 Hz), 8.04 (t, 1H, J=8.4 Hz); $^{13}$C NMR (CD$_3$OD) δ 16.1, 37.1, 54.4, 56.0, 70.3, 103.3, 105.3, 124.3, 126.5, 127.0, 127.7, 129.2, 130.0, 133.2, 135.2, 135.7, 144.5, 160.0, 168.1; UV (MeOH) λ$_{max}$ 282 nm (ε 6,210), 223 (56,400), 208 (42,700); MS (APCI+) m/z (rel): 338 (100, M+H), 169 (8, fragment); [α]$_D$=+20.0° (conc=1.1% MeOH); HPLC: (a) 60/40/0.05, 1.00 mL/min, 282 nm, t$_R$ 2.35 min, 98.9% pure; (b) 50/50/0.05, 1.5 mL/min, 282 nm, t$_R$ 2.26 min, 97.2% pure.

(R,S)-(−)-5-{1-hydroxy-2-[1-methyl-2-(1-naphthyl)ethylamino]ethyl}-1,3-benzenediol fumarate [(R,S)-5]

Prepared from (R)-8 and (S)-14 according to Procedure A to give 114 mg (39%). $^1$H NMR (CD$_3$OD) δ 1.08-1.11 (m, 3H), 3.02-3.24 (m, 1H, 2H), 3.54-3.68 (m, 2H), 4.45-4.75 (m, 1H), 6.11 (t, 1H, J=1.8 Hz), 6.26 (m, 2H), 6.63 (s, 2H fumarate), 7.28-7.48 (m, 4H), 7.70 (d, 1H, J=7.5 Hz), 7.77 (d, 1H, J=7.8 Hz), 7.97 (t, 1H, J=7.8 Hz); $^{13}$C NMR (CD$_3$OD) δ 16.0, 37.1, 52.5, 56.0, 70.4, 103.4, 105.3, 124.4, 126.5, 127.0, 127.6, 129.2, 130.1, 133.1, 135.2, 135.5, 144.7, 159.9, 168.2; UV (MeOH) λ$_{max}$ 281 nm (ε 12,600), 224 (61,900), 204 (47,200); MS (APCI+) m/z (rel): 338 (100, M+H), 190 (15, fragment); [α]$_D$=−11.3° (conc=0.85% MeOH); HPLC: (a) 60/40/0.05, 1.00 mL/min, 282 nm, t$_r$ 2.30 min, 98.6% pure; (b) 50/50/0.05, 1.5 mL/min, 282 nm, t$_R$ 2.36 min, 99% pure.

(S,R)-(+)-5-{1-hydroxy-2-[1-methyl-2-(1-naphthyl)ethylamino]ethyl}-1,3-benzenediol fumarate [(S,R)-5]

Prepared from (S)-8 and (R)-14 according to Procedure A to give 123 mg (42%). $^1$H NMR (CD$_3$OD) δ 1.18-1.22 (m, 3H), 3.10-3.28 (m, 1H, 2H), 3.69-3.78 (m, 2H), 4.45-4.75 (m, 1H), 6.23 (t, 1H, J=2.1 Hz), 6.39 (m, 2H), 6.73 (s, 2H fumarate), 7.39-7.59 (m, 4H), 7.80 (d, 1H, J=7.5 Hz), 7.88 (d, 1H, J=7.8 Hz), 8.01 (t, 1H, J=9.0 Hz); $^{13}$C NMR (CD$_3$OD) δ 16.4, 37.4, 52.5, 56.2, 70.6, 103.4, 105.3, 124.4, 126.5, 127.0, 129.3, 130.1, 133.1, 133.4, 135.6, 136.3, 144.8, 160.0, 171.4; UV (MeOH) λ$_{max}$ 282 nm (ε 7,740), 224 (70,900), 206 (55,800); MS (ESI+) m/z (rel): 338 (100, M+H); [α]$_D$=+15.5 (conc=1.0% MeOH) HPLC: (a) 60/40/0.05, 1.0 mL/min, 282 nm, t$_R$ 1.95, 95.7% pure; (b) 50/50/0.05, 1.5 mL/min, 282 nm, t$_R$ 2.29 min, 95.7% pure.

(R,R)-(−)-5-[1-Hydroxy-2-(1-methylhexylamino)ethyl]-1,3-benzenediol Fumarate [(R,R)-6]

Prepared from (R)-8 and (R)-15 according to Procedure A to give 45 mg (29%). $^1$H NMR (CD$_3$OD) δ 0.920 (t, 3H, J=6.9 Hz), 1.30 (d, 3H, J=6.9 Hz), 1.29-1.64 (m, 8H), 3.01-3.18 (m, 2H), 3.14-3.30 (m, 1H), 4.80 (dd, 1H, J=3.3, 9.6 Hz), 6.22 (t, 1H, J=2.1 Hz), 6.36 (d, 2H, J=2.4 Hz), 6.75 (s, 1H, fumarate); $^{13}$C NMR (CD$_3$OD) δ 14.3, 16.0, 23.5, 26.2, 32.6, 34.2, 52.1, 55.7, 70.2, 103.3, 105.3, 135.2, 144.7, 160.0, 168.0; UV (MeOH) λ$_{max}$ 278 nm (ε 931), 203 nm (20,100); MS (ESI+) m/z (rel): 268 (100, M+H); [α]$_D$=−8.8° (conc=1.1% MeOH); HPLC: (c) 70/30/0.1, 1.0 mL/min, 276 nm, t$_R$ 2.18 min, 96.6% pure; (b) 50/50/0.05, 1.0 mL/min, 279 nm, t$_R$ 2.06 min, 98.9% pure.

(S,S)-(+)-5-[1-Hydroxy-2-(1-methylhexylamino)ethyl]-1,3-benzenediol Fumarate [(S,S)-6]

Prepared from (S)-8 and (S)-15 according to Procedure A to give 96 mg (43%). $^1$H NMR (CD$_3$OD) δ 0.923 (t, 3H, J=6.6 Hz); 1.31 (d, 3H, J=6.6 Hz), 1.26-1.84 (m, 8H), 2.01-3.18 (m, 2H), 3.14-3.30 (m, 1H), 4.81 (dd, 1H, J=3.3, 9.6 Hz), 6.23 (t, 1H, J=2.4 Hz), 6.39 (d, 2H, J=2.1 Hz), 6.76 (s, 1H, fumarate): $^{13}$C NMR (CD$_3$OD) δ 14.2, 16.0, 23.4, 26.3, 32.6, 34.1, 52.1, 55.8, 70.2, 103.4, 105.3, 135.2, 144.7, 159.9, 168.2; UV (MeOH) λ$_{max}$ 278 nm (ε 1,340), 203 (28,800); MS (APCI+) m/z (rel): 268 (100, M+H); [α]$_D$=+10.8° (conc=0.50% MeOH); HPLC: (c) 70/30/0.1, 1.0 mL/min, 276 nm, $t_R$ 2.16 min, 97.0% pure; (b) 50/50/0.05, 1.0 mL/min, 279 nm, $t_R$ 2.11 min, 99% pure.

(R,S)-(−)-5-[1-Hydroxy-2-(1-methylhexylamino)ethyl]-1,3-benzenediol Fumarate [(R,S)-6]

Prepared from (R)-8 and (S)-15 according to Procedure A to give 83 mg (38%). $^1$H NMR (CD$_3$OD) δ 0.924 (m, 3H); 1.32 (d, 3H, J=6.6 Hz), 1.26-1.84 (m, 8H), 2.98-3.20 (m, 2H), 3.32-3.22 (m, 1H), 4.78 (dd, 1H, J=3.0, 9.9 Hz), 6.23 (t, 1H, J=2.1 Hz), 6.37 (d, 2H, J=1.8 Hz), 6.76 (s, 1H, fumarate); $^{13}$C NMR (CD$_3$OD) δ 14.2, 16.4, 23.4, 26.2, 32.6, 33.5, 52.2, 56.0, 70.4, 103.4, 105.3, 135.2, 144.7, 160.0, 168.1; UV (MeOH) $\lambda_{max}$ 276 nm (ε 2,770), 203 (35,900); MS (APCI+) m/z (rel): 268 (100, M+H); $[\alpha]_D$=−15.9° (conc=0.70% MeOH); HPLC: (c) 70/30/0.1, 1.0 mL/min, 276 nm, $t_R$ 2.16 min, 97.0% pure; (b) 50/50/0.05, 1.0 mL/min, 279 nm, $t_R$ 2.07 min, 96.2% pure.

(S,R)-(+)-5-[1-Hydroxy-2-(1-methylhexylamino)ethyl]-1,3-benzenediol Fumarate [(S,R)-6]

Prepared from (S)-8 and (R)-15 according to Procedure A to give 81 mg (38%). $^1$H NMR (CD$_3$OD) δ 0.920 (t, 3H, J=6.3 Hz), 1.32 (d, 3H, J=6.9 Hz), 1.30-1.77 (m, 8H), 2.99-3.17 (m, 2H), 3.23-3.26 (m, 1H), 4.76 (dd, 1H, J=3.0, 9.6 Hz), 6.22 (t, 1H, J=2.4 Hz), 6.36 (d, 2H, J=2.1 Hz), 6.75 (s, 1H, fumarate); $^{13}$C NMR (CD$_3$OD) δ 14.2, 16.5, 23.5, 26.2, 32.6, 39.5, 52.2, 56.0, 70.4, 103.4, 105.3, 135.2, 144.7, 160.0, 168.0; UV (MeOH) $\lambda_{max}$ 278 nm (ε 1,440), 204 (29,900); MS (APCI+) m/z (rel): 268 (100, M+H); $[\alpha]_D$=+12.7° (conc=1.0% MeOH); HPLC: (c) 70/30/0.1, 1.0 mL/min, 276 nm, $t_R$ 2.16 min, 99% pure; (b) 50/50/0.05, 1.0 mL/min, 279 nm, $t_R$ 2.02 min, 95.7% pure.

(R)-(−)-5-(1-Hydroxy-2-phenethylaminoethyl)-1,3-benzenediol fumarate [(R)-7]

Prepared from (R)-8 and 28 to give 37 mg (15%). $^1$H NMR (CD$_3$OD) δ 2.94-3.23 (m, 6H), 4.73 (dd, 1H, J=3.3, 9.9 Hz), 6.15 (t, 1H, J=2.4 Hz), 6.29 (d, 2H, J=1.8 Hz), 7.19-7.28 (m, 5H), 6.69 (s, 1H); UV (MeOH) $\lambda_{max}$ 278 nm (ε 1,360), 205 (32,600); MS (APCI+) m/z (rel): 274 (100, M+H); $[\alpha]_D$=−13.0° (conc=1.0% MeOH); HPLC: (a) 80/20/0.05, 1.00 mL/min, 282 nm, $t_R$ 1.47 min, 96.7% pure; (b) 50/50/0.05, 1.0 mL/min, 272 nm, $t_R$ 2.78 min, 95.1% pure.

(S)-(+)-5-(1-hydroxy-2-phenethylaminoethyl)-1,3-benzenediol fumarate [(S)-7]

Prepared from (S)-8 and 28 to give 51 mg (17%). $^1$H NMR (CD$_3$OD) δ 2.87-3.21 (m, 6H), 4.68 (dd, 1H, J=3.6, 9.9 Hz), 6.10 (t, 1H, J=2.4 Hz), 6.24 (d, 2H, J=2.1 Hz), 6.63 (s, 1H), 7.12-7.21 (m, 5H); UV (MeOH) $\lambda_{max}$ 278 nm (ε 1,280), 204 (33,700); MS (APCI+) m/z (rel): 274 (100, M+H); $[\alpha]_D$=+14.64° (conc=1.1% MeOH); HPLC: (a) 80/20/0.05, 1.00 mL/min, 282 nm, $t_R$ 1.47 min, 98.6% pure; (b) 50/50/0.05, 1.0 mL/min, 272 nm, $t_R$ 2.74 min, 98.8% pure.

(R,R)-(−)-ethylfenoterol

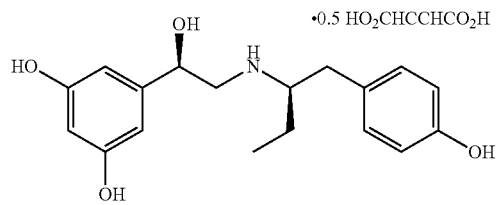 [SMILES: CC[C@H](Cc1ccc(O)cc1)NC[C@H](O)c1cc(O)cc(O)c1]

$^1$H NMR: (300 MHz, CD$_3$OD): δ 0.950 (t, 3H, J=7.5 Hz), 1.67 (m, 2H), 2.83-3.18 (m, 4H), 3.33-3.40 (m, 1H), 3.37 (s, 4H), 4.82 (m, 1H), 6.24 (d, 1H, J=2.1 Hz), 6.37 (d, 2H, J=1.8 Hz), 6.73 (s, 2H, fum), 6.76 (d, 2H, J=8.4 Hz), 7.05 (d, 2H, J=8.7 Hz) ppm. CMR: $^{13}$C (75 MHz, CD$_3$OD): δ 9.43, 23.28, 36.56, 52.29, 62.16, 70.02, 103.4, 105.3, 116.7, 127.8, 131.3, 136.5, 144.6, 157.6, 159.9, 172.3 Ppm. UV: (Methanol), $\lambda_{max}$ (ε): 206 nm (22,500), 223 (12,300), 278 (2,460). MS: (LCQ DUO ESI positive ion mass spectrum) M/z (rel): 318 (100, M+H). HPLC 1:Column:Varian Sunfire C18 100×4.6; 70/30/0.1 water/acetonitrile/TFA; 1.0 mL/min; Det: 278 nm; 2.76 min (fumarate, 6.99%), 3.57 min (90.11%); Purity: 97.1%. HPLC 2: Column. Chiralpak IA 250×10; 90/10/0.05 acetonitrile/methanol/TFA; 2.0 mL/min; Det: 278 nm; 5.26 (RR isomer, 92.37%), 7.11 min (fumarate, 5.02%); Purity 97.5%. Specific Rotation: $[\alpha]_D$=−15.6 (free amine, 0.5% MeOH).

(R,S)-(−)-ethylfenoterol

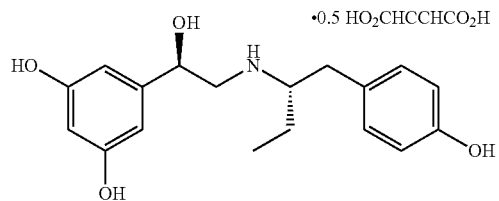 [SMILES: CC[C@@H](Cc1ccc(O)cc1)NC[C@H](O)c1cc(O)cc(O)c1]

$^1$H NMR: (300 MHz, CD$_3$OD): δ 0.972 (t, 3H, J=7.5 Hz), 1.70 (p, 2H, J=6.9 Hz)), 2.86-3.22 (m, 4H), 3.32-3.37 (m, 1H), 3.34 (s, 4H), 4.82 (m, 1H), 6.25 (t, 1H, J=2.1 Hz), 6.36 (d, 2H, J=1.8 Hz), 6.74 (s, 2H, fum), 6.77 (d, 2H, J=8.4 Hz), 7.08 (d, 2H, J=8.7 Hz) ppm. CMR: $^{13}$C (75 MHz, CD$_3$OD): δ 9.820, 24.16, 36.48, 52.30, 62.32, 69.92, 103.3, 105.3, 116.8, 127.7, 131.3, 136.1, 144.4, 157.6, 159.8, 171.3 ppm. UV: (Methanol), $\lambda_{max}$ (ε): 204 (26,900), 224 (11,500), 278 (2,320). MS: (LCQ DUO ESI positive ion mass spectrum) M/z (rel): 318 (100, M+H). HPLC 1:Column:Varian Sunfire C18 100×4.6; 70/30/0.1 water/acetonitrile/TFA; 1.0 mL/min; Det: 278 nm; 2.79 min (fumarate, 3.34%), 3.56 min (96.11%); Purity: 99.5% HPLC 2: Column Chiralpak IA 250×10; 90/10/0.05 acetonitrile/methanol/TFA; 2.0 mL/min; Det: 278 nm; 5.88 (RS isomer, 97.08%), 7.12 min (fumarate, 2.92%); Purity >99%. Specific Rotation: $[\alpha]_D$=−7.2 (free amine, 0.5% MeOH).

$C_{22}H_{25}NO_4 \cdot 0.5 C_4H_4O_4$

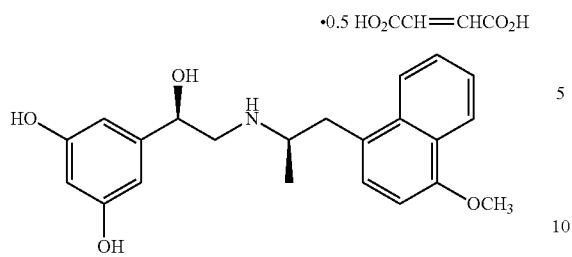

·0.5 HO$_2$CCH═CHCO$_2$H

¹H NMR: (300 MHz, CD$_3$OD): δ 1.22 (t, 3H, J=6.6 Hz), 3.09-3.21 (m, 3H), 3.59-3.69 (m, 2H), 3.99 (s, 3H), 4.74-4.83 (m, 1H), 6.23 (t, 1H, J=2.4 Hz), 6.37 (dd, 2H, J=2.4, 5.7 Hz), 6.74 (s, 1H), 6.86 (d, 1H, J=7.8 Hz), 7.32 (d, 1H, J=7.8 Hz), 7.48 (t, 1H, J=6.9 Hz), 7.56 (t, 1H, J=6.9 Hz), 8.02 (dd, 1H, J=8.4, 12.0 Hz), 8.27 (d, 1H, J=8.7 Hz) ppm. CMR: ¹³C (75 MHz, CD$_3$OD): δ 15.78, 36.66, 52.39, 55.96, 70.20, 103.4, 104.5, 105.3, 123.8, 124.3, 124.9, 126.2, 127.4, 128.1, 129.5, 133.8, 135.2, 144.6, 156.6, 160.0, 168.3 ppm. UV: (Methanol), λ$_{max}$ (ε): 298 nm (4,970), 286 (9,920), 234 (22,600), 210 (42,500). MS: (LCQ DUO ESI positive ion mass spectrum) M/z (rel): 368 (100, M+H). Specific Rotation: [α]$_D$=−28.8 (Free Amine; 0.5% MeOH).

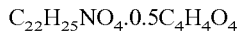

·0.5 HO$_2$CCH═CHCO$_2$H

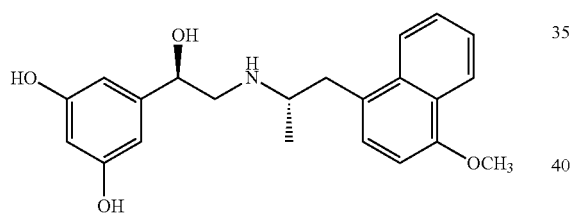

¹H NMR: (300 MHz, CD$_3$OD): δ 1.20 (t, 3H, J=6.6 Hz), 3.07-3.21 (m, 3H), 3.52-3.75 (m, 2H), 3.97 (s, 3H), 4.69-4.83 (m, 1H), 6.24 (t, 1H, J=2.1 Hz), 6.39 (dd, 2H, J=2.4, 5.4 Hz), 6.74 (s, 1H), 6.84 (d, 1H, J=7.8 Hz), 7.31 (d, 1H, J=8.1 Hz), 7.48 (t, 1H, J=6.9 Hz), 7.56 (t, 1H, J=6.9 Hz), 8.01 (dd, 1H, J=8.4, 13.5 Hz), 8.27 (d, 1H, J=7.8 Hz) ppm. CMR: ¹³C (75 MHz, CD$_3$OD): δ 15.77, 36.64, 52.37, 55.94, 70.46, 103.4, 104.5, 105.3, 123.8, 124.3, 124.9, 126.2, 127.4, 128.1, 129.4, 133.8, 135.5, 144.7, 156.6, 160.0, 169.0 ppm. UV:(Methanol), λ$_{max}$ (ε): 298 nm (5,430), 286 (5,710), 233 (25,100), 210 (43,200). MS: (LCQ DUO ESI positive ion mass spectrum) M/z (rel): 368 (100, M+H). Specific Rotation: [α]$_D$=−15.8 (Free Amine; 0.5% MeOH).

A step in the synthesis of the 4 stereoisomers of 1-6 was the coupling of the epoxide formed from either (R)- or (S)-3',5'-dibenzyloxyphenylbromohydrin with the (R)- or (S)-enantiomer of the appropriate benzyl-protected 2-amino-3-benzylpropane (1-5) or the (R)- or (S)-enantiomer of N-benzyl-2-aminoheptane (6), Scheme I.

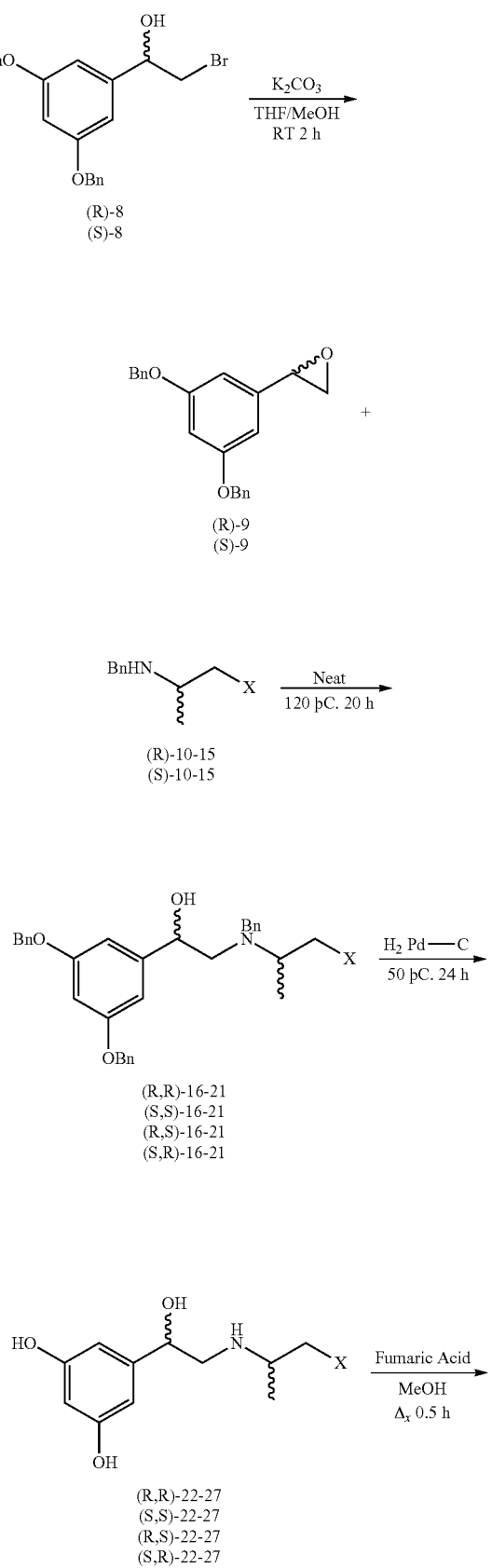

Scheme I

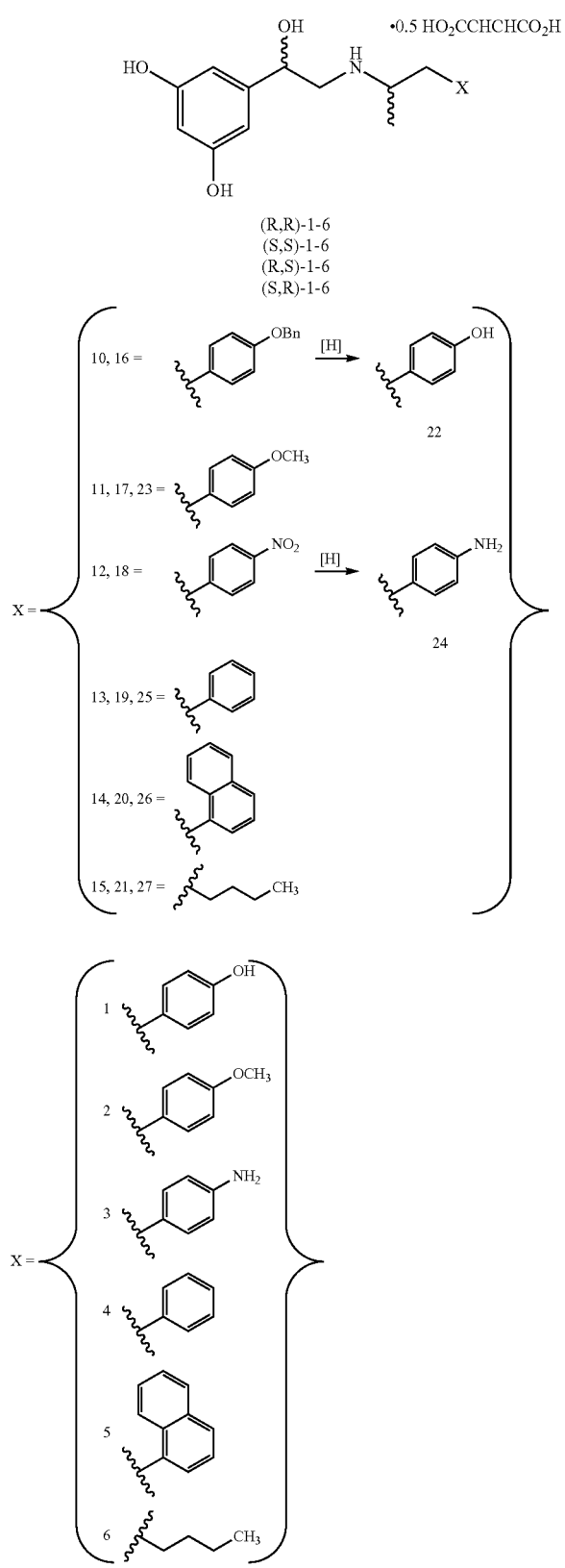
The synthesis of (R)-7 and (S)-7 was accomplished using 2-phenethylamine, Scheme II. This approach was similar to the one developed by Trofast et al. (*Chirality* 3: 443-450, 1991) for the synthesis of the stereoisomers of formoterol, compound 47, FIG. 5. The resulting compounds were then deprotected by hydrogenation over Pd/C and purified as the fumarate salts.
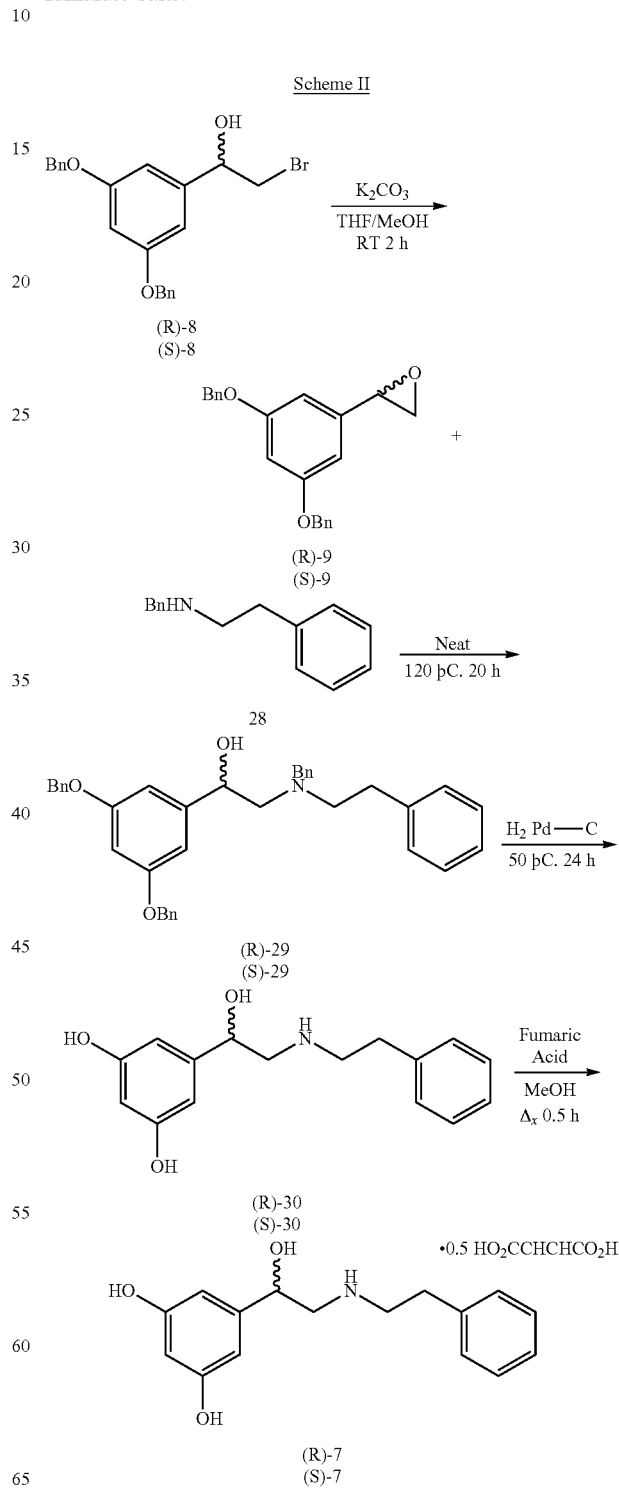

The chiral building blocks used in the syntheses were produced using Scheme III. The (R)- and (S)-3',5'-dibenzyloxyphenyl-bromohydrin enantiomers were obtained by the enantiospecific reduction of 3,5-dibenzyloxyα-bromoacetophenone using boron-methyl sulfide complex (BH$_3$SCH$_3$) and either (1R, 2S)- or (1S, 2R)-cis-1-amino-2-indanol. The required (R)- and (S)-2-benzylaminopropanes were prepared by enantioselective crystallization of the rac-2-benzylaminopropanes using either (R)- or (S)-mandelic acid as the counter ion.

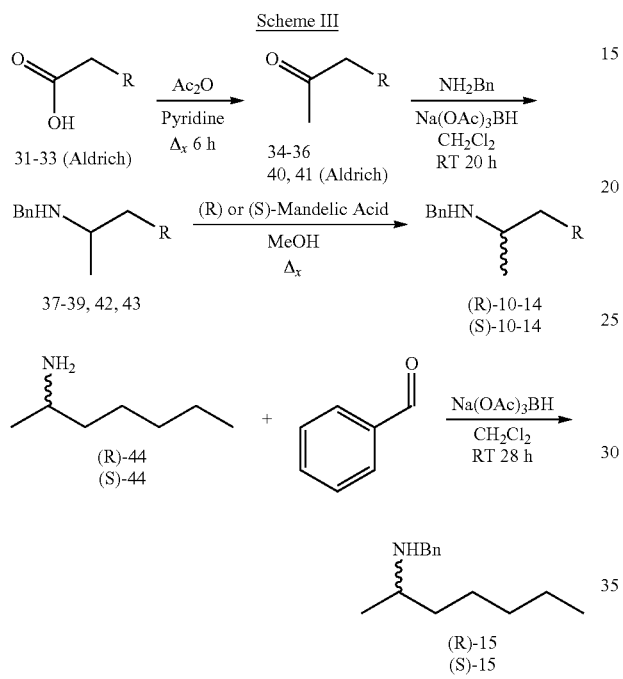

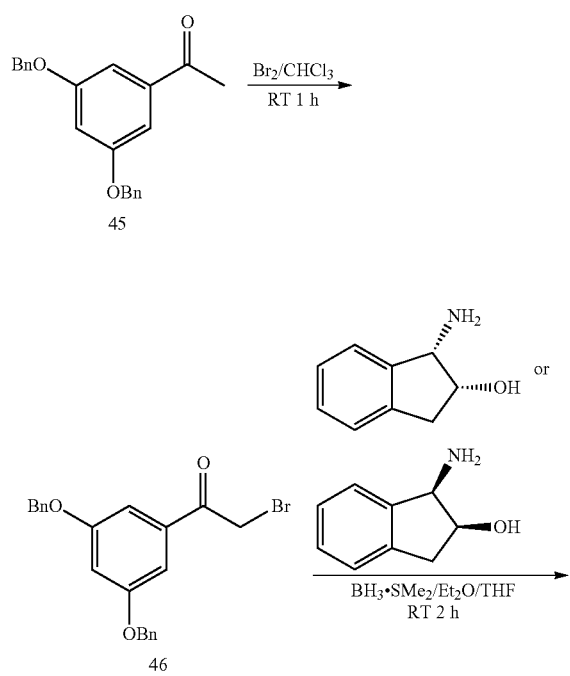

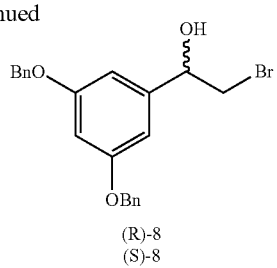

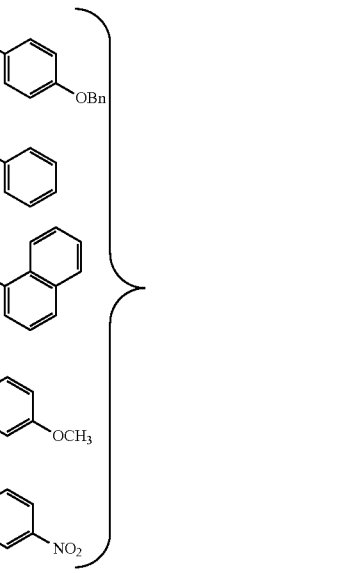

Example 5

Binding Affinities of Exemplary Fenoterol Analogues for β1 and β2 Adrenergic Receptors This example demonstrates that fenoterol analogues have an equivalent if not greater binding affinity for β2-ARs than fenoterol.

Compounds were tested up to three times each to determine their binding affinities at the β$_1$- and β$_2$-ARs. Competition curves with standard and unknown compounds included at least six concentrations (in triplicate). For each compound, graphs were prepared containing individual competition curves obtained for that test compound. IC$_{50}$ values and Hill coefficients were calculated using GraphPad Prism® software. K$_i$ values were calculated using the Cheng-Prusoff transformation (*Biochem Pharmacol* 22: 3099-3108, 1973). In each study, a standard compound was simultaneously run on the 96-well plate. If the standard compound did not have an IC$_{50}$ value close to the established average for that compound, the entire study was discarded and repeated again.

β$_1$-AR binding was done on rat cortical membrane following a previously described procedure (Beer et al., *Biochem. Pharmacol.* 37: 1145-1151, 1988). In brief, male Sprague-Dawley rats weighing 250-350 g were decapitated and their brains quickly removed. The cerebral cortices were dissected on ice, weighed and promptly transferred to a 50 ml test tube containing approximately 30 ml of 50 mM Tris-HCl, pH 7.8 (at room temperature). The tissues were homogenized with a polytron and centrifuged at 20,000×g for 12 mM at 4° C. The pellet was washed again in the same manner and resuspended at a concentration of 20 mg (original wet wt) per 1 ml in the assay buffer (20 mM Tris-HCl, 10 mM MgCl$_2$, 1 mM EDTA, 0.1 mM ascorbic acid at pH 7.8). To block the β$_2$ sites present in the cortical membrane preparation, 30 nM ICI 118-551 was also added to the assay buffer. To wells containing 100 μl of the test drug and 100 μl of [$^3$H]CGP-12177 (1.4 nM final concentration), 0.8 ml of tissue homogenate was added. After 2 hours at 25° C., the incubation was terminated by rapid filtration. Nonspecific binding was determined by 10 μM propranolol.

HEK 293 cells stability transfected with cDNA encoding human β$_2$-AR (provided by Dr. Brian Kobilka, Stanford Medical Center, Palo Alto, Calif.) were grown in Dulbecco's Modified Eagle Medium (DMEM) containing 10% fetal bovine serum (FBS), 0.05% penicillin-streptomycin, and 400 μg/ml G418 as previously described (Pauwels et al., *Biochem. Pharmacol.* 42: 1683-1689, 1991). The cells were scraped from the 150×25 mm plates and centrifuged at 500×g for 5 minutes. The pellet was homogenized in 50 mM Tris-HCl, pH 7.7, with a Polytron, centrifuged at 27,000×g, and resuspended in the same buffer. The latter process was repeated, and the pellet was resuspended in 25 mM Tris-HCl containing 120 mM NaCl, 5.4 mM KCl, 1.8 mM CaCl$_2$, 0.8 mM MgCl$_2$, and 5 mM glucose, pH 7.4. The binding assays contained 0.3 nM [$^3$H]CGP-12177 in a volume of 1.0 ml. Nonspecific binding was determined by 1 μM propranolol.

According to the above-described methods, binding affinities, expressed as K$_i$ values, were determined using membranes obtained from a HEK 293 cell line stably transfected with cDNA encoding human β2-AR (Pauwels et al., *Biochem. Pharmacol.* 42: 1683-1689, 1991) with [$^3$H] CGP-12177 as the marker ligand. The resulting IC$_{50}$ values and Hill coefficients were calculated for each test compound using GraphPad Prism® software and K$_i$ values were calculated using the Cheng-Prusoff transformation (*Biochem Pharmacol* 22: 3099-3108, 1973):

$$K_i = IC_{50}/(1+L/K_d)+$$  Eqn. 1.

Where: L is the concentration of [$^3$H]CGP-12177 and K$_d$ is the binding affinity of the [$^3$H]CGP-12177. Each test compounds was assayed three times.

Figure 4:
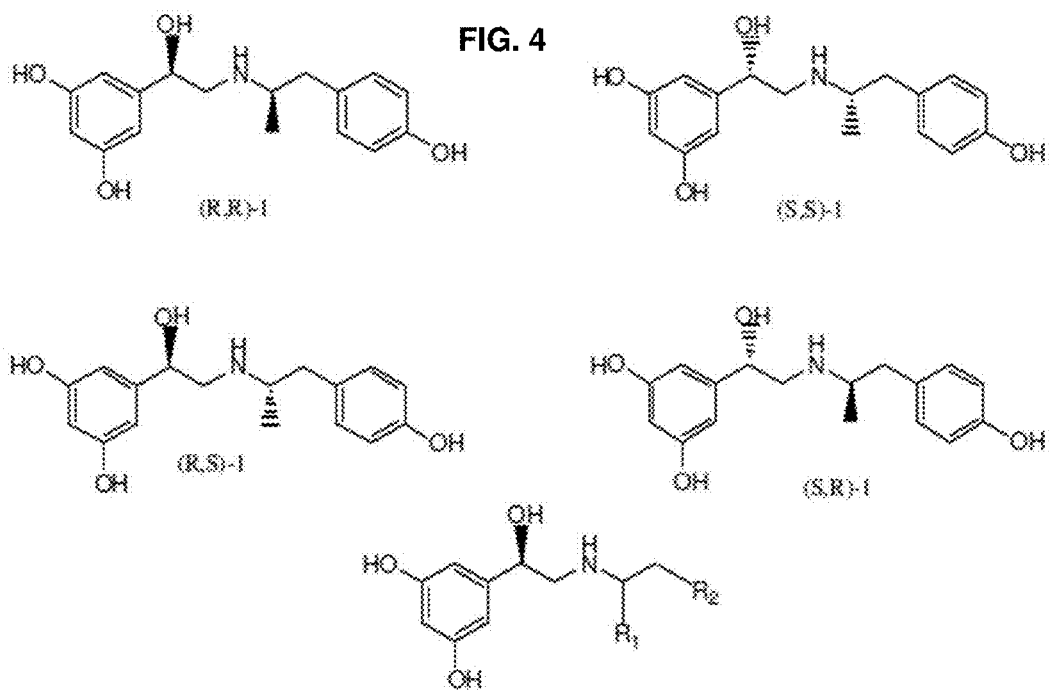
FIG. 4 illustrates the chemical structures of the stereoisomers of fenoterol and fenoterol analogs (compounds 2-7).

The relative binding affinities to the β$_2$-AR for the stereoisomers of compounds 1-4 and 6 were R,R>R,S>S, R≈S,S (FIG. 4; Table 1, below). This stereoselectivity is consistent with the previously reported potencies of the formoterol stereoisomers (Trofast et al., *Chiralty* 3: 443-450, 1991) and results from binding studies with the isoproterenol derivative PTFAM, compound 48, FIG. 5 (Eimerl et al., *Biochem. Pharmacol.* 36: 3523-3527, 1987). With compound 5, no significant difference was found between the values of the R,R and R,S isomers, thus the order was R,R=R,S>S,R>S,S. The K$_i$ value for (R)-7 was greater than that of (S)-7, which is consistent with the established enantioselective binding preference for β$_2$-ARs with the R-configuration at the stereogenic center containing the β-OH moiety, c.f. (Eimerl et al., *Biochem. Pharmacol.* 36: 3523-3527, 1987; Wieland et al., *Proc. Natl. Acad. Sci. USA* 93: 9276-9281, 1996; Kikkawa et al., *Mol. Pharmacol.* 53: 128-134, 1998; and Zuurmond et al., *Mol. Pharmacol.* 56: 909-916, 1999).

TABLE 1

The binding affinities to the β$_2$-AR of the compounds synthesized in this study calculated as K$_i$ ± SEM (nM), n = 3. Comparison of β$_1$- and β$_2$ adrenergic binding affinity of fenoterol isomers.

| Compound | K$_i$β$_1$ | K$_i$β$_2$ | K$_i$β$_1$/K$_i$β$_2$ |
|---|---|---|---|
| (R,R)-1 | 14750 ± 2510 | 345 ± 34 | 43 |
| (R,S)-1 | 18910 ± 2367 | 3695 ± 246 | 5 |
| (S,R)-1 | >100,000 | 10330 ± 1406 | NC |
| (S,S)-1 | >100,000 | 27749 ± 6816 | NC |
| (R,R)-2 | 21992 ± 3096 | 474 ± 35 | 46 |
| (R,S)-2 | 30747 ± 6499 | 1930 ± 135 | 16 |
| (S,R)-2 | 33378 ± 9170 | 5269 ± 509 | 6 |
| (S,S)-2 | >100,000 | 15881 ± 2723 | NC |
| (R,R)-3 | 24956 ± 2100 | 2934 ± 168 | 9 |
| (R,S)-3 | 31324 ± 3485 | 7937 ± 397 | 4 |
| (S,R)-3 | 77491 ± 3583 | 23125 ± 2093 | 3 |
| (S,S)-3 | 31440 ± 1681 | 28624 ± 906 | 1 |
| (R,R)-4 | 17218 ± 1270 | 1864 ± 175 | 9 |
| (R,S)-4 | 33047 ± 2779 | 6035 ± 434 | 4 |
| (S,R)-4 | >100,000 | 30773 ± 3259 | NC |
| (S,S)-4 | >100,000 | 28749 ± 1811 | NC |
| (R,R)-5 | 3349 ± 125 | 241 ± 38 | 14 |
| (R,S)-5 | 15791 ± 6269 | 341 ± 23 | 46 |
| (S,R)-5 | 34715 ± 9092 | 1784 ± 148 | 19 |
| (S,S)-5 | >100,000 | 2535 ± 209 | NC |
| (R,R)-6 | 10185 ± 499 | 9275 ± 902 | 1 |
| (R,S)-6 | >100,000 | 31440 ± 1681 | NC |
| (S,R)-6 | 61295 ± 5821 | >100,000 | NC |
| (S,S)-6 | 52609 ± 1434 | 56420 ± 5186 | 1 |
| (R)-7 | 42466 ± 3466 | 10466 ± 1461 | 4 |
| (S)-7 | 52178 ± 3006 | 20562 ± 3721 | 3 |

When just the (R,R) isomers were compared, (R,R)-5 had the highest relative affinity of the tested compounds, although the difference between (R,R)-5 and (R,R)-1 did not reach statistical significance, Table 1. The only other (R,R) stereoisomer with sub-micromolar affinity was (R,R)-2, which had a significantly lower binding affinity than (R,R)-5, p=0.0051, and (R,R)-1, p=0.0291, although the mean K$_i$ value for (R,R)-2 is only 23% greater than that of (R,R)-1. The minimal effect of transforming the p-OH moiety into a methyl ether is consistent with previous data from Schirrmacher et al. (*Bioorg. Med. Chem. Lett.* 13: 2687-92, 2003). In the previous study, rac-1 was converted into a [$^{18}$F]-fluoroethoxy ether without significant loss of in vitro activity and it was concluded that, within the accuracy of the test measurements, the derivatization did not change the binding affinity of the rac-1 to the β$_2$-AR.

Binding affinities, expressed as K$_i$ values, for the β$_1$-AR were determined using rat cortical membranes with [$^3$H]-CGP-12177 as the marker ligand (Beer et al., *Biochem. Pharmacol.* 37: 1145-1151, 1988.). The calculated K$_i$ for (R,R)-5 was 3,349 nM and the binding affinities for the all of the remaining test compounds were >10,000 nM, Table 1. Unlike the data from the β$_2$-AR binding studies, there was no clear trend which could be associated with the stereochemistry of the compounds.

The relative selectivity of the compounds for the β$_2$-AR and β$_1$-AR was determined using the ratio K$_i$β$_1$/K$_i$β$_2$, Table 1. Of particular interest were the ratios for the four compounds with sub-micromolar affinity for the β$_2$-AR, (R,R)-1, (R,R)-2, (R,R)-5 and (R,S)-5, which were 46, 43, 14 and 46, respectively. The results for (R,R)-1 and (R,R)-2 are consistent with previously reported K$_i$β$_1$/K$_i$β$_2$ ratio of 53 for the β$_2$-AR-selective agonist (R,R)-TA-2005, compound 49, FIG. 5.

The observed loss of β$_2$-AR selectivity for (R,R)-5 was unexpected as was the 3-fold increase in selectivity displayed by (R,S)-5 relative to (R,R)-5. Previous studies with the stereoisomers of 47 indicated that both the (R,R)- and (R,S)-isomers had a high degree of selectivity for the $\beta_2$-AR, relative to the $\beta_1$-AR, with the selectivity of the (R,R)-isomer greater than that of the (R,S)-isomer (Trofast et al., *Chirality* 3: 443-450, 1991). This is the case for compounds 1 and 2, but reversed for 5. It is also interesting to note that (S,R)-5 had a similar selectivity (19-fold) and its affinity for the $\beta_2$-AR was only 7-fold weaker than (R,R)-5, 1783 nM and 241 nM, respectively.

These studies demonstrate that (R,R)- or (R,S)-naphthyl fenoterol analogues have a higher binding affinity for $\beta$2-ARs than any isoform of fenoterol. The (R,R)-methyoxy fenoterol analogue has a similar $K_i$ for the $\beta$2-AR as (R,R)-fenoterol. Thus, such analogues are viable candidates for $\beta$2-AR agonists and can likely be used to treat disorders that are presently treated with commercially available (±)-fenoterol.

Example 6

Comparative Molecular Field Analysis

This example illustrates the use of Comparative Molecular Field Analysis (CoMFA) to analyze the disclosed compounds.

The disclosed compounds were analyzed using Comparative Molecular Field Analysis, a 3D QSAR technique applicable to the analysis of the relative activities of stereoisomers and/or enantiomers at a selected target.

CoMFA was performed as implemented in SYBYL 7.2. (TRIPOS Inc., St. Louis, Mo.). Molecular models of all derivatives were prepared in HyperChem v. 6.03 (HyperCube Inc., Gainesville, Fla.) using ModelBuild procedure to ensure the same conformation of the scaffold. Models were extracted to SYBYL and the partial atomic charges (Gasteiger—Huckel type) were calculated. Ligand models were aligned using as a common substructure of the two asymmetric carbon atoms in the core of the fenoterol molecule (—C*—CH$_2$—NH—C*—CH$_2$—). Two types of molecular fields (steric and electrostatic) were sampled on the grid (2 Å spacing) lattice surrounding each structure. Distance-dependent dielectric constant was used in electrostatic calculations and energetic cutoffs of 30 kcal/mol for both the steric and the electrostatic energies were set.

The Partial Least Square correlation procedure applied for resultant database extracted four statistically significant components and the following validation parameters were obtained for the best solution: $R^2$=0.920, F (4.21)=60.380, standard error of estimate=0.223, cross-validated (leave-one-out) $R^2$=0.847. In general, electrostatic fields account for 48.1% of explained variance and steric fields account for 51.9%. The resulting 3D QSAR model shows good statistical correlation with research data, $R^2$=0.920 and F=60.380, and good prediction power as indicated by the cross-validated $R^2$ value ($Q^2$)=0.847 and the standard error of prediction (SEP)=0.309, Table 2.

TABLE 2

The pK$_d$ predicted by the CoMFA model.

| Derivative | pKd Measured | pKd Predicted |
|---|---|---|
| (R,R)-1 | 6.46 | 5.84 |
| (R,S)-1 | 5.43 | 5.48 |
| (S,R)-1 | 4.99 | 5.02 |
| (S,S)-1 | 4.56 | 4.66 |
| (R,R)-2 | 6.32 | 6.17 |
| (R,S)-2 | 5.71 | 5.80 |
| (S,R)-2 | 5.28 | 5.34 |
| (S,S)-2 | 4.80 | 4.99 |
| (R,R)-3 | 5.53 | 5.57 |
| (R,S)-3 | 5.10 | 5.21 |
| (S,R)-3 | 4.64 | 4.75 |
| (S,S)-3 | 4.54 | 4.39 |
| (R,R)-4 | 5.73 | 5.58 |
| (R,S)-4 | 5.22 | 5.25 |
| (S,R)-4 | 4.51 | 4.75 |
| (S,S)-4 | 4.54 | 4.43 |
| (R,R)-5 | 6.62 | 6.72 |
| (R,S)-5 | 6.47 | 6.36 |
| (S,R)-5 | 5.75 | 5.90 |
| (S,S)-5 | 5.60 | 5.54 |
| (R,R)-6 | 5.03 | 5.01 |
| (R,S)-6 | 4.50 | 4.66 |
| (S,R)-6 | 4.00 | 4.19 |
| (S,S)-6 | 4.25 | 3.84 |
| (R)-7 | 4.98 | 5.33 |
| (S)-7 | 4.69 | 4.51 |

In the first stage, the model was used to identify the regions responsible for the discrimination between the stereoisomers. The CoMFA procedure produced several distinct asymmetric regions located in close proximity of each chiral center. The first chiral center (carrying the $\beta$ hydroxyl group) is surrounded by an electropositive region behind the molecule. An electropositive region can be associated with hydrogen bond formation and indicates favorable donor properties or unfavorable acceptor properties of the pseudoreceptor. In this case, the location of the electropositive field indicates that the orientation of the $\beta$-OH moiety behind the plane of the model (the S configuration at the chiral center) would hinder H bond formation with the receptor. The electropositive region is closely associated with a steric unfavorable region behind the first chiral center. This is an additional indication that the model demonstrates a preference for the $\beta$-hydroxyl group in the R configuration. The preference for the R configuration at this center is consistent with previous models and research data, which demonstrated that the R configuration is favored for functional activity at $\beta$-AR receptors (c.f., Eimerl et al., *Biochem. Pharmacol.* 36: 3523-3527, 1987; Wieland et al., *Proc. Natl. Acad. Sci. USA* 93: 9276-9281, 1996; Kikkawa et al., *Mol. Pharmacol.* 53: 128-134, 1998; and Zuurmond et al., *Mol. Pharmacol.* 56: 909-916, 1999).

The CoMFA model also demonstrated the effect of the second chiral center. The preferred configuration can be derived from the binding data, where for compounds 1-4 and 6 the (R,R)-isomers had the higher affinities relative to their respective (R,S)-isomers, while the values for (R,R)-5 and (R,S)-5 were equivalent, Table 1. Thus, in this model, the more active isomers are those with the methyl moiety on the stereogenic center on the aminoalkyl portion of the molecules pointing out of the plane of the figure of the CoMFA model. This is depicted by a steric disfavoring region behind the second chiral center of the molecule, and indicates a preference for the R configuration at this site.

In this study, only the aminoalkyl portion of the fenoterol molecule was altered and, therefore, the key CoMFA regions are associated with this aspect of the molecule. In the resulting analysis, all four interacting regions were identified in the proximity of the aromatic moiety and all can be used to generate hypotheses concerning the mode of binding action of the studied derivatives.

In the model, the large electropositive region encompassing the area close to the —OH or OCH$_3$ substituents represents H-bond donor properties of the pseudoreceptor to these moieties. These interactions are responsible for the relatively higher binding affinities of the O-derivatives, compounds 1 and 2, relative to compounds 3 and 4, in the latter compound the p-amino substituent should be positively charged under the test conditions.

A large electronegative region and another electropositive region, both located parallel on two sides of the aromatic system most likely represent π-π or π-hydrogen bond interactions between the β$_2$-AR and electron-rich aromatic moieties, such as the naphthyl ring. This is consistent with the increased affinity of compounds 1, 2 and 5 relative to the other compounds examined in this study. The role of this interaction is suggested by the observation that the values for (R,R)-5 and (R,S)-5 were equivalent to (R,R)-1 and (R,R)-2, Table 1.

Two steric regions are located close to the electrostatic regions and one favors and the other disfavors bulkiness in the respective areas. This indicates that the binding of the aminoalkyl portions of the molecules are also sterically restricted.

The binding of agonists and antagonists to the β$_2$-AR has been studied using site-directed mutagenesis and molecular modeling techniques (Eimerl et al., *Biochem. Pharmacol.* 36: 3523-3527, 1987; Wieland et al., *Proc. Natl. Acad. Sci. USA* 93: 9276-9281, 1996; Kikkawa et al., *Mol. Pharmacol.* 53: 128-134, 1998; Zuurmond et al., *Mol. Pharmacol.* 56: 909-916, 1999; Kontoyianni et al., *J. Med. Chem.* 39: 4406-4420, 1996; Furse et al., *J. Med. Chem.* 46: 4450-4462, 2003; and Swaminath et al. *J. Biol. Chem.* 279: 686-691, 2004). There is general agreement that the binding of the "catechol" portion of an agonist occurs within a binding area created by the transmembrane (TM) helices identified as TM3, TM5 and TM6. The binding process is a sequential event that produces conformational changes leading to G-protein activation (Furse et al., *J. Med. Chem.* 46: 4450-4462, 2003). A key aspect in this process is the interaction of the hydroxyl moiety on the chiral carbon of the agonist with the Asn-293 residue in TM6, and for this interaction an R-configuration is preferable at the chiral carbon (Eimerl et al., *Biochem. Pharmacol.* 36: 3523-3527, 1987; Kikkawa et al., *Mol. Pharmacol.* 53: 128-134, 1998; and Swaminath et al. *J. Biol. Chem.* 279: 686-691, 2004). Since the "catechol" portion of the fenoterol molecule was not altered in this study, it follows that in the CoMFA model, an R-configuration at the first stereogenic center is preferred in most stable complexes.

The majority of the binding and functional studies of β2-AR agonists have been conducted with small N-alkyl substituents such as methyl, isopropyl and t-butyl, c.f. (Kontoyianni et al., *J. Med. Chem.* 39: 4406-4420, 1996). However, while these compounds are active at the β$_2$-AR, they are not subtype selective. This is illustrated by the K$_i$β$_1$/K$_i$β$_2$ ratios determined for compounds 49, 50 and 51 (FIG. 5) which were 53, 1.7 and 1.3, respectively (Kikkawa, et al. *Mol. Pharmacol.* 53: 128-134, 1998). The removal of the p-methoxyphenyl moiety not only reduced the selectivity, but also the affinities as the respective β$_2$K$_i$ values were 12 nM, 170 nM and 6300 nM (Kikkawa, et al. *Mol. Pharmacol.* 53: 128-134, 1998).

The role that aminoalkyl substituents play in β$_2$-AR selectivity has been investigated using site-directed mutagenesis and molecular modeling techniques (Kikkawa, et al. *Mol. Pharmacol.* 53: 128-134, 1998; Furse et al., *J. Med. Chem.* 46: 4450-4462, 2003; and Swaminath et al. *J. Biol. Chem.* 279: 686-691, 2004). Using (R,R)-49 as the model ligand, Kikkawa, et al. determined that hydrogen bond formation between the p-methoxy oxygen on compound 49 and the hydroxyl group of tyrosine 308 (Y308) located in the extracellular end of TM7 was the source of the β$_2$-AR selectivity (*Mol. Pharmacol.* 53: 128-134, 1998).

Furse and Lybrand developed a de novo model of the β$_2$-AR and investigated molecular complexes of several ligands (agonist and antagonist) with this subtype (*J. Med. Chem.* 46: 4450-4462, 2003). Among the structures investigated, (R,R)-49 has the same aminoalkyl substituent as the compound 2. Examination of the (R,R)-49/β$_2$-AR complex revealed that the p-methoxy group oxygen of (R,R)-49 formed a hydrogen bond with the hydroxy group of Y308, which supports the model proposed by Kikkawa, et al. (*Mol. Pharmacol.* 53: 128-134, 1998). The distance between the two oxygen atoms bonded in the model was 3.22 Å. However, the methoxy moiety of the ligand was also located in close proximity to three other polar residues, histidine 296 (H296) in TM6, tryptophan 109 (W109) in TM3 and asparagine 312 (N312) in TM7, each of which can interact with an aromatic group on the aminoalkyl portion of (R,R)-49.

In the Furse and Lybrand model, the distance between the oxygen atom of the ligand and the hydrogen atom of H296 was 5.88 Å and H296 was proposed as an alternative hydrogen bond donor for interaction with the methoxy group of (R,R)-49. Since Y308 and H296 are found only in β$_2$-AR, the corresponding residues found in the β$_1$-AR are F359 and K347, respectively, the interaction with H296 and Y308 has been proposed as the source of β$_1$/β$_2$ selectivity (Furse et al., *J. Med. Chem.* 46: 4450-4462, 2003).

Since the previous studies of β$_1$/β$_2$ selectivity utilized (R,R)-49, the subtype selectivity of the (R,R)-stereoisomers of the compounds synthesized in our study were compared to the subtype selectivity of (R,R)-49. The data from this study suggest that hydrogen bond formation between Y308 and/or H296 and the oxygen atom on the p-substituent of the agonist is involved in β$_2$-AR selectivity. The interaction is possible with (R,R)-1 and (R,R)-2 and the K$_i$β$_1$/K$_i$β$_2$ ratios for these compounds are 43 and 46, respectively, which are comparable to the K$_i$β$_1$/K$_i$β$_2$ ratio of 53 determined for (R,R)-49. The K$_i$β$_1$/K$_i$β$_2$ ratios for compounds 3, 4, 6 and 7 were <10 and reflect the fact that they do not have the ability to form hydrogen bonds with Y308 or H296. The hydrogen bonding interactions were also suggested by the CoMFA model identifying a large electropositive region surrounding the area close to the —OH or —OCH$_3$ substituents, representing hydrogen-bond donor properties of the pseudoreceptor.

The data from this study also suggest that an aromatic moiety on the aminoalkyl portion of the compound contributes to K$_i$ and subtype selectivity, even if the aromatic moiety is unable to form a hydrogen bond with the receptor. This is demonstrated by the comparison of the K$_i$β$_2$ values for the (R,R)-isomers of compounds 1-5 which were <3,000 nM with K$_i$β$_2$ value of (R,R)-6 which was 9,000 nM and the K$_i$β$_1$/K$_i$β$_2$ ratios which were ≥9 for 1-5 while compound 6 displayed no subtype selectivity, Table 1. One possible mechanism to explain the data is π-hydrogen bond formation. The cloud of π-electrons of aromatic rings can act as hydrogen bond acceptors, although it has been estimated that the interaction would be about half as strong as a normal hydrogen bond (Levitt and Perutz, *J. Mol. Biol.* 201: 751-754, 1998). The higher affinity and subtype selectivity for (R,R)-5 relative to (R,R)-3 and (R,R)-4 or (R)-7 is consistent with the greater π electron distribution in the napthyl ring relative to the other aromatic rings.

The CoMFA model also identified a large electronegative region and another electropositive region, both located parallel to the aromatic system, which are most likely associated with π-π or π-hydrogen bond interactions between the β$_2$-AR and electron-rich aromatic moieties, such as the naphthyl ring. Using the model developed by Furse and Lybrand with (R,R)-49 as the interacting ligand, Y308, H296, W109 and N312 were identified as possible sources of π-π and/or π-hydrogen bond interactions. In the β$_2$-AR model, the estimated distances between the p-methoxy moiety on (R,R)-49 and W109 and N312 were 4.80 Å and 3.45 Å, respectively. Since W109 and N312 are fully conserved in all β-AR subtypes, the interactions suggested by the CoMFA model may represent the source of the increase affinities for (R,R)-1, (R,R)-2 and (R,R)-5, relative to the other (R,R)-isomers, but not the observed β$_1$/β$_2$ selectivity.

The data from this study and the resulting CoMFA model indicate that the binding process of the tested compounds with the β$_2$-AR includes the interaction of the chiral center on the aminoalkyl portion of the agonist with a sterically restricted site on the receptor. The existence of a sterically restricted site has been previously suggested from the data obtained in the development of 3D models for agonist and antagonist complexes with the β$_2$-AR (Kobilka, *Mol. Pharm.* 65: 1060-1062, 2004). For example, (R,R)-49 and similar compounds with substituents larger than a methyl group at the stereogenic center on the aminoalkyl portion were suggested to produce significant steric interactions that would unfavorably affect the ligand-receptor complexes.

The binding of an agonist to the β$_2$-AR has been described as a multistep interrelated process, in which sequential interactions between the agonist and receptor produce corresponding conformational changes (Kobilka, *Mol. Pharm.* 65: 1060-1062, 2004). The CoMFA model reflects the final agonist/β$_2$-AR complex and, in order to discern the effect of the steric restricted site, it is necessary to consider the effect that interaction with this site has on the outcome of the binding process. A detailed description of the present CoMFA model is disclosed in Jozwiak et al. (*J. Med. Chem.*, 50 (12): 2903-2915, 2007) which is hereby incorporated by reference in its entirety.

If one assumes that the interaction of the "catechol" portion of the agonist with the binding area created by TM3, TM5 and TM6 (the first binding area), then these interactions will fix the position of the aminoalkyl portion of the agonist relative to the steric restricted site, and perhaps even create this site. In the CoMFA model, the steric restrictions at the site force the methyl moiety at the chiral center of the aminoalkyl portion to point out of the plane of the model.

Due to the free rotation about the N-atom, the configuration at the chiral center bearing the methyl moiety may likely not affect the ability of the molecule to minimize the interaction with the steric restricted site. However, in the minimum energy conformation, e.g., with the methyl group pointing out of the plane of the CoMFA model, the orientation of the remaining segment of the aminoalkyl portion relative to the second binding area would be affected by the stereochemistry. Indeed, R and S configurations would produce mirror image relationships to the second binding area. This situation is illustrated in FIG. 4 where the catechol, first chiral center and the methyl moieties of (R,R)-5 and (R,S)-5 have been overlaid upon each other.

The studies elucidating the source of β$_2$-AR selectivity have primarily utilized (R,R)-49 and one previous study of the effect of chirality on subtype selectivity reported that (R,R)-47 had a higher β$_2$-AR selectivity than (R,S)-47 (Trofast et al., *Chirality* 3: 443-450, 1991). Thus, the observed equivalent affinities and functional activities of (R,R)-5 and (R,S)-5 at the β$_2$-AR and the 3-fold increased β$_2$-AR selectivity of (R,S)-5 was an unexpected result. One possible explanation of these results is that the naphthyl moiety of (R,S)-5 does not interact with the site defined by Y308 and H296 and is directed towards and binds to another site on the β$_2$-AR. This interaction also conveys or participates in subtype selectivity as well as increased binding affinity and agonist activity. Since the previous models of β$_2$-AR selectivity only employed (R,R)-isomers, it is possible that this site has been overlooked.

Another explanation of the data is suggested by the "rocking tetrahedron" chiral recognition mechanism proposed by Sokolov and Zefirov (*Doklady Akademii Nauk SSSR* 319: 1382-1383, 1991). In this approach to molecular chiral recognition, the enantiomeric ligands are secured to a chiral selector by two binding interactions. The interactions must be non-equivalent and directional so that only one orientation is possible. The tethered enantiomers still have conformational mobility and the remaining moieties on the chiral center will sweep out overlapping but not identical steric volumes. Where and to what extent the chiral selector interacts with these steric volumes, determines the enantioselectivity of the process. If the chirality of the chiral selector places the interaction perpendicular to the plane of the ligand, no enantioselectivity is observed. As a deviation from the perpendicular increases, so does the enantioselectivity relative to the R or S configuration.

With (R,R)-5 and (R,S)-5, the interactions with the first binding area and the steric restricted site of the CoMFA model are two non-equivalent and directional interactions that place the remaining constituents on the second chiral center in the same, albeit mirror image, orientation relative to the second binding area. As discussed above, the interactions of the 1-napthyl moieties of compound 5 with Y308 and H296 are believed to be the source of the observed β$_2$-AR selectivity. If the 1-naphthyl rings sweep out overlapping but not identical steric volumes, then the observed $K_i β_2$ values and subtype selectivity indicate the following: 1) the $K_i β_2$-AR values represent the sum total of the π-hydrogen bond and π-π interactions between the 1-naphthyl moieties and Y308 and H296, as well as additional non-β$_2$-AR specific interactions with other residues such as W109 and N312; 2) the steric volume swept out by (R,S)-5 increases the probability of interactions of Y308 and H296 with the π cloud of the naphtyl moiety relative to the (R,R)-5; and 3) the steric volume swept out by (R,R)-5 increases the probability of interactions with non-β$_2$-AR specific sites relative to (R,S)-5.

The effect of the configuration at the second chiral center and conformational-based chiral selectivity is also illustrated by the affinities and subtype selectivities of (R,R)-3, (R,S)-3 and (R)-7, Table 1. The inversion of the chirality at the second chiral carbon from R to S, reduced the $K_i β_2$ value of the (R,S)-3/β$_2$-AR complex relative to the (R,R)-3/β$_2$-AR complex by ~3-fold while there was no significant difference between their $K_i β_1$ values. The increased subtype selectivity observed for (R,R)-3 relative to (R,S)-3, 9 versus 4, respectively, essentially reflects the differences in $K_i β_2$ values, which could be a reflection of increased conformational energy required to bring the aromatic portion of the aminoalkyl chain into contact with the electropositive and electronegative regions that comprise the second binding area or a decrease in the probability that this interaction would occur.

The removal of the methyl moiety on the second chiral center, and thereby the chirality at this site ((R)-7), had a similar effect as inverting the chirality at this site from R to S. The $K_i\beta_2$ values for (R)-7 was 32% higher than (R,S)-3 and there was no difference in the $\beta_2$-AR selectivity, Table 1. These results suggest that for compound 3, the primary effect of the R configuration at the second chiral site was to direct the aminoalkyl chain towards the second binding area which increased the probability of interacting with this site and reduces the conformational energy required to achieve this interaction.

A difference between compounds 3 and 5 is the steric areas swept out by the aromatic substituents. In the case of compound 3, the phenyl ring produces a smaller, more linear area, while with compound 5, the 1-naphthyl ring system produces a relatively larger and broader area. These differences can be used to guide the synthesis of additional derivatives.

In an example, (R,R)-2 and (R,S)-5 are chosen as possible candidates for the development of a new selective $\beta_2$-AR agonist. These compounds may have increased and extended systemic exposures relative to the commercially available rac-1 due to changes in molecular hydrophobicity, metabolic profile and transporter interactions.

The present example provides a pharmacophore model which may be used as a structural guide for the design of new compounds with $\beta_2$-AR selectivity which can be tested for use in the treatment of a desired condition, including congestive heart failure.

Example 7

Pharmacokinetic studies of (R,R)-fenoterol, (R,R)-methoxyfenoterol and (R,S)-naphthylfenoterol This example demonstrates the plasma concentrations of (R,R)-fenoterol, (R,R)-methoxyfenoterol and (R,S)-naphthylfenoterol administered as an intravenous (IV) bolus to male Sprague-Dawley rats.

(R,R)-fenoterol, (R,R)-methoxyfenoterol and (R,S)-naphthylfenoterol were administered to jungular vein cannulated (JVC) rats at a single dosage of 5 mg/ml intravenously (see Table 3). Dose calculations (mg/kg) were based on the individual body weight measured on the day of treatment. Study duration for pharmacokinetic studies was 6 hours. Plasma samples were collected over six hours at the following nine timepoints: prior to administration of the desired dose; 5.00-5.30 minutes after dose; 15.00-16.30 minutes after dose; 30.00-33.00 minutes after dose; 60-65 minutes after dose; 120-125 minutes after dose; 240-245 minutes after dose; 300-305 minutes after dose; and 360-365 minutes after dose. Urine was collected for 0-6 hours and 6 to 24 hours from 3 rats in each treatment group.

TABLE 3

Study conditions for measuring plasma concentrations of (R,R)-fenoterol, (R,R)-methoxyfenoterol and (R,S)-naphthylfenoterol.

| Compound: | Dose level (mg/kg): | Dose Concentration (mg/ml): | No. of Rats: | No. of Rats for plasma analysis: |
|---|---|---|---|---|
| (R,R)-fenoterol | 5 | 2.5 | 6 | 5 |
| (R,R)-methoxyfenoterol | 5 | 2.5 | 6 | 5 |
| (R,S)-naphthylfenoterol | 5 | 2.5 | 6 | 2 |

Pharmacokinetic parameters for (R,R)-fenoterol, (R,R)-methoxyfenoterol and (R,S)-naphthylfenoterol after intravenous administration to rats (5 mg/kg) were analyzed according to a two-compartment open model (see Table 4). A drug that follows the pharmacokinetics of a two-compartment model does not equilibrate rapidly throughout the body, as is assumed for a one-compartment model. In the two-compartment model, the drug distributes into two compartments, the central compartment and the tissue, or peripheral compartment. The central compartment represents the blood, extracellular fluid, and highly perfused tissues. The drug distributes rapidly and uniformly in the central compartment. A second compartment, known as the tissue or peripheral compartment, contains tissues in which the drug equilibrates more slowly. Drug transfer between the two compartments is assumed to take place by first-order processes.

The following abbreviations are utilized in Table 4 below: alpha—macro rate constant associated with the distribution phase; beta—macro rate constant associated with the elimination phase; A, B—zero time intercept associated with the alpha phase and beta phase, respectively; AUC—area under the curve; T1/2 (K10)—half-life associated with the rate constant K10; K10—elimination rate—rate at which the drug leaves the system from the central compartment; K12—rate at which drug enters tissue compartment from the central compartment; K21—rate at which drug enters central compartment from tissue compartment; V1—volume of distribution of the central compartment; V2—volume of distribution of the tissue compartment; Vss—volume of distribution at steady state; and Cl—clearance.

TABLE 4

Pharmacokinetic parameters for (R,R)-fenoterol, (R,R)-methoxyfenoterol and (R,S)-naphthylfenoterol after intravenous administration to rats (5 mg/kg).

| Parameter | Units | (R,R)-fenoterol (n = 2) Weight 306 ± 11 | (R,R)-methoxyfenoterol (n = 5) Weight 296 ± 8 | (R,S)-naphthylfenoterol (n = 5) Weight 297 ± 10 |
|---|---|---|---|---|
| | | Two-compartment open model | | |
| A | µg/ml | 1.6300 | 4.6437 | 4.0365 |
| Alpha | 1/min | 0.0710 | 0.1982 | 0.1764 |
| B | µg/ml | 0.0577 | 0.3900 | 0.4372 |
| Beta | 1/min | 0.0086 | 0.0054 | 0.0046 |
| AUC | min*µg/ml | 29.6861 | 96.1011 | 116.88 |
| T½ (K10) | min | 12.19 | 13.23 | 18.11 |
| K10 | 1/min | 0.0568 | 0.0524 | 0.0383 |
| K12 | 1/min | 0.0119 | 0.1309 | 0.1213 |
| K21 | 1/min | 0.0107 | 0.0203 | 0.0214 |
| V1 | ml | 906.5 | 294.01 | 330.83 |
| V2 | ml | 1005.20 | 1895.00 | 1872.92 |
| Vss | ml | 1911.70 | 2189.02 | 2203.75 |
| Cl | ml/min | 51.54 | 15.40 | 12.66 |

Tables 5-7 illustrate the individual plasma concentrations of (R,R)-fenoterol, (R,R)-methoxyfenoterol and (R,S)-naphthylfenoterol after IV administration to rats (5 mg/kg). The average concentration of (R,R)-fenoterol in plasma was dramatically lower (1.34 µg/ml) five minutes after IV administration to rats (5 mg/kg) compared to either the average concentration of (R,R)-methoxyfenoterol (2.12 µg/ml) or (R,S)-naphthylfenoterol (2.11 µg/ml).

TABLE 5

Individual plasma concentrations of (R,R)-fenoterol after intravenous administration (5 mg/kg).

| | Concentration (ug/ml) | | |
|---|---|---|---|
| Time (min) | Rat# 01 | Rat #02 | Average |
| 5 | | 1.34 | 1.34 |
| 15 | | 0.36 | 0.36 |
| 30 | 0.17 | 0.50 | 0.34 |
| 60 | 0.05 | 0.05 | 0.05 |
| 120 | 0.03 | 0.01 | 0.02 |
| 240 | 0.0003 | 0.02 | 0.01 |
| 300 | | 0.005 | 0.005 |
| 360 | 0.08 | 0.03 | 0.06 |

TABLE 6

Individual plasma concentrations of (R,R)-methoxyfenoterol after intravenous administration (5 mg/kg).

| | Concentration (ug/ml) | | | | | |
|---|---|---|---|---|---|---|
| Time (min) | Rat# 13 | Rat# 14 | Rat# 15 | Rat# 16 | Rat# 18 | Average |
| 5 | 1.94 | | 2.14 | 2.51 | 1.89 | 2.12 |
| 15 | 0.48 | 0.54 | 0.62 | 0.67 | 0.56 | 0.58 |
| 30 | 0.31 | 0.40 | 0.46 | 0.48 | 0.38 | 0.41 |
| 60 | 0.23 | 0.25 | 0.24 | 0.33 | 0.25 | 0.26 |
| 120 | 0.14 | 0.16 | 0.18 | 0.21 | 0.14 | 0.17 |
| 240 | 0.09 | 0.12 | 0.17 | 0.14 | 0.08 | 0.12 |
| 300 | 0.06 | 0.07 | 0.07 | 0.09 | 0.07 | 0.07 |
| 360 | 0.05 | 0.06 | 0.05 | 0.08 | 0.04 | 0.06 |

TABLE 7

Individual plasma concentrations of (R,S)-naphthylfenoterol after intravenous administration (5 mg/kg).

| | Concentration (ug/ml) | | | | | |
|---|---|---|---|---|---|---|
| Time (min) | Rat# 25 | Rat# 26 | Rat# 27 | Rat# 28 | Rat# 29 | Average |
| 5 | | 2.52 | 2.16 | 1.64 | 2.10 | 2.11 |
| 15 | | 0.85 | 0.78 | 0.50 | 0.60 | 0.68 |
| 30 | 0.49 | | 0.54 | 0.34 | 0.33 | 0.43 |
| 60 | 0.36 | 0.42 | 0.37 | 0.29 | 0.24 | 0.34 |
| 120 | 0.25 | 0.29 | 0.26 | 0.22 | 0.18 | 0.24 |
| 240 | 0.11 | 0.11 | 0.13 | 0.13 | 0.11 | 0.12 |
| 300 | 0.10 | 0.11 | 0.12 | 0.11 | 0.10 | 0.11 |
| 360 | 0.08 | 0.08 | 0.11 | 0.10 | 0.09 | 0.09 |

The data demonstrate that the two derivatives, (R,R)-methoxyfenoterol and (R,S)-naphthylfenoterol, have a significantly higher systemic exposure (AUC) and longer clearance compared to (R,R)-fenoterol which may produce a longer acting drug. It is suggested that the longer clearance time may be the result of inhibiting glucuronidation.

Example 8

Inhibition of 1321N1 Astrocytoma Cell Growth by (R,R)-fenoterol, Specific Fenoterol Analogues or Combination Thereof This example demonstrates the ability of fenoterol and specific fenoterol analogues disclosed herein to inhibit 1321N1 astrocytoma cell growth in vitro and in vivo.

The possibility that selective $\beta_2$-AR ($\beta_2$-AR) agonists could affect the growth of gliomas and astrocytomas through the direct stimulation of cAMP and/or associated pathways was determined Previous studies demonstrated that $\beta_2$-AR are expressed in glioblastomas, either maintained as established cell lines or primary cultures derived from human biopsies as well in the human-derived 1321N1 astrocytoma cell line. In the current study, the U87MG cell line was used as a negative control as there was no detectable expression of the $\beta_2$-AR in these cells and the sensitivity of the U87MG cell line to increased cAMP levels has been previously established. The general structure and agonists used in this Example are provided below.

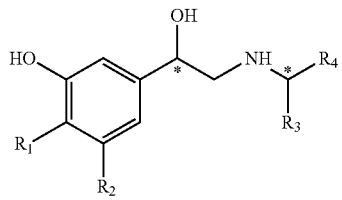

| Name | $R_1$ | $R_2$ | $R_3$ | $R_4$ |
|---|---|---|---|---|
| Isoproterenol | —OH | —H | —$CH_3$ | —$CH_3$ |
| Fenoterol | —H | —OH | —$CH_3$ | (4-hydroxyphenyl)ethyl |
| Methoxyfenoterol | —H | —OH | —$CH_3$ | (4-methoxyphenyl)ethyl |

-continued

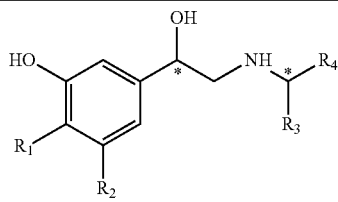

| Name | R₁ | R₂ | R₃ | R₄ |
|---|---|---|---|---|
| 1-naphthylfenoterol | —H | —OH | —CH₃ | (1-naphthyl-ethyl) |
| 2-naphthylfenoterol | —H | —OH | —CH₃ | (2-naphthyl-ethyl) |
| 4-methoxy-1-naphthylfenoterol | —H | —OH | —CH₃ | (4-methoxy-1-naphthyl-ethyl) |
| Ethylfenoterol | —H | —OH | —CH₂CH₃ | (4-hydroxyphenyl-ethyl) |
| 4-methyloxy-ethylfenoterol | —H | —OH | —CH₂CH₃ | (4-methoxyphenyl-ethyl) |

HEK cells transfected with human $\beta_2$-AR (HEK-$\beta_2$-AR, provided by Dr. Brian Kobilka, Stanford Medical Center, Palo Alto, Calif.) were grown in Dulbecco's Modified Eagle Medium (DMEM) containing 10% fetal bovine serum (FBS) and 0.05% penicillin-streptomycin with 400 μg/ml G418. The 1321N1 astrocytoma cell line was obtained from European Collection of Cell Cultures (Sigma-Aldrich, St. Louis, Mo.) and the U87MG cells from American Type Culture Collection (Manassas, Va.). The cells were cultured in DMEM supplemented with 10% FBS. Drug treatments were carried out when cells were 70-80% confluent.

Binding to cell membranes obtained from 1321N1 cells was conducted in a 96-well format, as described previously (Jozwiak et al., J. Med. Chem. 50: 2903-2915, 2007). In brief, the cells were scraped from the 150×25 mm plates and centrifuged at 500×g for 5 minutes. The cell pellet was washed twice, homogenized in Tris-HCl [50 mM, pH 7.7] and the crude membranes were recovered by centrifugation at 27,000×g for 10 mM The pellet was resuspended in Tris-HCl [25 mM, pH 7.4] containing 120 mM NaCl, 5.4 mM KCl, 1.8 mM CaCl₂, 0.8 mM MgCl₂, and 5 mM glucose. The binding assays contained 0.3 nM [³H]CGP-12177 in a volume of 1.0 mL, and samples were conducted in triplicate. Nonspecific binding was determined using 1 μM propranolol. Total volume of incubation was 1.0 mL and samples were incubated for 60 mM at 25° C. The amount of protein in the binding assay was 270 μg. The reaction was terminated by filtration using a Tomtec 96 harvester (Orange, Conn.) through glass fiber filters. Bound radioactivity was counted on a Pharmacia Biotech beta-plate liquid scintillation counter (Piscataway, N.J.) and expressed in counts per minute. IC₅₀ values were determined using at least six concentrations of each fenoterol analog, and calculated using Graphpad/Prism (ISI, San Diego, Calif.). The $K_i$ values were determined by the method of Cheng and Prusoff.

$\beta_2$-AR mediated cAMP accumulation was determined as described previously (Jozwiak et al., J. Med. Chem. 50: 2903-2915, 2007). HEK-$\beta_2$-AR, 1321N1 or U87MG cells were plated in 96-well plates. When the cells reached confluence, the medium was removed and each well rinsed with 0.1 mL of Krebs-HEPES buffer (130 mM NaCl, 4.8 mM KCl, 1.2 mM KH₂PO₄, 1.3 mM CaCl₂, 1.2 mM MgSO₄, 25 mM HEPES, and 10 mM glucose, pH 7.3). The plates were preincubated for 10 minutes at room temperature with buffer alone; then test compound diluted in buffer was added to the wells for quadruplicate determinations. The plates were incubated for an additional 10 minutes with the test compound. After incubation, the medium was removed and 0.1 mL of 0.5 M formic acid was added. After a minimum of 1 hour, the supernatant was removed and lyophilized. cAMP was quantitated using the protein kinase binding assay of Gilman. The amount of protein per well was determined using the BCA protein determination kit (Thermo Scientific Pierce, Rockford, Ill.) and was used to calculate the amount of cAMP/mg/well.

To measure $\beta_2$-AR mediated inhibition of mitogenesis, HEK-$\beta_2$-AR, 1321N1 or U87MG cells were seeded in a 96-well plate at approximately 5,000 cells/well. After 48 hours, the wells were rinsed twice and the medium was replaced with fresh medium containing 10 µL of drug in sterile water. After another 24 hours of incubation at 37° C., 0.25 µCi of [$^3$H]-thymidine was added to each well. The cells were incubated for an additional 2 hours at 37° C., at which point 10 µL of 10× trypsin was added, and the resuspended cells were harvested using a Tomtec 96 harvester through glass fiber filters. DNA-associated radioactivity was the plate was counted as described above.

Cell cycle distribution was analyzed by flow cytometry. Briefly, cells were trypsinized, washed with phosphate-buffered saline (PBS) and fixed with 95% ethanol at −20° C. for 24 hours. Fixed cells were washed with PBS, treated with 0.05% RNase for 30 minutes at 37° C. and stained with propidium iodide. The stained cells were analyzed using a FACScan laser flow cytometer (FACSCaliber, BD Biosciences).

Proteins were separated by 4-12% pre-cast gels (Invitrogen, Carlsbad, Calif.) using sodium dodecyl sulfate (SDS)-polyacrylamide gel electrophoresis and then electrophoretically transferred onto Hybond™-P membrane (Amersham Biosciences, Piscataway, N.J.). Blots were probed with the following antibodies: Cyclin D1 (sc-246, mouse polyclonal IgG), Cyclin A (sc-596, rabbit polyclonal IgG), p27 (sc-528, Rabbit polyclonal IgG) and Actin (sc=1616, goat polyclonal IgG) all purchased from Santa Cruz Biotechnology (Santa Cruz, Calif.) and p-Akt (Ser473, rabbit polyclonal IgG) purchased from Cell Signaling Technology (Beverly, Mass.). The ECL Plus Western Blotting Detection System of Amersham Biosciences (Piscataway, N.J.) and the procedure recommended by the manufacturer were used for the detection of antigens. Protein bands were quantified by analyzing the images obtained using an Alphaimager™ S-3400 (Alpha Innotech Corp., San Leandro, Calif.).

(R,R)-Fenoterol and the fenoterol analogues (Table 8) were synthesized as described herein (also described in U.S. patent application Ser. No. 12/376,945 filed Feb. 9, 2009, Jozwiak et al., *J. Med. Chem.*, 50: 2904-2915, 2007 and Jozwiak et al., *Bioorg. Med. Chem.*, 18: 728-736, 2010 each of which is incorporated by reference in its entirety). [$^3$H]-CGP-12177 was purchased from PerkinElmer (Shelton, Conn.), DMEM was purchased from Lonza Walkersville, Inc. (Walkersville, Md.), FBS was purchased from Atlas Biologicals (Fort Collins, Colo.), Penicillin-Streptomycin and Geneticin (G418) were purchased from Invitrogen (Carlsbad, Calif.), NaCl and CaCl$_2$ were purchased from Mallinckrodt (Phillipsburg N.J.) and (±)-propranolol, (R)-isoproterenol, forskolin, Tris-HCl, Trizma Base, PBS, KCl, MgSO$_4$, MgCl$_2$, D-(+)-glucose, KH$_2$PO$_4$ and HEPES were purchased from Sigma-Aldrich (St. Louis, Mo.).

Initial RT-PCR studies indicated that $\beta_2$-AR was expressed in 1321N1 cells while $\beta_1$-AR was not. The expression of $\beta_2$-AR in 1321N1 cells was confirmed using displacement studies with [$^3$H]CGP-12177 as the marker ligand. Saturation studies determined that the binding affinity ($K_d$ value) of CGP-12177 was 0.23 nM. The expression level of the $\beta_2$-AR ($B_{max}$) in the 1321N1 cellular membranes was 32 fmol/mg of protein. The $\beta_2$-AR selective antagonist ICI 118-551 bound to the membranes with high affinity ($K_d$=0.58 nM) and a Hill coefficient of ~1.0 indicating a single binding site. There was no observable binding of [$^3$H]CGP-12177 to the membranes obtained from U87MG cells indicating that the $\beta_2$-AR is not expressed in this cell line.

Figure 6:
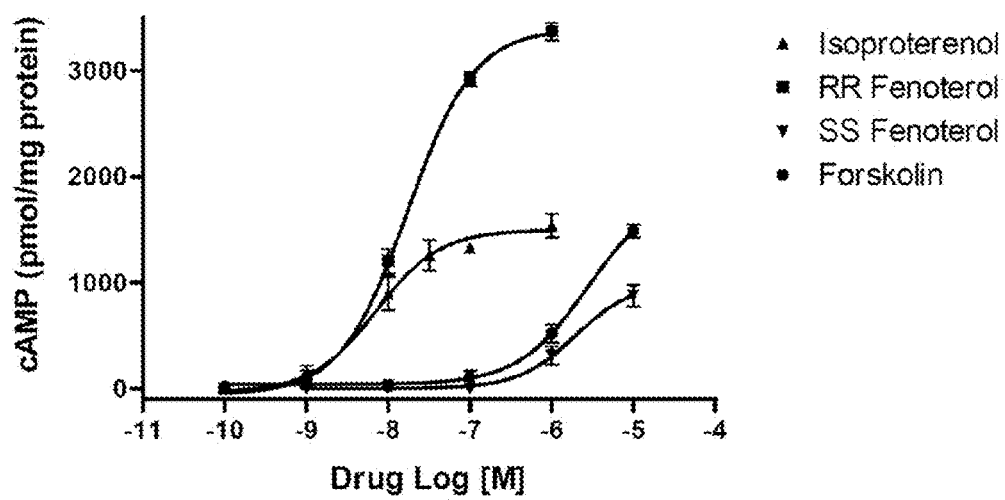
FIG. 6 illustrates dose-dependent stimulation of cAMP accumulation by fenoterol analogs. (R,R)-fenoterol (■) is a full agonist for stimulation of cAMP accumulation in 1321N1 cells, exhibiting greater stimulation of cAMP than the standard isoproterenol (●) or forskolin (▲). (S,S)-fenoterol (♦) was determined to be a partial agonist in these cells.

The agonist-induced cAMP accumulation in 1321N1 cells was studied using (R)-isoproterenol and selected fenoterol derivatives. Each of the agonists with an R-configuration at the β-hydroxy carbon atom produced a significant increase in cAMP production, FIG. 6. The calculated $EC_{50cAMP}$ value for (R)-isoproterenol was 16.5 nM). The $EC_{50cAMP}$ values for the fenoterol analogs ranged from 13.5 nM to 88.24 nM, Table 8. However, only (R,R)-fenoterol and (R,R)-methoxyfenoterol were full agonists producing maximal cAMP accumulations of >100% relative to (R)-isoproterenol, while the cAMP accumulations produced by (R,R)-4-methoxy-1-naphthylfenoterol, (R,S)-4-methoxy-1-naphthylfenoterol and (S,S)-fenoterol were 35%, 53%, and 31%, respectively. The induced cAMP accumulation produced by these compounds was blocked by the addition of 1 µM propranolol and ICI 118-551 competitively antagonized the agonist activity of (R,R)-fenoterol, pA2=8.9 with a slope of −1.24±0.30.

TABLE 8

The activity of (R)-isoproterenol and fenoterol analogs presented as IC$_{50}$ values associated with the inhibition of [$^3$H]-thymidine incorporation in 1321N1 cells, stimulation of cAMP accumulation presented as $EC_{50cAMP}$ determined in 1321N1 and HEK-$\beta_2$-AR cells. The IC$_{50}$ and $EC_{50cAMP}$ values determined in 1321N1 cells are presented as mean ± SD for n = 4.

| Compound | Mitogenesis Inhibition IC$_{50}$ (nM) | Stimulation of cAMP Accumulation 1321N1 $EC_{50cAMP}$ (nM) | Stimulation of cAMP Accumulation HEK-$\beta_2$-AR $EC_{50cAMP}$ (nM) |
|---|---|---|---|
| (R)-isoproterenol | 0.05 ± 0.01 | 16.45 ± 6.14 | 0.2[a] |
| (R,R)-fenoterol | 0.14 ± 0.07 | 15.91 ± 2.04 | 0.3[a] |
| (R,S)-fenoterol | 6.09 ± 1.93 | | 4.7[a] |
| (S,R)-fenoterol | 6.74 ± 2.18 | | 8.5 |
| (S,S)-fenoterol | 184.20 ± 26.10 | 1856.20 ± 925.76 | 580 |
| (R,R)-4-methoxyfenoterol | 0.17 ± 0.02 | 13.50 ± 5.59 | 0.3[a] |
| (R,S)-4-methoxyfenoterol | 2.01 ± 0.76 | | 2.0[a] |
| (S,R)-4-methoxyfenoterol | 3.16 ± 0.71 | | 7.2 |
| (S,S)-4-methoxyfenoterol | 337.20 ± 97.20 | | 33.2 |
| (R,R)-1-naphthylfenoterol | 1.57 ± 0.34 | | 12.5[a] |
| (R,S)-1-naphthylfenoterol | 1.19 ± 0.38 | | 2.7[a] |
| (S,R)-1-naphthylfenoterol | 14.80 ± 5.59 | | 66.7 |
| (S,S)-1-naphthylfenoterol | 229.10 ± 57.40 | | 29.7 |
| (R,R)-ethylfenoterol | 1.44 ± 0.27 | | 2.8[a] |
| (R,S)-ethylfenoterol | 17.88 ± 4.56 | | 16.6[a] |
| (R,R)-2-naphthylfenoterol | 1.91 ± 0.57 | | 0.4[a] |
| (R,S)-2-naphthylfenoterol | 72.60 ± 29.31 | | 7.6[a] |
| (R,R)-4-methoxy-1-naphthylfenoterol | 3.98 ± 0.28 | 68.97 ± 5.59 | 3.9[a] |
| (R,S)-4-methoxy-1-naphthylfenoterol | 4.37 ± 0.70 | 88.24 ± 5.59 | 4.0[a] |

Figure 7A:
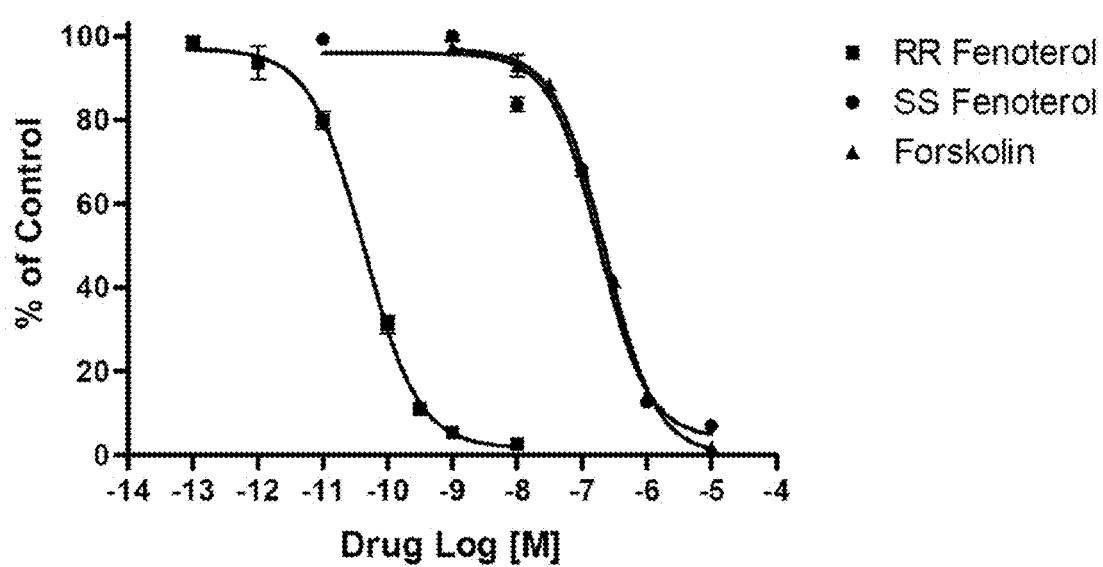
FIGS. 7A and 7B illustrate dose-dependent inhibition of [$^3$H]thymidine incorporation by fenoterol isomers and forskolin.
Figure 7B:
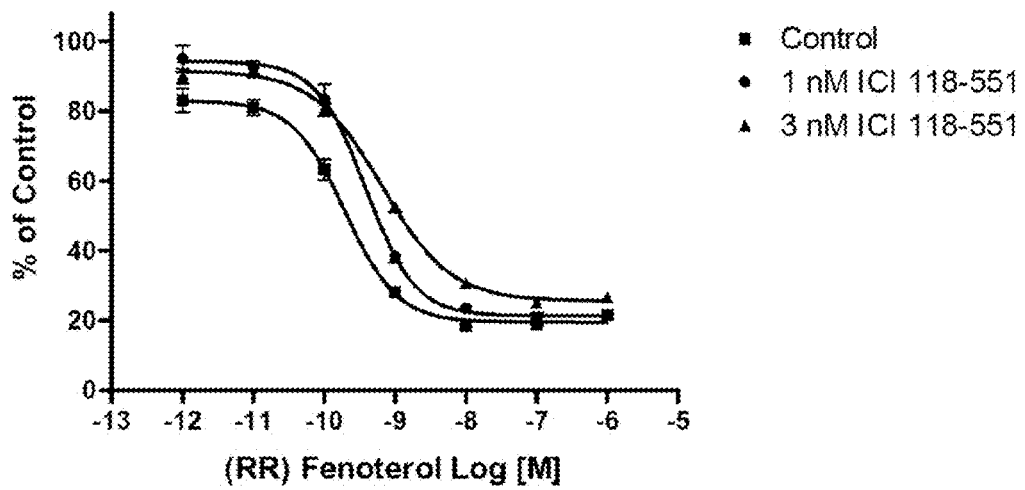

Forskolin-induced increases in intracellular cAMP produced decreased proliferation in 1321N1 cell line with a calculated IC$_{50}$ value of 170.3±37.2 (FIG. 7A). Since the results of the studies with forskolin demonstrated that 1321N1 cells are sensitive to increases in intracellular cAMP concentrations, the effect of $\beta_2$-AR agonists on cellular proliferation in 1321N1 and U87MG cells was investigated. In this study, 1321N1 cells were incubated with $\beta_2$-AR agonists for 22 hours, at which time [$^3$H]-thymidine was added for an additional 2 hours, the cells were then harvested and [$^3$H]-thymidine incorporation was determined. Significant reductions in [$^3$H]-thymidine incorporation were observed in a concentration-dependent manner for all of the compounds used in the study (FIG. 7A). In particular, FIG. 7A shows that (R,R)-fenoterol (■) is 1000 times more potent than both (S,S)-fenoterol (▼) and forskolin (●). The data was used to determine $IC_{50}$ values associated with the inhibition of [$^3$H]-thymidine incorporation and the values ranged from 0.05 nM observed with (R)-isoproterenol to 337.2 nM observed with (S,S)-4-methoxyfenoterol, Table 8. The inhibitory effect of (R,R)-fenoterol was blocked by the addition of the $\beta_2$-AR antagonist propranolol (1 µM) and competitively inhibited by ICI 118-551, pA2=8.9, slope −1.3±0.3, FIG. 7B.

The stimulation of cAMP accumulation in 1321N1 cells was examined for 6 of the 19 compounds used in the mitogenesis inhibition studies and the calculated $EC_{50cAMP}$ and $IC_{50}$ values were compared. A log-log correlation of the data revealed an excellent correlation between the two values with an $r^2$=0.93652. Although there were quantitative differences between the $EC_{50cAMP}$ values of the 6 compounds determined in 1321N1 cells and in HEK-$\beta_2$-AR cells, the correlation was repeated using the 19 $EC_{50cAMP}$ values determined in the HEK-$\beta_2$-AR cells and the 19 $IC_{50}$ values determined in the 1321N1 cells. A significant correlation was also observed between the two data sets, $r^2$=0.72611. The results indicate that there is a significant relationship between cAMP stimulation in the HEK-$\beta_2$-AR cell line and the inhibition of [$^3$H]-thymidine incorporation in 1321N1 cell line and that the HEK-$\beta_2$-AR cell line can be a useful screen for anti-mitogenesis activity.

The incubation of U87MG cells with β2-AR agonists had no effect on [$^3$H]-thymidine incorporation which is consistent with the lack of expression of the $\beta_2$-AR in this cell line. It is interesting to note that $\beta_2$-AR agonists also had no effect on the proliferation of HEK-$\beta_2$-AR cells, although the compounds used in this study are highly active in the stimulation of cAMP accumulation in these cells, Table 8. These studies demonstrated that $\beta_2$-AR agonists inhibit proliferation of 1321N1 cells in vitro.

The effect of (R,R)-fenoterol on cell cycling in 1321N1 was determined by treating the cells with various concentrations of (R,R)-fenoterol for 20 hours followed by flow cytometric analysis. Untreated cells were used as controls. (R,R)-fenoterol induced $G_1$ arrest with an associated decrease in the proportion of cells in $G_2$ and S phase, as the proportion of cells in $G_1$ phase increased from 49.8% (controls) to 60.6-76% in treated cells, Table 9. The results also demonstrated that (R,R)-fenoterol arrested the cell cycle at doses as low as 0.1 nM, which is consistent with the compound's ability to stimulate cAMP accumulation and inhibit [$^3$H]-thymidine incorporation, Table 8. These results show that activation of PKA by cAMP analogs induced cell growth arrest by blocking the cell cycle during the $G_1$ or $G_2$ phase.

TABLE 9

Effect of (R,R)-fenoterol on 1321N1 Cell Cycle Kinetics

| (R,R)-fenoterol [nM] | % Phase Distribution | | |
|---|---|---|---|
| | G1 | G2 | S |
| Control | 49.8 | 6.5 | 43.7 |
| 0.1 | 60.6 | 1.8 | 37.6 |
| 10.0 | 76.0 | 2.1 | 21.9 |
| 1000 | 74.7 | 0.7 | 24.6 |

Figure 8A:
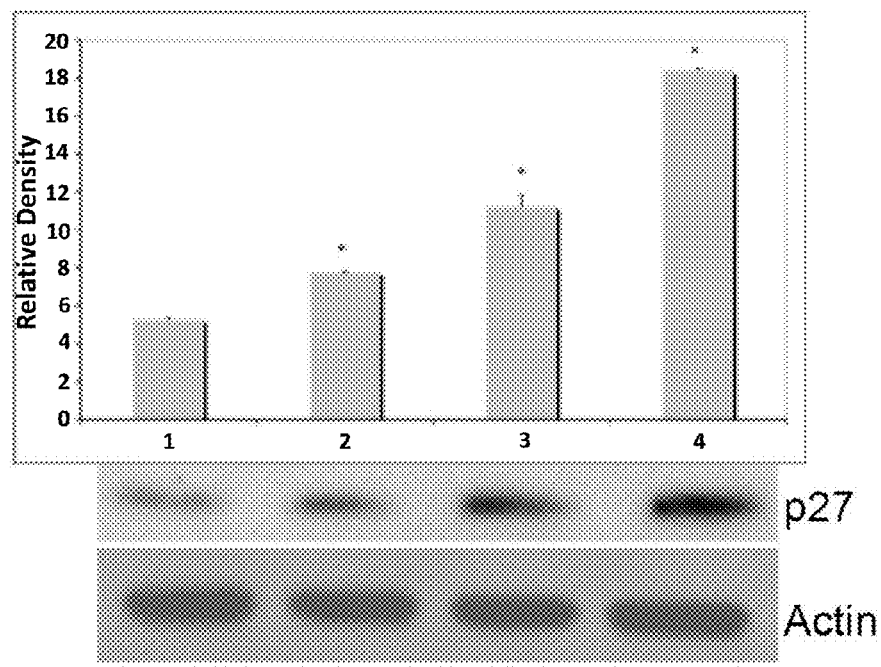
FIGS. 8A-8E illustrate (R,R)-fenoterol-modulation of P27 (FIG. 8A), phospho AKT (FIG. 8B), Cyclin D1 (FIG. 8C), Cyclin A (FIG. 8D) and p-Erk1/2 protein expression levels. In each case, the lanes were as follows: lane 1, control; lane 2, $10^{-10}$ M (R,R)-fenoterol; lane 3, $10^{-8}$ M (R,R)-fenoterol; and lane 4, $10^{-6}$ M (R,R)-fenoterol. Western blots were quantified using densitometry. The relative density of the bands is shown above each western blot.
Figure 8B:
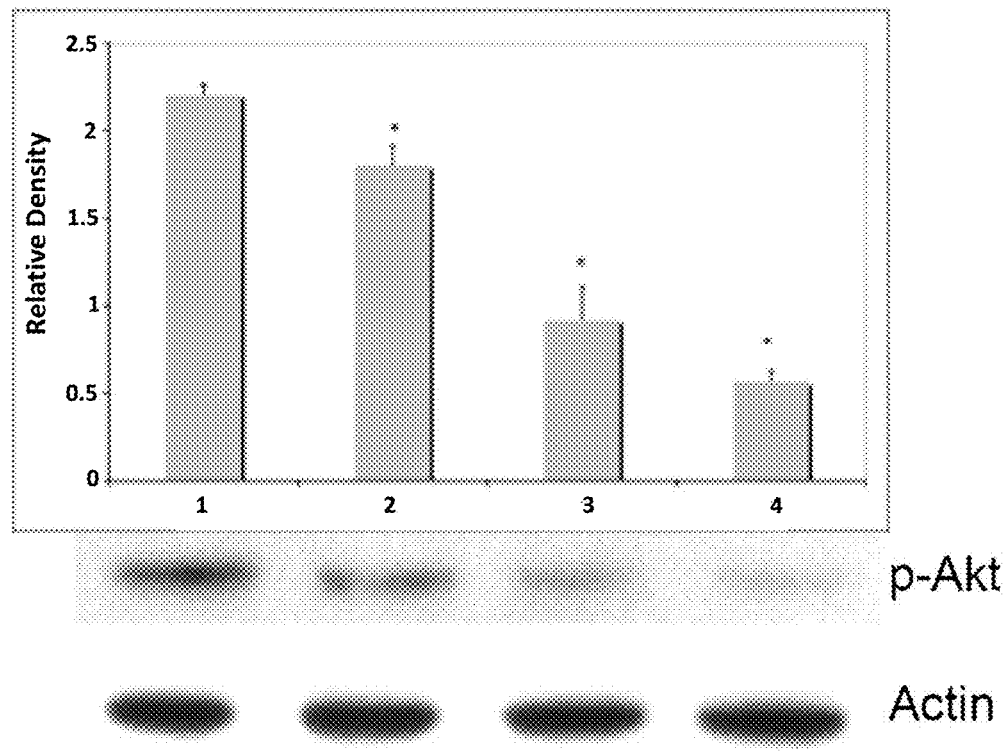
Figure 8C:
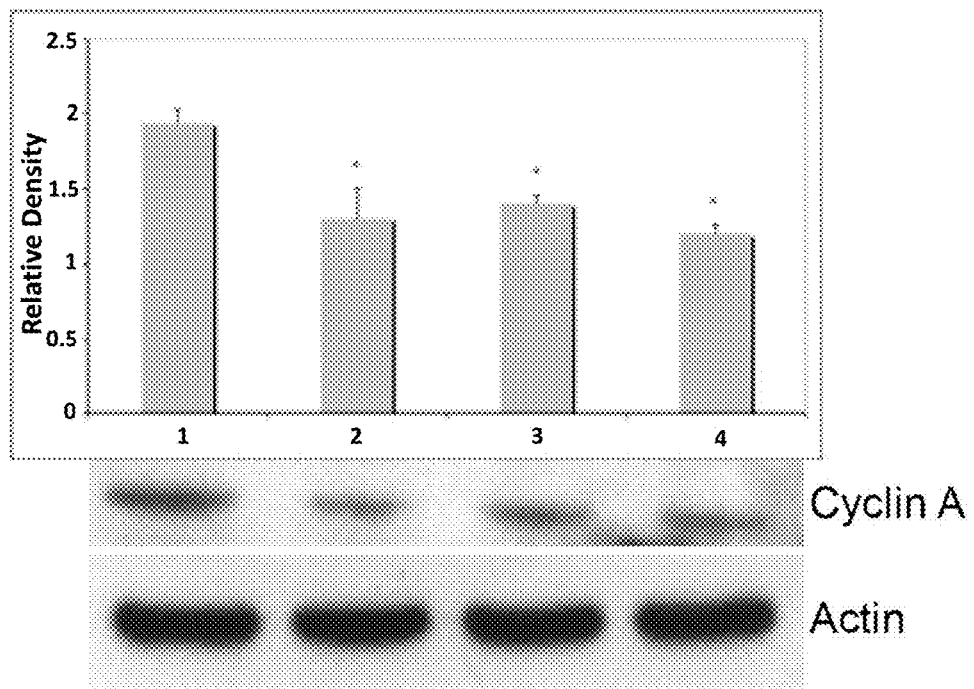
Figure 8D:
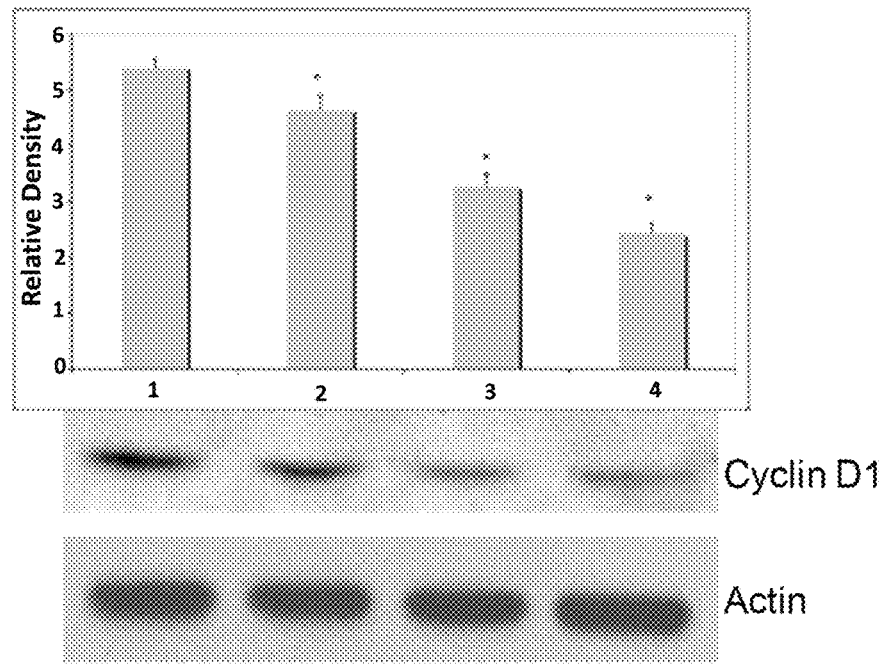
Figure 8E:
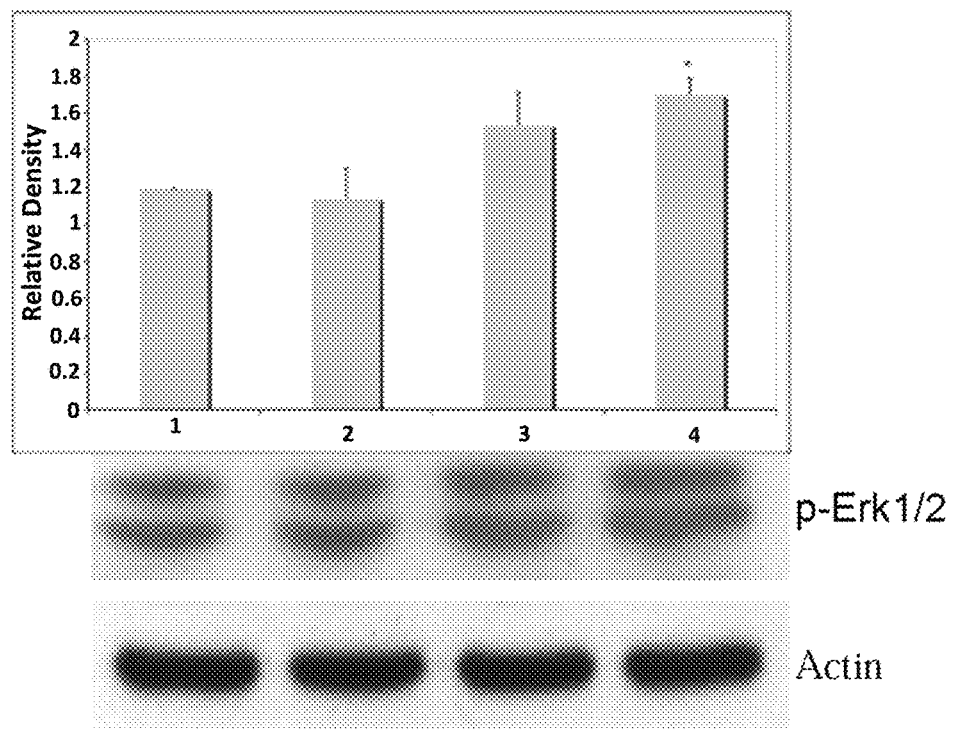

The effect of (R,R)-fenoterol on selected molecular events associated with $G_1$ arrest in 1321N1 cells was examined using Western blot analysis. The data indicate that (R,R)-fenoterol significantly increased protein levels of the cyclin-dependent kinase inhibitor and p27 (FIG. 8A) and inhibited phosphorylation of Akt, at Ser-473, in a dose dependent manner at nanomolar concentrations, FIG. 8B. At the same range of concentrations, (R,R)-fenoterol down-regulated the protein expression of cyclin D1 and cyclin A, FIGS. 8C and 8D, but had only a modest effect on phosphorylation of mitogen-activated kinases ERK1/2, reaching significance at only a single concentration (FIG. 8E).

In the current study, treatment of 1321N1 cells with forskolin increased the basal intracellular concentration of cAMP from below 0.5 nmol/mg protein to ~4 nmol/mg protein and induced cell cycle arrest in $_{G1}$ phase. Thus, the data indicate that the proliferation of 1321N1 cells is also sensitive to changes in intracellular cAMP levels, that these levels can be increased by treatment with $\beta_2$-AR agonists and that this effect is associated with the presence of functional $\beta_2$-AR in the 1321N1 cells. The connection between $\beta_2$-AR stimulation and the inhibition of mitogensis was supported by data from studies utilizing U87MG cells, which do not express functional $\beta_2$-AR. The treatment of U87MG cells with the same series of $\beta_2$-AR agonists did not increase cAMP levels and had no effect on [$^3$H]-thymidine incorporation or cell proliferation. In addition, studies of the human-derived U118 glioma cell line indicate that there is a low, but significant expression of $_{\beta2}$-AR in these cells. Treatment of U118 cells with (R,R)-fenoterol inhibited [$^3$H]-thymidine incorporation with an $IC_{50}$ value that was 50-fold higher than the value calculated in the 1321N1 cells suggesting that the level of $\beta_2$-AR expression affected the quantitative inhibitory activity of (R,R)-fenoterol.

The mechanism by which cAMP arrests cell growth has been characterized in astrocytomas and other cell types. The data from these studies indicate that cAMP can reduce cell growth by inhibiting the growth factor-mediated cell proliferation signaling pathways such as ERK and PI3K (Cook and McCormick, *Science* 262(5136): 1069-1072, 1993; Sevetson et al., *J. Mol. Neurosci.* 17(3): 1993; Kim et al., *J. Biol. Chem.* 276(16): 12864-12870, 2001); Stork and Schmitt, *Trends Cell Biol.* 12(6): 258-266, 2002), by elevating the levels of cell cycle inhibitor proteins p21$^{cip1}$ (Lee et al., 2000) and p27$^{kip1}$ (van Oirschot et al., *J. Biol. Chem.* 276(36): 33854-33860, 2001) and/or by decreasing the level of cyclin D1 protein (L'Allemain et al., *Oncogene* 14(16): 1981-1990, 1997).

In this study, the data from studies utilizing (R,R)-fenoterol indicated that ERK1/2 activity, reported to be crucial for cyclin D1 induction was only modestly affected by (R,R)-fenoterol, although cyclin D1 was nevertheless down regulated, as was Akt phosphorylation. Conversely, the cell cycle inhibitor p27 was up-regulated. It is quite likely that in the 1321N1 cells the inhibition of cyclin D1 production by cAMP is at least in part due to the inhibition of PI3K/Akt pathway. Since (R,R)-fenoterol inactivated Akt, it is possible that the increase in p27$^{kip1}$ and decrease in cyclin D1 is a reflection of both direct action of cAMP on these proteins as well as an indirect action through inactivation of Akt. In addition, the finding that (R,R)-fenoterol decreased the level of cyclin A suggests that the fenoterol compounds cause growth inhibition through modulation of multiple phases of cell cycle.

All of the 19 compounds used in this Example had been characterized previously (including herein) as full $\beta_2$-AR agonists in HEK-$\beta_2$-AR cells, with $EC_{50cAMP}$ values ranging from 0.2 nM to 580 nM (see Jozwiak et al., *J. Med. Chem.,* 50: 2904-2915, 2007 and Jozwiak et al., *Bioorg. Med. Chem.,* 18: 728-736, 2010). The ability of 6 of the 19 compounds used in this study to stimulate cAMP accumulation in 1321N12 cells was determined and the results indicated that the compounds were weaker agonists in this cell line as compared to the HEK-$\beta_2$-AR cells, Table 8. However, although there were quantitative differences in the agonist activities of the tested compounds, the calculated $EC_{50cAMP}$ values from both the 1321N1 and HEK-$\beta_2$-AR cells were correlated to the observed inhibition of [$^3$H]-thymidine incorporation. This observation is reflected in the observed activity of (S,S)-fenoterol, which is a weak partial $\beta_2$-AR agonist in the 1321N1, FIG. 6, a full $\beta_2$-AR agonist (>100% accumulation) in HEK-$\beta_2$-AR cells and an effective inhibitor of mitogensis, Table 8. The data obtained with (S,S)-fenoterol suggests that a very small increase in cAMP accumulation is sufficient to block cell division in 1321N1 cells.

Using previously described techniques, the $IC_{50}$ data obtained in this study and the related molecular structures of the fenoterol analogs were used in a preliminary comparative molecular field analysis to generate a statistically valid model ($R^2$=0.771; $Q^2$=0.569; F=25.3, SEE=0.491). Unlike the CoMFA model obtained in the studies with the HEK-$\beta_2$-AR cell line, the results of this study suggest that the $IC_{50}$ values of the tested compounds are associated with the configurations at both of the fenoterol molecule's chiral centers of the compounds with the structure of the aromatic substituent on the aminoalkyl chain playing little or no role. The difference in the CoMFA models is reflected in the effects of (R,R)-ethylfenoterol and (S,S)-fenoterol in cardiomyocyte contractility and the inhibition of [$^3$H]-thymidine incorporation. Both of these compounds are essentially inactive in the rat cardiomyocyte contractility model with $EC_{50}$ values of 8,551 nM and 55,000 nM, respectively, while active inhibitors of mitogensis in the 1321N1 cell line with $IC_{50}$ values of 1.44 nM and 184.20 nM, respectively. Without being bound by a particular theory, it is contemplated that the vast differences between the activities of these compounds in the two test systems may be the relative abundance of differing conformations of the $\beta_2$-AR and the ability of the fenoterol analogs to stabilize or induce these forms.

Additional studies were performed on a series of the N-alkyl derivatives of (R,R)-4-methoxyfenoterol and characterized for activity in the 1321N1 ([$^3$H]-thymidine incorporation) and cardiomyocyte models (rat cardiomyocyte contractility). The data is as follows, all for the (R,R)-isomers: 4-methoxy-ethylfenoterol: $IC_{50}$ (1321N1)=14 nM; $EC_{50}$ (cardio)>10,000 nM; and 4-methoxy-isopropylfenoterol: $IC_{50}$ (1321N1)=946 nM; $EC_{50}$ (cardio)>10,000 nM.

The results of this study indicate that $\beta_2$-AR agonists inhibited cellular replication in the 1321N1 cell line, that this effect was blocked by the $\beta_2$-AR antagonist propranolol and that the $\beta_2$-AR agonists had no effect on the growth of U87MG cells. The results also indicate that the stereochemistries at the two chiral centers on the fenoterol molecule play a key role in the level of inhibitory activity, and that the inhibition of mitogenesis in the 1321N1 cell line may stem from the binding of the fenoterol derivatives to a conformation of the $\beta_2$-AR that differs from the antagonist-bound conformation of the receptor explored in the earlier studies.

Example 9

Brain and Plasma Analysis of [$^3$H]-(R,R)-Methoxyfenoterol in Male Sprague-Dawley Rats This example shows the brain-to-plasma distribution of [$^3$H]-(R,R)-methoxyfenoterol after a single intravenous (IV) administration in male Sprague-Dawley rats.

Male Sprague-Dalwey rats (6 weeks of age, 206-220 grams) were randomly assigned to treatment groups by a manual body weight stratification procedure. An overview of the research study design for evaluating the brain-to-plasma distribution of [$^3$H](R,R)-methoxyfenoterol is provided in Table 10 below.

TABLE 10

Research Study design for Brain and Plasma Analysis of [$^3$H]-(R,R)-methoxyfenoterol in Male Sprague-Dawley Rats.

| Group | Dose Route (slow push over 30 sec.) | Dose Level (mg/kg) | Dose Conc. (mg/ml) | µCi/kg | No. of Male Rats | Blood and Brain Tissue Harvest Times (min)[b] |
|---|---|---|---|---|---|---|
| 1 (controls) | IV | 0[a] | 0 | 0 | 3 | 5 |
| 2 | IV | 5 | 2.5 | 250 | 3 | 5 |
| 3 | IV | 5 | 2.5 | 250 | 3 | 15 |
| 4 | IV | 5 | 2.5 | 250 | 3 | 30 |
| 5 | IV | 5 | 2.5 | 250 | 3 | 60 |

[a]Control group animals only received vehicle.
[b]Animals were sacrificed at specified times in order to collect blood and whole brain tissue.

The test article included (R,R)-methoxyfenoterol 0.5 fumarate (375.42) stored at room temperature and [$^3$H]-(R, R)-methoxyfenoterol chloride (353.9) stored at 4° C. to −20° C. (specific activity 57 Ci/mmol); vehicle was sterile saline, 0.9% sodium chloride, USP. Dose formulations were prepared on the day of the study. The amount of radioactivity in the dose formulation was determined by liquid scintillation. The study lasted for an hour and radioactivity levels in plasma and brain tissue were evaluated at the conclusion of the study. Approximately 5 mls of whole blood was collected. Blood samples were collected via cardiac puncture, transferred into a tube containing $K_3$EDTA as the anticoagulant and kept on wet ice until processed to plasma. To generate plasma, samples were centrifuged within 15 minutes of collection at 2,500 RPM for 15 minutes at room temperature. Plasma was divided equally into three labeled cryovials and stored on ample dry ice until transferred to a freezer set at ≤−20° C. for storage until analysis. Duplicate aliquots were weighed and then combined with scintillation cocktail. The [$^3$H] radioactivity was determined on a liquid scintillation counter. Brain samples were snap frozen in liquid nitrogen and stored at ≤−70° C. until analysis. Whole brain tissue was homogenized and the weight of the homogenate was determined Duplicate aliquots from the homogenate were weighed, solubilized and then combined with scintillation cocktail. The [$^3$H] radioactivity was determined on a liquid scintillation counter.

Male Sprague-Dawley rats were administered 5 mg/kg [$^3$H]-(R,R)-methoxyfenoterol intravenously and the corresponding plasma and brain levels were determined over 60 minutes. After 5 minutes, plasma levels where highest at 3.25±0.15 µg-equiv/ml and then subsequently decreased by 62% to 1.24±0.43 µg-equiv/ml at 60 minutes (Table 11, FIG. 9). There was a similar, yet less dramatic trend with [$^3$H]-(R,R)-methoxyfenoterol levels in the brain. The highest and lowest values were 0.92±0.10 and 0.70±0.37 µg-equiv/g, respectively. A comparison of brain to plasma levels showed that after 15 minutes that ratio appeared to stabilize around 0.5. The actual percent dose found in the brain was no more than 0.17% for any given animal.

appreciate that they also provide support for using other fenoterol analogues and fenoterol itself to treat an astrocytoma, but inhibiting astrocytoma growth, in additional subjects, including humans.

Example 11

Treatment of a Primary Brain Tumor

This example describes a method that can be used to treat a primary brain tumor in a human subject by administration of a composition comprising fenoterol, a fenoterol analogue or a combination thereof at a therapeutically effective amount to reduce or inhibit on or more signs or symptoms associated with the primary brain tumor. Although particular methods, dosages, and modes of administrations are provided, one skilled in the art will appreciate that variations can be made without substantially affecting the treatment.

A subject with an astrocytoma is selected based upon clinical symptoms. A biological sample is isolated from the subject and β2-AR expression determined by Western Blot or histological studies. A positive result indicates that the

TABLE 11

[$^3$H]-(R,R)-methoxyfenoterol Levels and Dose Recovery in Male Rat Plasma and Brain

| Time (min) | Rat #[a,b] | Plasma (µg-equiv/ml) | | | Brain (µg-equiv/g) | | | Ratio of Brain/Plasma | | | Percent of Dose in Brain (%) | | |
|---|---|---|---|---|---|---|---|---|---|---|---|---|---|
| | | Individual | Mean | SD | Individual | Mean | SD | Individual | Mean | SD | Individual | Mean | SD |
| 5 | 4 | 3.30 | 3.25 | 0.15 | 1.00 | 0.92 | 0.10 | 0.30 | 0.28 | 0.02 | 0.15 | 0.14 | 0.02 |
| | 5 | 3.08 | | | 0.80 | | | 0.26 | | | 0.12 | | |
| | 6 | 3.37 | | | 0.95 | | | 0.28 | | | 0.15 | | |
| 15 | 7 | 2.19 | 1.79 | 0.78 | 0.99 | 0.80 | 0.39 | 0.45 | 0.44 | 0.03 | 0.15 | 0.12 | 0.06 |
| | 8 | 0.89 | | | 0.36 | | | 0.40 | | | 0.06 | | |
| | 9 | 2.29 | | | 1.06 | | | 0.46 | | | 0.16 | | |
| 30 | 10 | 0.63 | 1.53 | 0.78 | 0.22 | 0.72 | 0.44 | 0.35 | 0.45 | 0.09 | 0.03 | 0.11 | 0.07 |
| | 11 | 1.97 | | | 1.00 | | | 0.51 | | | 0.15 | | |
| | 12 | 2.00 | | | 0.95 | | | 0.48 | | | 0.15 | | |
| 60 | 13 | 0.97 | 1.24 | 0.43 | 0.44 | 0.70 | 0.37 | 0.45 | 0.54 | 0.10 | 0.06 | 0.11 | 0.06 |
| | 14 | 1.01 | | | 0.53 | | | 0.52 | | | 0.09 | | |
| | 15 | 1.73 | | | 1.12 | | | 0.65 | | | 0.17 | | |

[a]Untreated rats (# 1-3) had no radioactivity above background in plasma or brain.
[b]Treated rats were administered 5 mg/kg $^3$H-Methoxyfenoterol by intravenously.

These studies demonstrate that (R,R)-methoxyfenoterol is capable of passing through the blood brain barrier and that administration of such compound as well as likely other related fenoterol analogues and fenoterol by IV is an effective means of delivering these compounds to the brain, such as to treat a brain tumor.

Example 10

Effect of (R,R)-Methoxyfenoterol Growth of 1321N1 Xenograft Implanted in the Flank of SKID Mice This example shows the ability of (R,R)-methoxyfenoterol to inhibit 1321N1 tumor growth in vivo.

(R,R)-methoxyfenoterol was administered twice a day via IP (day 1-2, 0 mg/kg/day; day 3-10, 30 mg/kg/day; and day 10-42, 50 mg/kg/day). FIG. 10 illustrates the ability of (R,R)-methoxyfenoterol to inhibit growth of a 1321N1 xenograft implanted in the flank of SKID mice.

These studies demonstrate that (R,R)-methoxyfenoterol inhibits astrocytoma growth in vivo. Although these studies demonstrate that (R,R)-methoxyfenoterol is capable of inhibiting astrocytoma growth, one of skill in the art will tumor may be treated by administration of fenoterol, a disclosed fenoterol analogue or a combination thereof. In one particular example, a tissue biopsy is obtained from a subject with a primary brain tumor. β2-AR expression is determined in the sample. The detection of β2-ARs in the sample indicates that the primary brain tumor can be treated by administration of a composition including (R,R)-4-methoxy-ethylfenoterol. (R,R)-4-methoxy-ethylfenoterol is administered IP to the subject at a concentration of 30 mg/kg/day for the first 10 days and 50 mg/kg/day for the remaining 32 days. Tumor growth is then assessed 7 days, 14 days, 21 days, 30 days and 42 days following treatment. In one example, the effectiveness of the treatment is determined by imaging methods, including non-invasive, high-resolution modalities, such as computed tomography (CT) and especially magnetic resonance imaging (MRI). For example, contrast agent uptake is monitored to determine the effectiveness of the treatment. A decrease in permeability to the blood-brain barrier marked by an at least 20% decrease in uptake of a contrast agent as compared to reference value or that measured prior to treatment indicates the treatment is effective. Also, a twenty-percent reduction in tumor size as compared to tumor size prior to treatment is considered to be an effective treatment.

Example 12

Use of Disclosed Compositions Including (R,R)-4-methoxy-ethylfenoterol and (S,R)-4-methoxy-ethylfenoterol as an Adjuvant Therapy This example describes a method that can be used to reduce, prevent or retard tumor growth in a human subject that has been treated for a malignant astrocytoma.

A subject with an astrocytoma is selected based upon clinical symptoms. The primary form of treatment of the malignant astrocytoma is open surgery. For subjects that are not surgical candidates, either radiation or chemotherapy is used as the initial treatment. Following the initial treatment, a subject is administered a pharmaceutical composition containing 3 parts (S,R)-4-methoxy-ethylfenoterol and 1 part (R,R)-4-methoxy-ethylfenoterol orally daily for an indefinite period of time. The reoccurrence of tumor growth is monitored by imaging methods, including non-invasive, high-resolution modalities, such as CT and MRI.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of reducing growth of primary brain tumor cells, pancreatic cancer cells, breast cancer cells, or lung cancer cells that express a β2-adrenergic receptor (β2-AR), comprising:
reducing growth of primary brain tumor cells, pancreatic cancer cells, breast cancer cells, or king cancer cells that express a β2-AR by exposing the primary brain tumor cells, pancreatic cancer cells, breast cancer cells, or lung cancer cells to an effective amount of a compound,

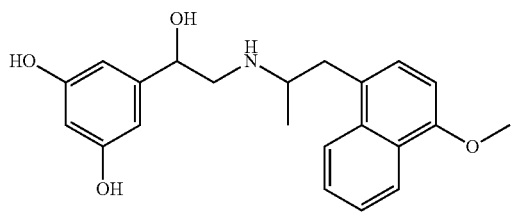 [SMILES: COc1ccc(CC(C)NCC(O)c2cc(O)cc(O)c2)c2ccccc12]

and wherein the compound is optically active.

2. The method of claim 1, wherein the primary brain tumor cells are astrocytoma cells or glioblastoma cells.

3. The method of claim 1, wherein the compound is (R,R')-(−)-4-methoxy-1-naphthylfenoterol, (R,S')-(−)-4-methoxy-1-naphthylfenoterol, (S,R')-(−)-4-methoxy-1-naphthylfenoterol or a combination thereof.

4. The method of claim 1, wherein exposing the primary brain tumor cells, pancreatic cancer cells, breast cancer cells, or lung cancer cells to the compound comprises administering a therapeutically effective amount of the compound to a subject having a tumor expressing a β2-AR, thereby reducing one or more symptoms associated with the tumor.

5. The method of claim 4, wherein the tumor is a primary brain tumor, pancreatic cancer, breast cancer, or lung cancer.

6. The method of claim 4, wherein the tumor is an astrocytoma or a glioblastoma.

7. The method of claim 4, wherein the tumor is pancreatic cancer.

8. The method of claim 4, wherein the tumor is breast cancer.

9. The method of claim 4, wherein the tumor is lung cancer.

10. The method of claim 4, wherein reducing one or more symptoms associated with the tumor comprises reducing tumor growth, reducing tumor volume, or both.

11. The method of claim 4, wherein the compound is (R,R')-(−)-4-methoxy-1-naphthylfenoterol, (R,S')-(−)-4-methoxy-1-naphthylfenoterol, (S,R')-(−)-4-methoxy-1-naphthylfenoterol or a combination thereof.

12. The method of claim 4, wherein the subject does not have a bleeding disorder prior to administering a therapeutically effective amount of the compound.

13. The method of claim 4, further comprising administering an additional chemotherapeutic agent prior to, concurrent or subsequent to administering the compound.

14. The method of claim 4, wherein the additional chemotherapeutic agent is carmustine, lomustine, procarbazine, streptozocin, 5-fluorouracil, paclitaxel, doxorubicin, or a combination thereof.

15. The method of claim 4, wherein administering a therapeutically effective amount of the compound comprises administering a therapeutically effective amount of the compound with a pharmaceutically acceptable carrier.

16. The method of claim 4, wherein the subject is a human.

* * * * *

UNITED STATES PATENT AND TRADEMARK OFFICE
CERTIFICATE OF CORRECTION

PATENT NO. : 10,130,594 B2
APPLICATION NO. : 15/273147
DATED : November 20, 2018
INVENTOR(S) : Irving W. Wainer et al.

Page 1 of 1

It is certified that error appears in the above-identified patent and that said Letters Patent is hereby corrected as shown below:

In the Claims

Column 75, In Claim 1, Line 32, "king cancer cells" should read --lung cancer cells--.

Signed and Sealed this
Third Day of September, 2019

Andrei Iancu
*Director of the United States Patent and Trademark Office*